United States Patent
Choi

(10) Patent No.: US 10,525,030 B2
(45) Date of Patent: *Jan. 7, 2020

(54) PHENYL CARBAMATE COMPOUND AND A COMPOSITION FOR NEUROPROTECTION COMPRISING THE SAME

(71) Applicant: Bio-Pharm Solutions, Co., Ltd., Gyeonggi-do (KR)

(72) Inventor: Yong Moon Choi, Pine Brook, NJ (US)

(73) Assignee: BIO-PHARM SOLUTIONS CO., LTD., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/774,898

(22) PCT Filed: Mar. 12, 2014

(86) PCT No.: PCT/KR2014/002059
§ 371 (c)(1),
(2) Date: Sep. 11, 2015

(87) PCT Pub. No.: WO2014/142547
PCT Pub. Date: Sep. 18, 2014

(65) Prior Publication Data
US 2016/0015680 A1      Jan. 21, 2016

Related U.S. Application Data

(60) Provisional application No. 61/776,926, filed on Mar. 12, 2013.

(30) Foreign Application Priority Data

Jun. 10, 2013 (KR) .................. 10-2013-0065781

(51) Int. Cl.
| | | |
|---|---|---|
| *A61K 31/325* | (2006.01) | |
| *A61K 31/27* | (2006.01) | |
| *A61K 31/166* | (2006.01) | |
| *C07C 271/12* | (2006.01) | |
| *C07C 271/24* | (2006.01) | |

(52) U.S. Cl.
CPC .......... *A61K 31/27* (2013.01); *A61K 31/166* (2013.01); *A61K 31/325* (2013.01); *C07C 271/12* (2013.01); *C07C 271/24* (2013.01); *C07C 2601/02* (2017.05); *C07C 2601/14* (2017.05); *C07C 2602/42* (2017.05); *Y02A 50/409* (2018.01)

(58) Field of Classification Search
CPC ..... A61K 31/27; A61K 31/325; A61K 31/166
USPC ........................................ 514/480
See application file for complete search history.

(56) References Cited

U.S. PATENT DOCUMENTS

| | | | |
|---|---|---|---|
| 3,265,728 A * | 8/1966 | Bossinger | A61K 31/27 560/163 |
| 3,313,696 A | 4/1967 | Bossinger et al. | |
| 6,541,513 B2 | 4/2003 | Plata-Salaman et al. | |
| 9,872,847 B2 * | 1/2018 | Choi | C07C 271/12 |
| 2002/0165273 A1 | 11/2002 | Plata-Salaman et al. | |
| 2004/0171679 A1 | 9/2004 | Plata-Salaman | |
| 2008/0103199 A1 * | 5/2008 | Haas | A61K 31/165 514/483 |
| 2009/0137652 A1 * | 5/2009 | Twyman | A61K 31/325 514/397 |
| 2013/0005801 A1 | 1/2013 | Choi | |
| 2014/0275243 A1 * | 9/2014 | Choi | C07C 271/12 514/487 |
| 2016/0015679 A1 * | 1/2016 | Choi | A61K 31/166 514/480 |
| 2016/0016896 A1 * | 1/2016 | Choi | A61K 31/166 514/487 |

FOREIGN PATENT DOCUMENTS

| | | |
|---|---|---|
| CN | 103080079 A | 5/2013 |
| KR | 100886578 B1 | 3/2009 |
| KR | 1020090067210 A | 6/2009 |
| KR | 20090082213 A | 7/2009 |
| KR | 100910928 B1 | 8/2009 |
| WO | 02/067925 A1 | 6/2002 |
| WO | WO 02051395 A1 | 7/2002 |
| WO | 2008048801 A2 | 4/2008 |
| WO | 2008048802 A1 | 4/2008 |
| WO | WO 2012096458 A2 | 7/2012 |
| WO | 2013/100568 A1 | 7/2013 |
| WO | 2013/100569 A1 | 7/2013 |

OTHER PUBLICATIONS

Faure et al. Epilepsia (2013), 54(7), p. 1203-1213.*
International Search Report for corresponding PCT application No. PCT/KR2014/002059, dated Jun. 27, 2014.
Office Action dated Sep. 7, 2016 issued in the counterpart KR Patent Application No. 10-2015-7026364.
Extended European Search Report for corresponding European application No. 14762900.0, dated Dec. 19, 2016.
Office action for corresponding Chinese application No. 201480015484. 5, dated Jan. 9, 2017.

* cited by examiner

*Primary Examiner* — Yong L Chu
(74) *Attorney, Agent, or Firm* — McDonnell Boehnen Hulbert & Berghoff LLP

(57) ABSTRACT

The present invention relates to a composition for neuroprotection comprising a phenyl carbamate compound and a method for providing neuroprotection therewith. The present invention ensures the enhancement of neuroprotection, such that it is promising for preventing or treating various diseases associated with neurological injury.

7 Claims, 10 Drawing Sheets

PHENYL CARBAMATE COMPOUND AND A COMPOSITION FOR NEUROPROTECTION COMPRISING THE SAME

BACKGROUND OF THE INVENTION

Field of the Invention

The present invention relates to a composition for neuroprotection comprising a phenyl carbamate compound and a method for providing neuroprotection therewith.

Description of the Related Art

Neuroprotection refers to the relative preservation of neuronal structure and/or function. In the case of an ongoing insult (a neurodegenerative insult) the relative preservation of neuronal integrity implies a reduction in the rate of neuronal loss over time, which can be expressed as a differential equation. It is a widely explored treatment option for many central nervous system (CNS) disorders. Neuroprotection aims to prevent or slow disease progression and secondary injuries by halting or at least slowing the loss of neurons. Neuroprotective treatments often target oxidative stress and excitotoxicity. both of which are highly associated with CNS disorders. Not only can oxidative stress and excitotoxicity trigger neuron cell death but when combined they have synergistic effects that cause even more degradation than on their own. Thus limiting excitotoxicity and oxidative stress is a very important aspect of neuroprotection. More neuroprotective treatment options exist that target different mechanisms of neurodegradation. One of them is Caspase inhibitors. these are primarily used and studied for their anti apoptotic effects. These Neuroprotection-related disorders are often associated with atrophy of the affected central or peripheral structures of the nervous system. They include diseases such as genetic brain disorders, Huntington's disease, autism and prion diseases. These disorders are those associated with progressive neuronal cell death or compromise over a period of time including, but not limited to, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease or spinocerebellar ataxia and olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy, familial dysautonomia or prion diseases that include, but not limited to Creutzfeldt-Jakob disease, Gerstmann-Sträussler-Scheinker disease, Kuru disease or fatal familial insomnia.

Autism is a disorder of neural development characterized by impaired social interaction and verbal and non-verbal communication, and by restricted, repetitive or stereotyped behavior. The diagnostic criteria require that symptoms become apparent before a child is three years old Autism affects information processing in the brain by altering how nerve cells and their synapses connect and organize; how this occurs is not well understood. It is one of three recognized disorders in the autism spectrum (ASDs), the other two being Asperger syndrome, which lacks delays in cognitive development and language, and pervasive developmental disorder, not otherwise specified (commonly abbreviated as PDD-NOS), which is diagnosed when the full set of criteria for autism or Asperger syndrome are not met.

Autism has a strong genetic basis, although the genetics of autism are complex and it is unclear whether ASD is explained more by rare mutations, or by rare combinations of common genetic variants. In rare cases, autism is strongly associated with agents that cause birth defects. Controversies surround other proposed environmental causes, such as heavy metals, pesticides or childhood vaccines; the vaccine hypotheses are biologically implausible and lack convincing scientific evidence. The prevalence of autism is about 1-2 per 1,000 people worldwide, and the Centers for Disease Control and Prevention (CDC) report 20 per 1,000 children in the United States are diagnosed with ASD as of 2012 [update] (up from 11 per 1,000 in 2008). The number of people diagnosed with autism has been increasing dramatically since the 1980s, partly due to changes in diagnostic practice and government-subsidized financial incentives for named diagnoses; the question of whether actual prevalence has increased is unresolved.

Parents usually notice signs in the first two years of their child's life. The signs usually develop gradually, but some autistic children first develop more normally and then regress. Early behavioral, cognitive, or speech interventions can help autistic children gain self-care, social, and communication skills. Although there is no known cure, there have been reported cases of children who recovered. Not many children with autism live independently after reaching adulthood, though some become successful. An autistic culture has developed, with some individuals seeking a cure and others believing autism should be accepted as a difference and not treated as a disorder.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventor has made intensive studies to develop a novel agent with excellent neuroprotecting activity which may be applied to effective treatment for various disease associated with neurological injury. As results, the present inventor has discovered that the phenyl carbamate derivatives represented by above formula 1 provide highly enhanced neuroprotecting activity.

Accordingly, it is an object of this invention to provide a composition for neuroprotection.

It is another object of this invention to provide a method for providing neuroprotection.

It is still another object of this invention to provide a method for preventing or treating a neurological disease.

Other objects and advantages of the present invention will become apparent from the following detailed description together with the appended claims and drawings.

DETAILED DESCRIPTION OF THE INVENTION

Figure 1A:
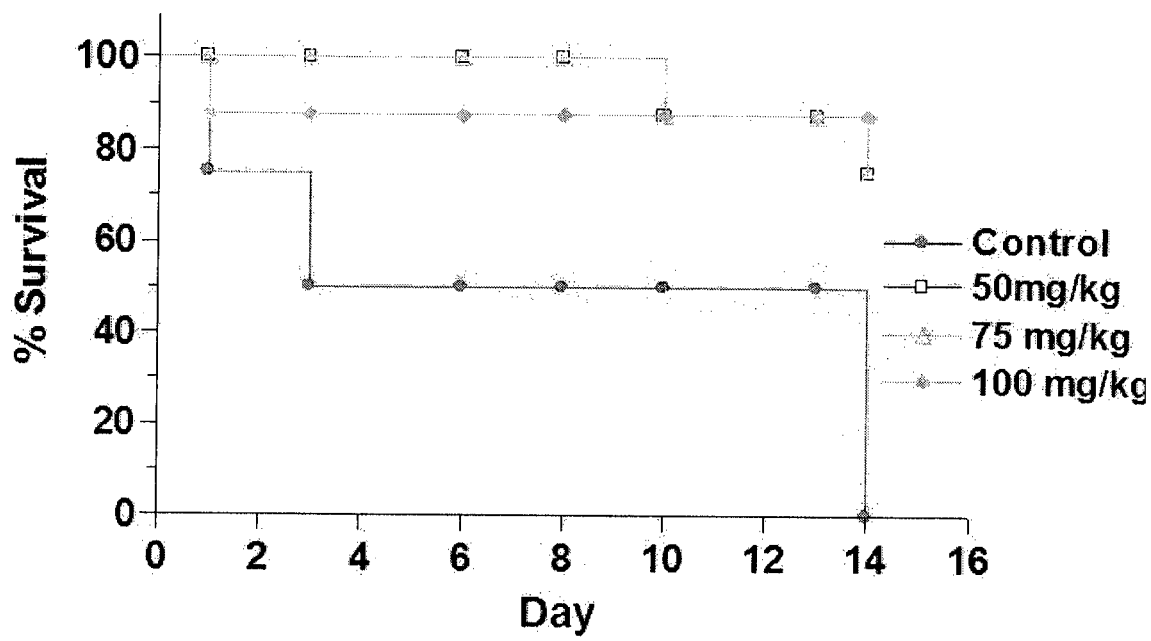
FIG. 1 represents survival rate (FIG. 1a) and body weight change (FIG. 1b) of the rats treated with the compounds of the present invention, and the control rats were treated with vehicle after administration of Li-pilocarpine.
Figure 1B:
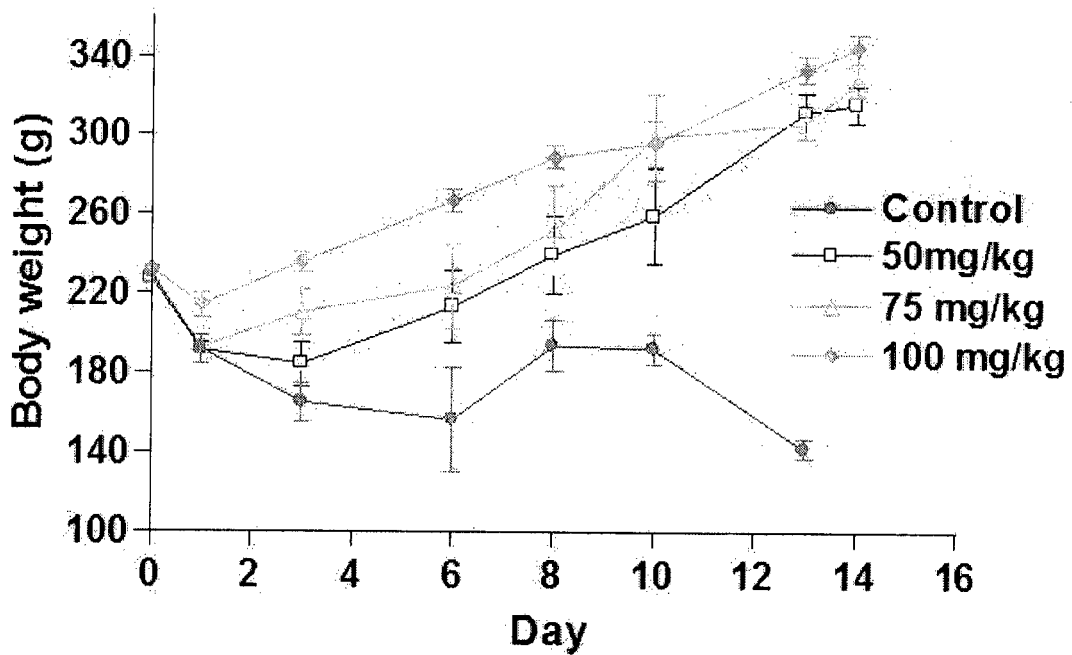
Figure 2:
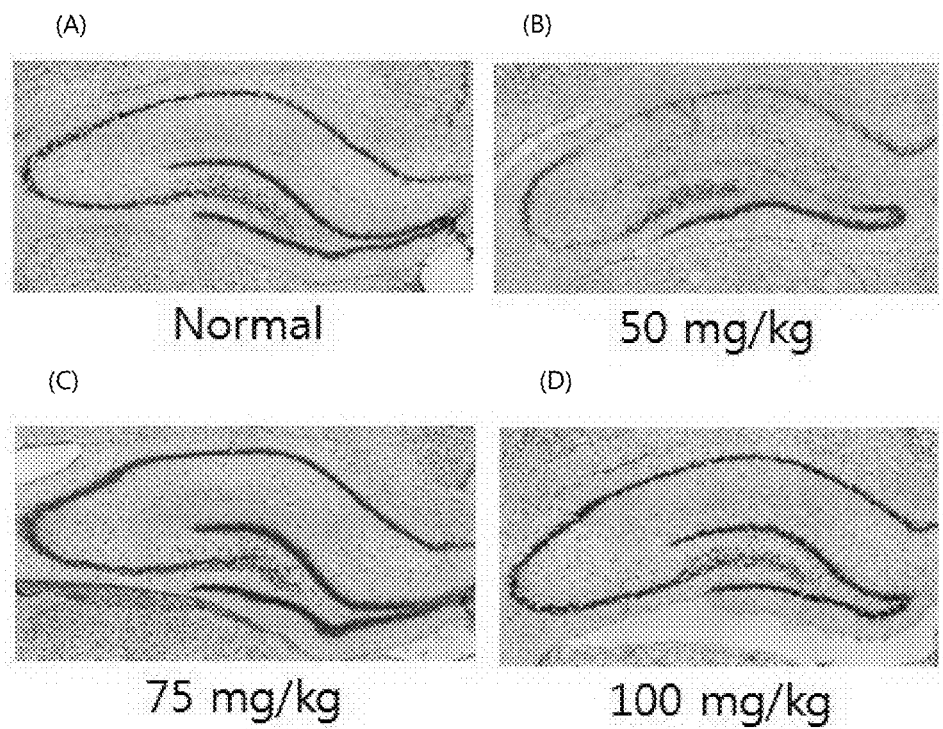
FIG. 2 represents the results of Rat's Brain Tissues (thionine stained coronal sections of the hippocampal formation (CA1, CA3, DG)) of neuroprotection activity of compound 1 after administration of Li-pilocarpine.
Figure 3:
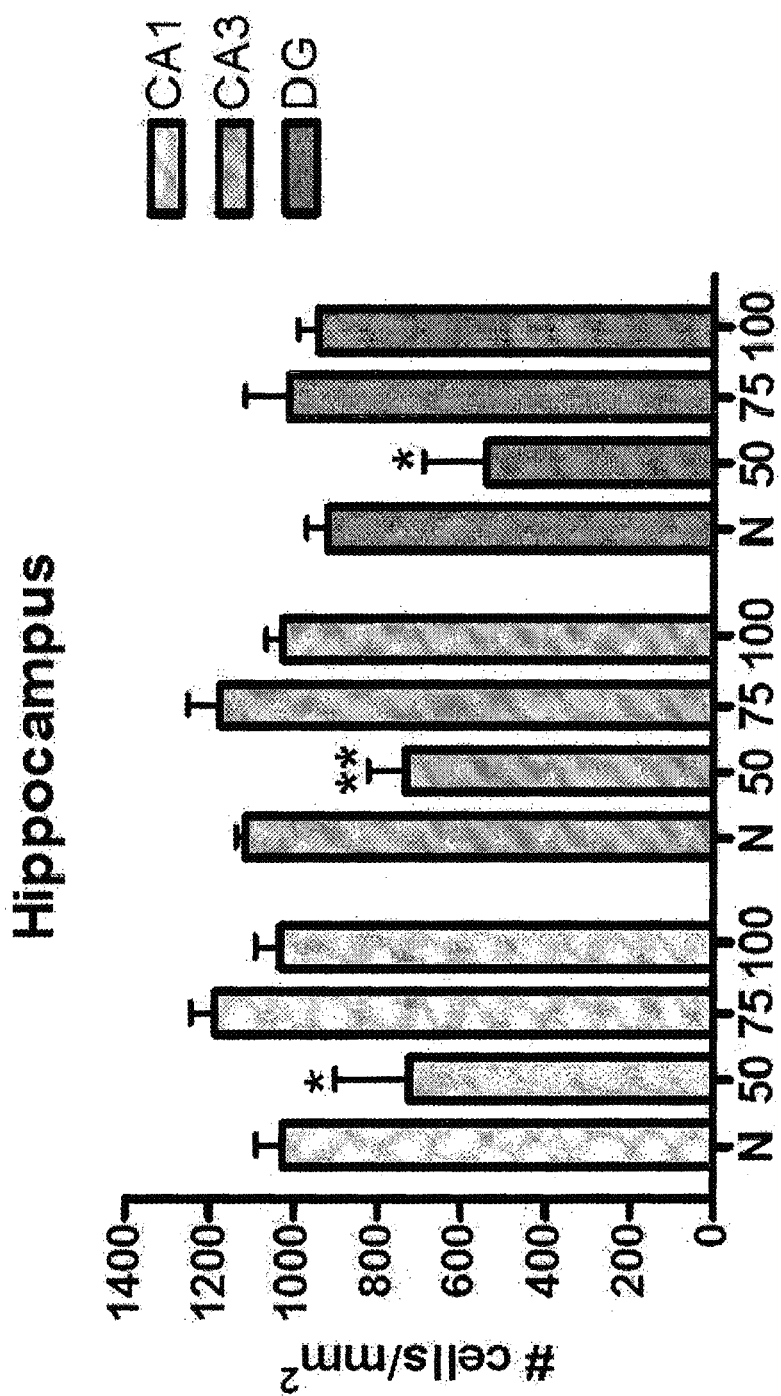
FIG. 3 represents the results of Rat's Brain Cell Density (dorsal hippocampus—CA1, CA3, DZ) of neuroprotection activity of compound 1 of 50 mg/kg, 75 mg/kg and 100 mg/kg. Data were represented as mean±SEM. Statistical analysis was performed by Two-way ANOVA followed by Bonferroni test as a post hoc analysis using Statistica, compared to Naïve group (N is normal).
Figure 4A:
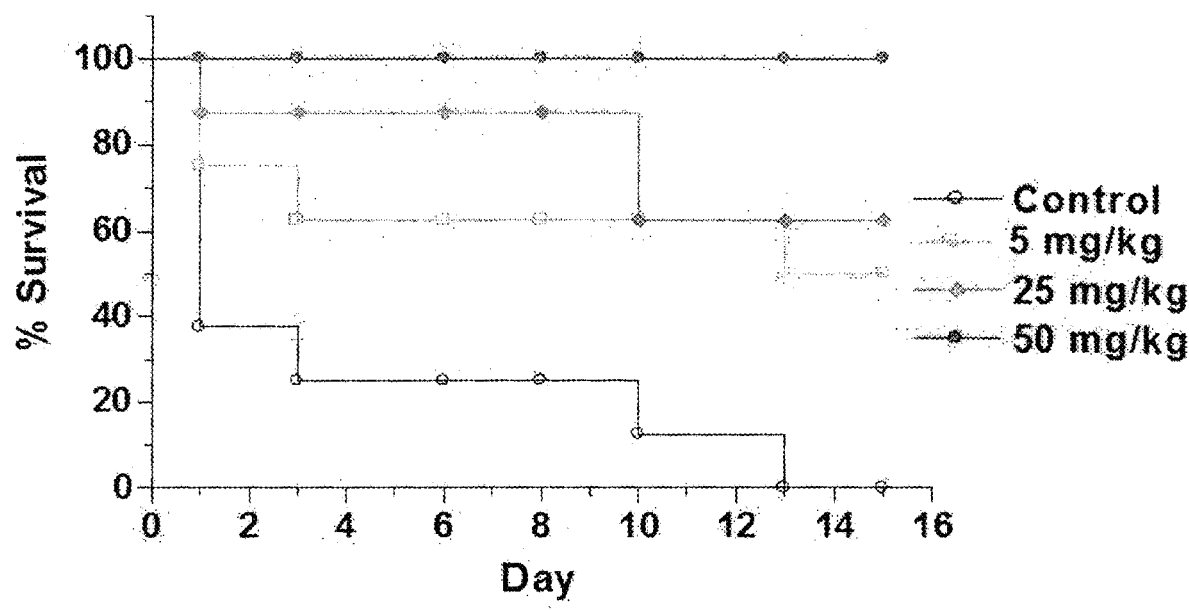
FIG. 4 shows the survival rate (FIG. 1a) and body weight change (FIG. 1b) of the rats treated with the compounds of the present invention, and the control rats were treated with vehicle after administration of Li-pilocarpine. The survival rate was 1-(2-iodophenyl)-(S)-1-hydroxypropyl-(S)-2-carbamate (compound 65) of 0% (Control), 50% (5 mg/kg), 62.5% (25 mg/kg), and 100% (50 mg/kg), respectively.
Figure 4B:
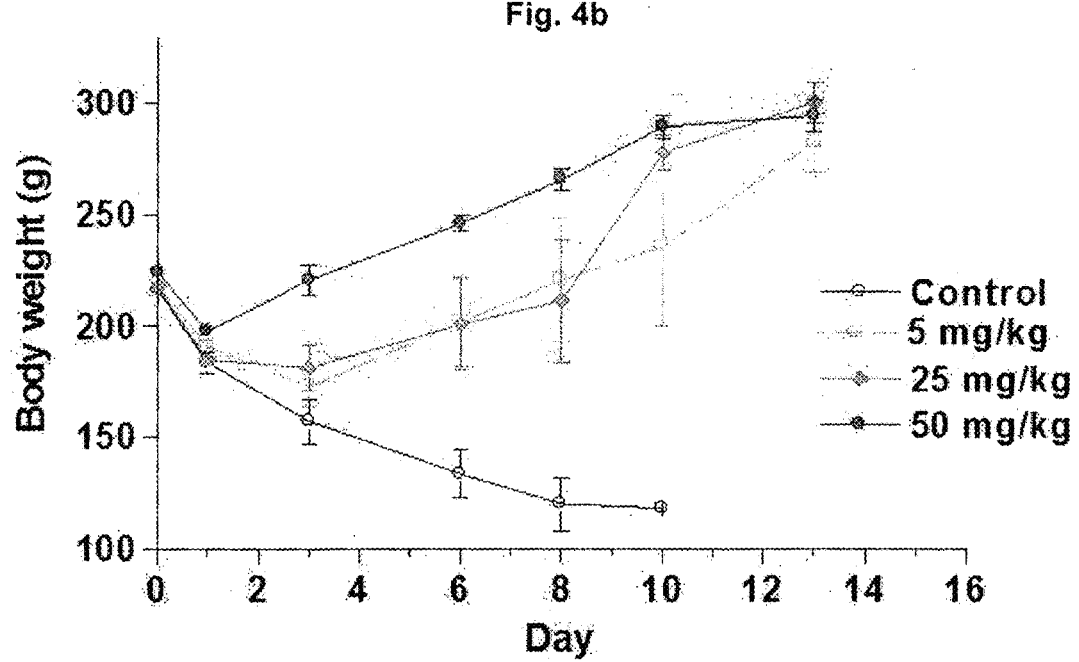
Figure 5A:
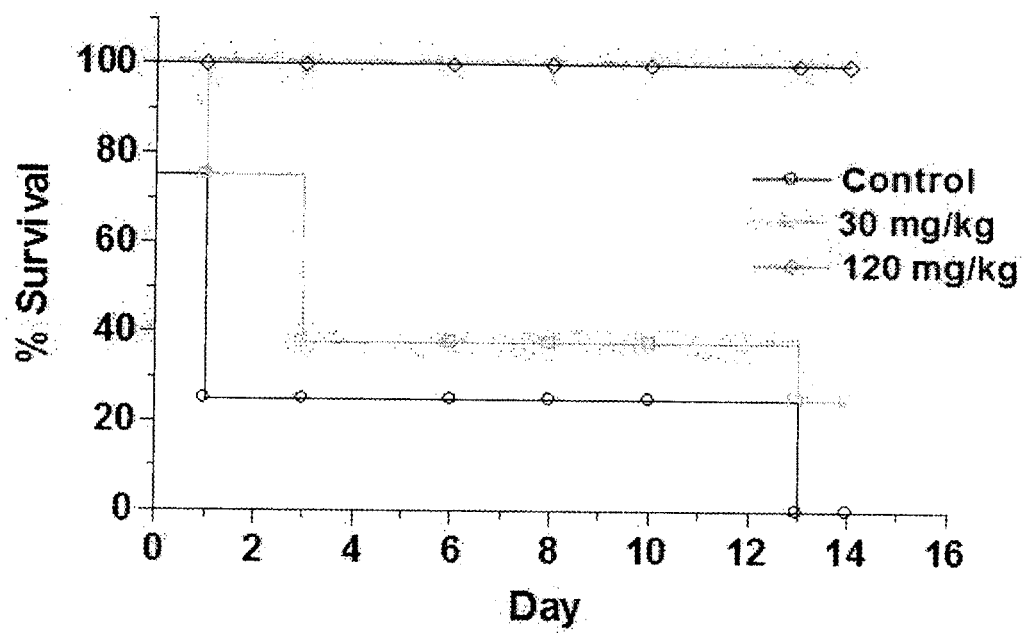
FIG. 5 represents the survival rate (FIG. 1a) and body weight change (FIG. 1b) of the rats treated with the compounds of the present invention, and the control rats were treated with vehicle after administration of Li-pilocarpine. The survival rate was 1-(2-iodophenyl)-(S)-1-hydroxybutyl-(S)-2-carbamate (compound 67) of 0% (Control), 25% (30 mg/kg), and 100% (120 mg/kg), respectively.
Figure 5B:
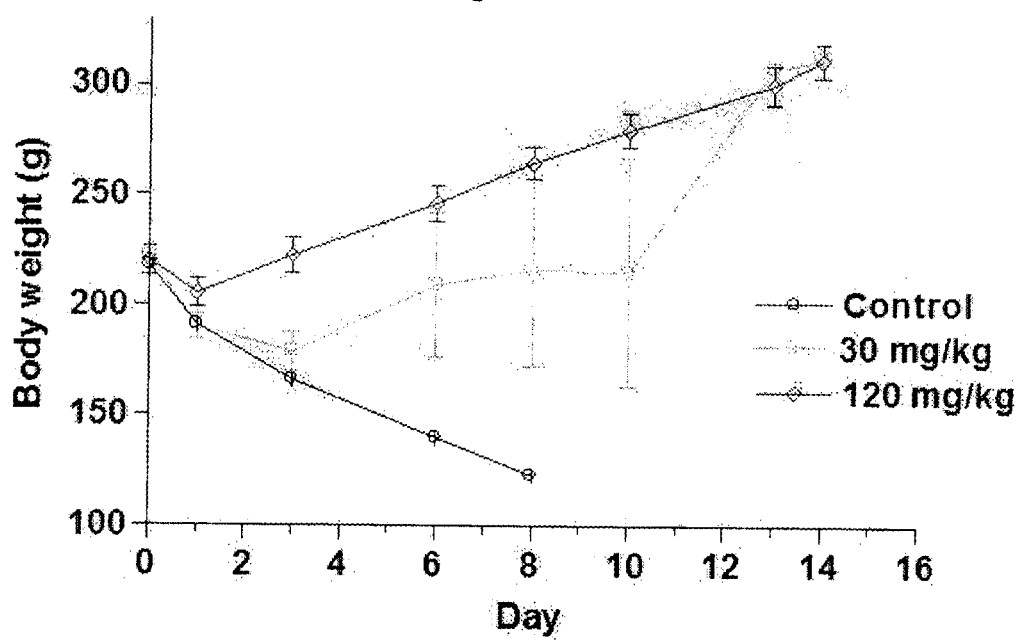
Figure 6:
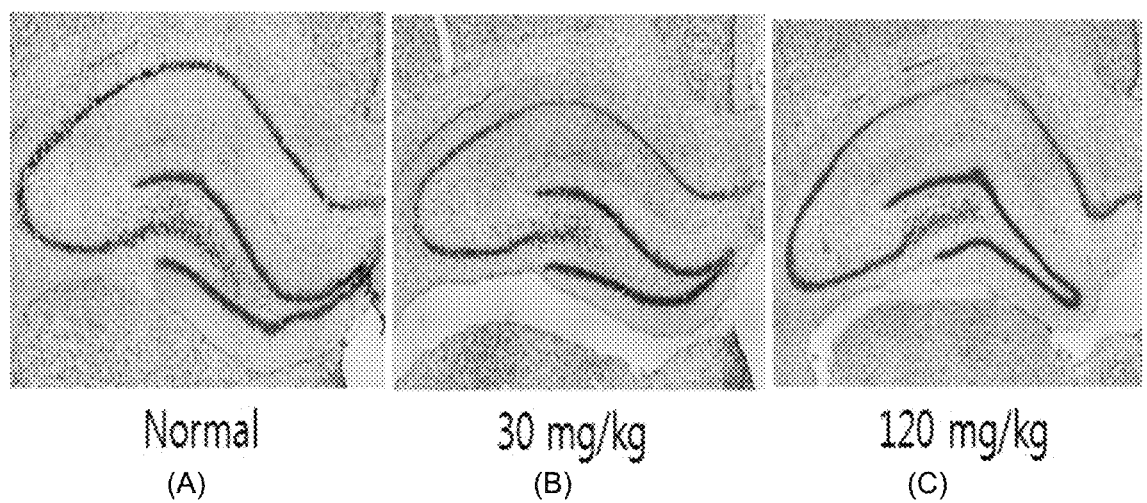
FIG. 6 shows the results of Rat's Brain Tissues (thionine stained coronal sections of the hippocampal formation (CA1, CA3, DG)) of neuroprotection activity of the 1-(2-iodophenyl)-(S)-1-hydroxybutyl-(S)-2-carbamate (compound 67).
Figure 7:
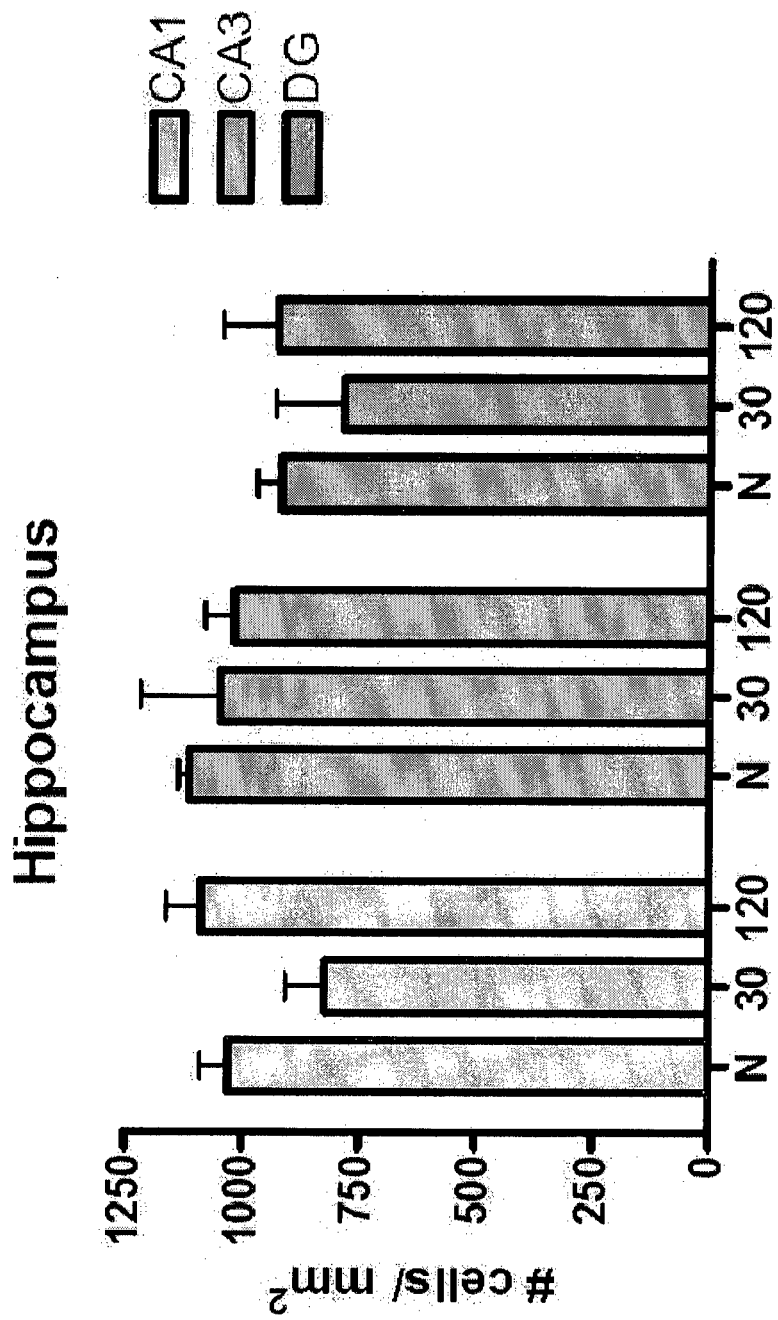
FIG. 7 represents the results of Rat's Brain Cell Density (dorsal hippocampus—CA1, CA3, DZ) of neuroprotection activity of 1-(2-iodophenyl)-(S)-1-hydroxybutyl-(S)-2-carbamate (compound 67) of 30 mg/kg and 120 mg/kg. Data were represented as mean±SEM. Statistical analysis was performed by Two-way ANOVA followed by Bonferroni test as a post hoc analysis using Statistica, compared to Naïve group (N is normal).
Figure 8:
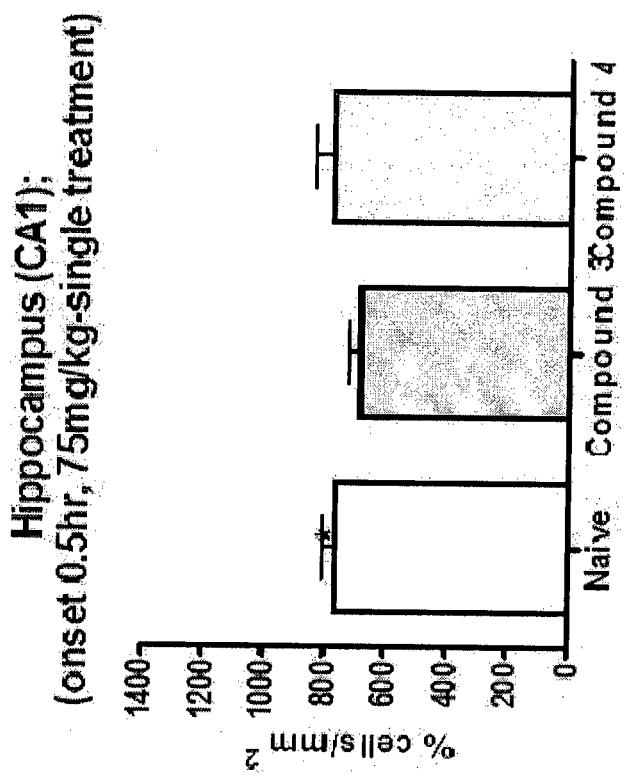
FIG. 8 represents the results of Rat's Brain Cell Density (dorsal hippocampus—CA1) of neuroprotection activity of compound 3 and 4 of 75 mg/kg, respectively. Naïve group (N) is normal.
Figure 9:
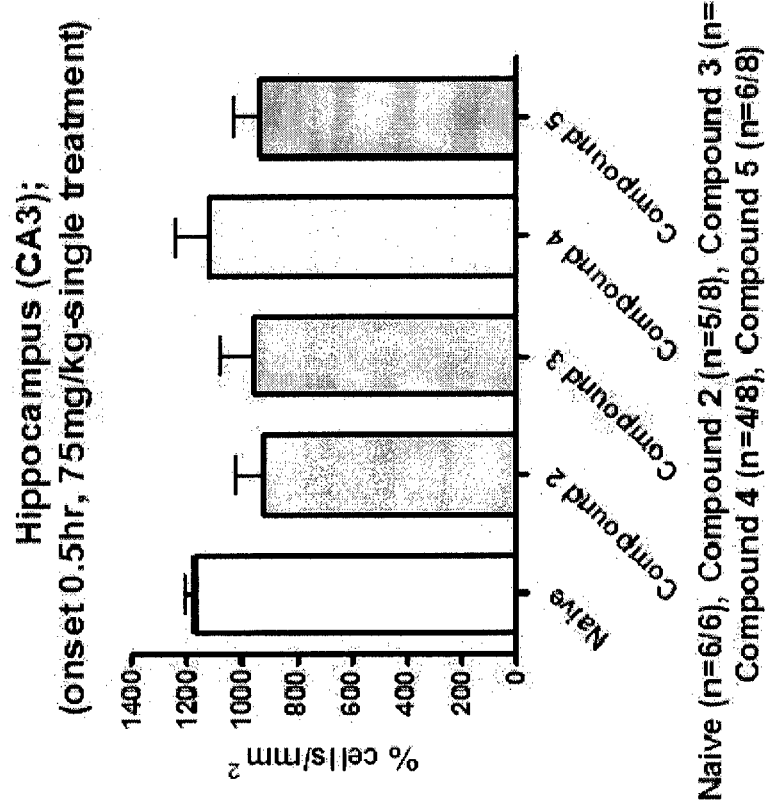
FIG. 9 represents the results of Rat's Brain Cell Density (dorsal hippocampus—CA3) of neuroprotection activity of compound 2, 3, 4 and 5 of 75 mg/kg, respectively. Naïve group (N) is normal.
Figure 10:
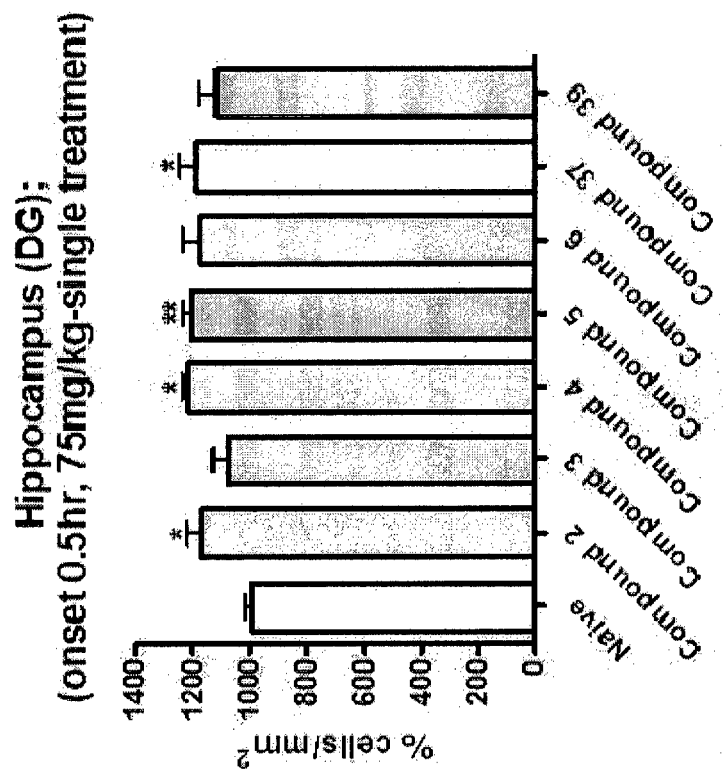
FIG. 10 represents the results of Rat's Brain Cell Density (dorsal hippocampus—DZ) of neuroprotection activity of compound 2, 3, 4, 5, 6, 37 and 39 of 75 mg/kg, respectively. Naïve group (N) is normal.

In one aspect of this invention, there is provided a composition for neuroprotection comprising a compound represented by the following formula 1 or pharmaceutically acceptable salt thereof as an active ingredient:

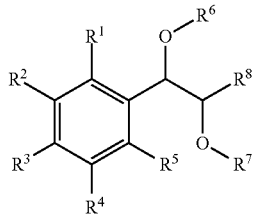

(1)

wherein $R^1$, $R^2$, $R^3$, $R^4$ and $R^5$ are each independently selected from the group consisting of hydrogen, and halogen; $R^6$ and $R^7$ are each independently hydrogen or

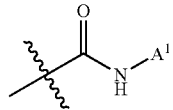

($A^1$ is selected from the group consisting of hydrogen, $C_1$-$C_5$ alkyl, $C_3$-$C_8$ cycloalkyl, $C_6$-$C_{10}$ aryl $C_1$-$C_3$ alkyl and bridged $C_6$-$C_8$ bicycloalkane) wherein one of $R^6$ and $R^7$ is hydrogen; and $R^8$ is $C_1$-$C_5$ alkyl.

The present inventor has made intensive studies to develop a novel agent with excellent neuroprotecting activity which may be applied to effective treatment for various disease associated with neurological injury. As results, the present inventors have discovered that the phenyl carbamate derivatives represented by above formula 1 provide highly enhanced neuroprotecting activity.

The term "neuroprotection" as used herein, refers to a preservation of neuronal structure and/or function and protection of neuronal structure and/or function against neurological diseases.

The term "neurological disease" as used herein, refers to a disease or disorder resulted from neurological injury caused by various pathogenesis such as neurodegeneration, neuro-vascular injury and genetic disorders; or disease or disorder inducing neurological injury.

As used herein, "neurological disease" is used interchangeably with "neurological injury".

The term "alkyl" as used herein, refers to a straight or branched chain of saturated hydrocarbon group, e.g., methyl, ethyl, propyl, butyl, isobutyl, tert butyl and pentyl. "$C_1$-$C_5$ alkyl group" as used herein, refers to an alkyl group with carbon number of 1-5.

The term "aryl" as used herein, refers to a totally or partially unsaturated monocyclic or polycyclic carbon rings having aromaticity. The aryl group of the present invention is preferably monoaryl or biaryl.

The term "bridged bicycloalkane" as used herein, refers to a cycloalkane containing two rings and two bridgehead carbon atoms shared by all three rings identifiable in the molecule.

According to a concrete embodiment, $R^1$, $R^2$, $R^3$, $R^4$ and $R^5$ are each independently selected from the group consisting of hydrogen, chlorine, fluorine and iodine. More concretely, $R^1$, $R^2$, $R^3$, $R^4$ and $R^5$ are not hydrogen at the same time.

According to a concrete embodiment, $R^6$ and $R^7$ are each independently hydrogen or

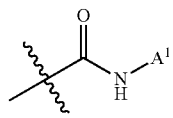

($A^1$ is selected from the group consisting of hydrogen, $C_1$-$C_4$ alkyl, cyclopropyl, cyclohexyl, phenyl $C_1$-$C_3$ alkyl and bicycloheptane).

According to a concrete embodiment, $R^6$ and $R^7$ are each independently hydrogen or

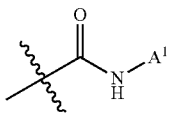

($A^1$ is selected from the group consisting of hydrogen, $C_1$-$C_4$ alkyl, cyclopropyl, cyclohexyl, benzyl and bicycle[2.2.1] heptane), and wherein one of $R^6$ and $R^7$ is hydrogen.

According to more concrete embodiment, the compound is selected from the group consisting of:

(1) 1-(2-chlorophenyl)-1-hydroxypropyl-2-carbamate;
(2) 1-(2-chlorophenyl)-1-hydroxybutyl-2-carbamate;
(3) 1-(2-chlorophenyl)-1-hydroxy-3-methyl-butyl-2-carbamate;
(4) 1-(2-chlorophenyl)-1-hydroxyhexyl-2-carbamate;
(5) 1-(2-chlorophenyl)-1-hydroxypropyl-2-N-methylcarbamate;
(6) 1-(2-chlorophenyl)-1-hydroxypropyl-2-N-propylcarbamate;
(7) 1-(2-chiorophenyl)-1-hydroxypropyl-2-N-isopropylcarbamate;
(8) 1-(2-chlorophenyl)-1-hydroxypropyl-2-N-cyclopropylcarbamate;
(9) 1-(2-chlorophenyl)-1-hydroxypropyl-2-N-cyclohexylcarbamate;
(10) 1-(2-chlorophenyl)-1-hydroxypropyl-2-N-benzylcarbamate;
(11) 1-(2-chiorophenyl)-1-hydroxypropyl-2-N-bicyclo[2,2,1]heptanecarbamate;
(12) 1-(2,4-dichlorophenyl)-1-hydroxypropyl-2-carbamate;
(13) 1-(2,6-dichlorophenyl)-1-hydroxypropyl-2-carbamate;
(14) 1-(2,4-dichlorophenyl)-1-hydroxybutyl-2-carbamate;
(15) 1-(2,6-dichlorophenyl)-1-hydroxybutyl-2-carbamat;
(16) 1-(2,4-dichlorophenyl)-1-hydroxy-3-methyl-butyl-2-carbamate;
(17) 1-(2,6-dichlorophenyl)-1-hydroxy-3-methyl-butyl-2-carbamate;
(18) 1-(2,4-dichlorophenyl)-1-hydroxyhexyl-2-carbamate;
(19) 1-(2,6-dichlorophenyl)-1-hydroxyhexyl-2-carbamate;
(20) 1-(2-chlorophenyl)-2-hydroxypropyl-1-carbamate;
(21) 1-(2-chlorophenyl)-2-hydroxypropyl-1-N-methylcarbamate;
(22) 1-(2-chlorophenyl)-2-hydroxypropyl-1-N-propylcarbamate;
(23) 1-(2-chlorophenyl)-2-hydroxypropyl-1-N-isopropylcarbamate;
(24) 1-(2-chlorophenyl)-2-hydroxypropyl-1-N-cyclopropylcarbamate;
(25) 1-(2-chlorophenyl)-2-hydroxypropyl-1-N-cyclohexylcarbamate;
(26) 1-(2-chiorophenyl)-2-hydroxypropyl-1-N-benzylcarbamate;
(27) 1-(2,4-dichlorophenyl)-2-hydroxypropyl-1-carbamate;
(28) 1-(2,6-dichlorophenyl)-2-hydroxypropyl-1-carbamate;
(29) 1-(2,4-dichlorophenyl)-2-hydroxybutyl-1-carbamate;
(30) 1-(2,6-dichlorophenyl)-2-hydroxybutyl-1-carbamate;
(31) 1-(2,4-dichlorophenyl)-2-hydroxy-3-methyl-butyl-1-carbamate;
(32) 1-(2,6-dichlorophenyl)-2-hydroxy-3-methyl-butyl-1-carbamate;
(33) 1-(2,4-dichlorophenyl)-2-hydroxyhexyl-1-carbamate;
(34) 1-(2,6-dichlorophenyl)-2-hydroxyhexyl-1-carbamate;
(35) 1-(2-fluorophenyl)-1-hydroxypropyl-2-carbamate;
(36) 1-(2-iodophenyl)-1-hydroxypropyl-2-carbamate;
(37) 1-(2-iodophenyl)-1-hydroxybutyl-2-carbamate;
(38) 1-(2,3-dichlorophenyl)-1-hydroxypropyl-2-carbamate; and
(39) 1-(2,3-dichlorophenyl)-2-hydroxypropyl-1-carbamate.

According to even more concrete embodiment, the compound is selected from the group consisting of:

(1) 1-(2-chlorophenyl)-1-hydroxypropyl-2-carbamate;
(2) 1-(2-chlorophenyl)-1-hydroxybutyl-2-carbamate;
(3) 1-(2-chlorophenyl)-1-hydroxy-3-methyl-butyl-2-carbamate;
(5) 1-(2-chlorophenyl)-1-hydroxypropyl-2-N-methylcarbamate;
(8) 1-(2-chlorophenyl)-1-hydroxypropyl-2-N-cyclopropylcarbamate;
(12) 1-(2,4-dichlorophenyl)-1-hydroxypropyl-2-carbamate;
(13) 1-(2,6-dichlorophenyl)-1-hydroxypropyl-2-carbamate;
(17) 1-(2,6-dichlorophenyl)-1-hydroxy-3-methyl-butyl-2-carbamate; and
(38) 1-(2,3-dichlorophenyl)-1-hydroxypropyl-2-carbamate.

According to concrete embodiment, the compound is in the form of racemate, enantiomer, diastereomer, a mixture of enantiomer or a mixture of diastereomer.

In this compound, 2 chiral carbons exist at positions 1 and 2 from phenyl group; thus, the compound may exist in the form of an enantiomer, a diastereomer, a mixture of enantiomers, or a mixture of diastereomers, as well as a racemate.

According to more concrete embodiment, the racemate, enantiomer, diastereomer, mixture of enantiomer or mixture of diastereomer of the compound, above described is selected from the group consisting of:

1-(2-chlorophenyl)-(S)-1-hydroxypropyl-(S)-2-carbamate;

1-(2-chlorophenyl)-(R)-1-hydroxypropyl-(R)-2-carbamate;

racemate of 1-(2-chlorophenyl)-(S)-1-hydroxypropyl-(S)-2-carbamate and 1-(2-chiorophenyl)-(R)-1-hydroxypropyl-(R)-2-carbamate;

1-(2-chlorophenyl)-(R)-1-hydroxypropyl-(S)-2-carbamate;

1-(2-chlorophenyl)-(S)-1-hydroxypropyl-(R)-2-carbamate;

1-(2-chiorophenyl)-(S)-1-hydroxybutyl-(S)-2-carbamate;

racemate of 1-(2-chlorophenyl)-(S)-1-hydroxybutyl-(S)-2-carbamate and 1-(2-chlorophenyl)-(R)-1-hydroxybutyl-(R)-2-carbamate;

1-(2-chlorophenyl)-(S)-1-hydroxy-3-methyl-butyl-(S)-2-carbamate;

racemate of 1-(2-chlorophenyl)-(S)-1-hydroxy-3-methyl-buty-(S)-2-carbamate and 1-(2-chiorophenyl)-(R)-1-hydroxy-3-methyl-butyl-(R)-2-carbamate;

1-(2-chlorophenyl)-(S)-1-hydroxypropyl-(S)-2-N-methylcarbamate;

1-(2-chlorophenyl)-(S)-1-hydroxypropyl-(S)-2-N-propylcarbamate;

1-(2-chlorophenyl)-(S)-1-hydroxypropyl-(R)-2-N-isopropylcarbamate;

1-(2-chlorophenyl)-(S)-1-hydroxypropyl-(R)-2-N-cyclopropylcarbamate;

1-(2-chlorophenyl)-(S)-1-hydroxypropyl-(R)-2-N-cyclohexyl carbamate;

1-(2-chlorophenyl)-(R)-1-hydroxypropyl-(R)-2-N-methylcarbamate;

1-(2-chlorophenyl)-(R)-1-hydroxypropyl-(R)-2-N-propylcarbamate;

1-(2-chlorophenyl)-(R)-1-hydroxypropyl-(R)-2-N-isopropylcarbamate;

1-(2-chlorophenyl)-(R)-1-hydroxypropyl-(R)-2-N-cyclopropylcarbamate;

1-(2-chlorophenyl)-(R)-1-hydroxypropyl-(R)-2-N-cyclohexyl carbamate;

racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate;

racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate;

racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate;

racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate;

racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate;

1-(2-fluorophenyl)-(S)-1-hydroxypropyl-(S)-2-carbamate;

1-(2-fluorophenyl)-(R)-1-hydroxypropyl-(R)-2-carbamate;

1-(2-iodophenyl)-(S)-1-hydroxypropyl-(S)-2-carbamate;

1-(2-iodophenyl)-(R)-1-hydroxypropyl-(R)-2-carbamate; and 1-(2-iodophenyl)-(S)-1-hydroxybutyl-(S)-2-carbamate.

As seen in the Examples, the present inventors have synthesized the compounds of various stereochemistries, and investigated their neuroprotecting activity by multilateral experiments.

The term "enantiomer" as used herein, refers to one of two stereoisomers that are mirror images of each other which are non-superposable due to existence of one or more chiral carbons. According to a concrete embodiment, the enantiomer of the present invention is one in which chiral carbons of C1 and C2 are diverse in stereo-configuration.

The term "diastereomer" as used herein, refers to stereoisomers that are not enantiomers, which occurs when two or more stereoisomers of a compound have different configurations at one or more (but not all) of the equivalent chiral centers thus are not mirror images of each other.

The term "racemate" as used herein, refers to one that has equal amounts of two enantiomers of different stereo-configuration, and lack in optical activity.

It would be obvious to the skilled artisan from the Examples below that the compounds of this invention are not limited to those with specific stereochemistry.

According to concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethane sulfonate, benzene sulfonate and toluene sulfonate; metal salts by reaction with an alkali metal such as sodium and potassium; or salts with ammonium ion.

In one aspect of this invention, there is provided a composition for preventing or treating a neurological disease comprising the composition according to claim 1, wherein the neurological disease is selected from the group consisting of neurodegenerative disease, autism spectrum disease and prion diseases.

According to concrete embodiment, the composition according to formula 1, wherein the neurological disease is selected from the group consisting of neurodegenerative disease, autism spectrum disease and prion diseases.

According to more concrete embodiment, the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia.

According to more concrete embodiment, the autism spectrum disease is selected from the group consisting of autism, Asperger syndrome and pervasive developmental disorder not otherwise specified (PDD-NOS).

According to more concrete embodiment, the prion diseases is selected from the group consisting of Creutzfeldt-Jakob disease, Gerstmann-Sträussler-Scheinker disease, Kuru disease and fatal familial insomnia.

In another aspect of this invention, there is provided a method for providing neuroprotection comprising administering a pharmaceutically effective amount of the composition of the present invention to a subject in need thereof.

In still another aspect of this invention, there is provided a method for preventing or treating a neurological disease comprising administering a pharmaceutically effective amount of the composition of the present invention to a subject in need thereof, wherein the neurological disease is selected from the group consisting of neurodegenerative disease, autism spectrum disease and prion diseases.

As the common descriptions regarding the compounds of this invention are mentioned above, they are omitted herein to avoid excessive overlaps.

According to the present invention, the present inventor has observed that administration of the compound of the present invention significantly increased neuronal density of epilepsy rat brain, suggesting that the compound of the present invention may be used for effective anti-neurodegeneration agent.

The composition of this invention may be provided as a pharmaceutical composition comprising a pharmaceutically effective amount of the compound or pharmaceutically acceptable salt thereof.

The term "pharmaceutically effective amount" as used herein, refers to an amount enough to show and accomplish efficacies and activities for neuroprotection.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The present invention will now be described in further detail by examples. It would be obvious to those skilled in the art that these examples are intended to be more concretely illustrative and the scope of the present invention as set forth in the appended claims is not limited to or by the examples.

EXAMPLES

[Reaction Formula I Synthesis of Diol-1]

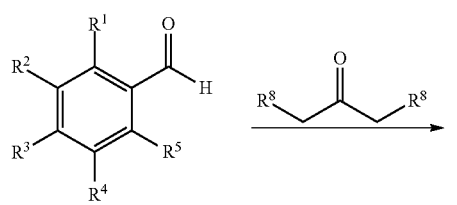

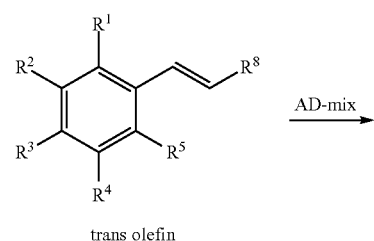

trans olefin

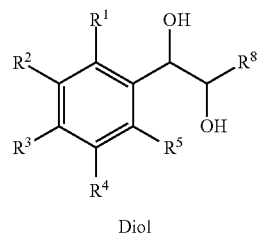

Diol

A diol compound used in the synthesis of the carbamate compound may be synthesized by dihydroxylation of a trans-olefin compound. A diol compound having optical activity may be synthesized using a sharpless asymmetric dihydroxylation catalyst.

[Reaction Formula II Synthesis of Diol-2]

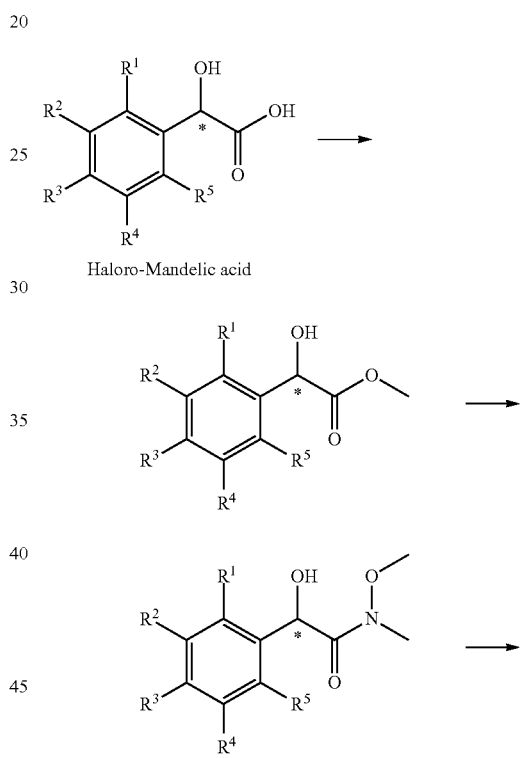

Haloro-Mandelic acid

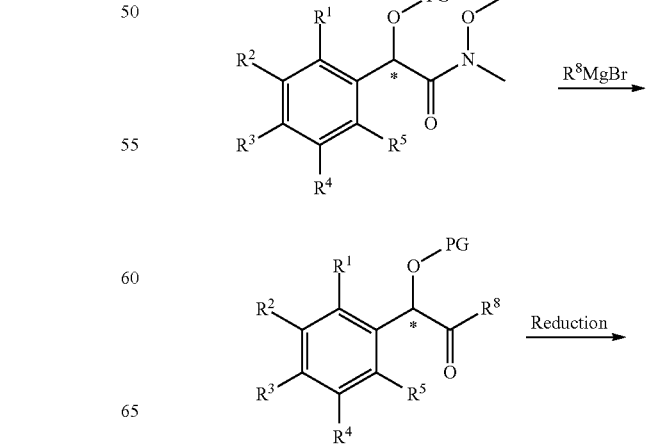

-continued

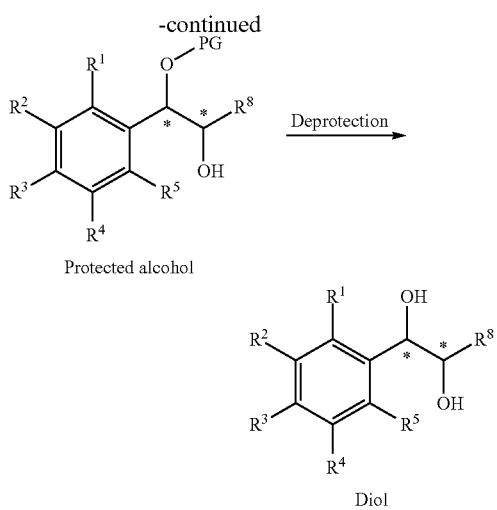

Protected alcohol

PG = Protecting Group

Diol

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic $C_1$-$C_4$ alkyl groups, and each aryl group may be independently selected from the group consisting of $C_5$-$C_8$ aryl groups, preferably a phenyl group.

[Reaction Formula III Carbamation Reaction-1]

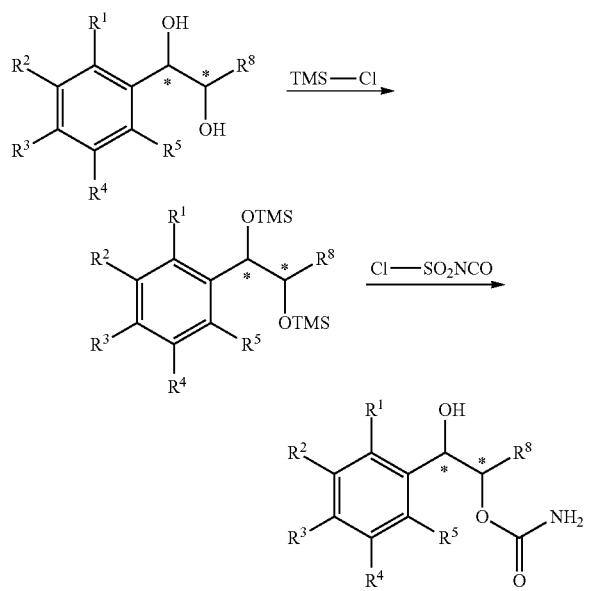

A highly selectivity form of regioisomer of single carbamate of diol having halogen substituent at phenyl ring is prepared (Example 1~14 and 36~67 are synthesized by reaction formula III).

[Reaction Formula IV Carbamation Reaction-2]

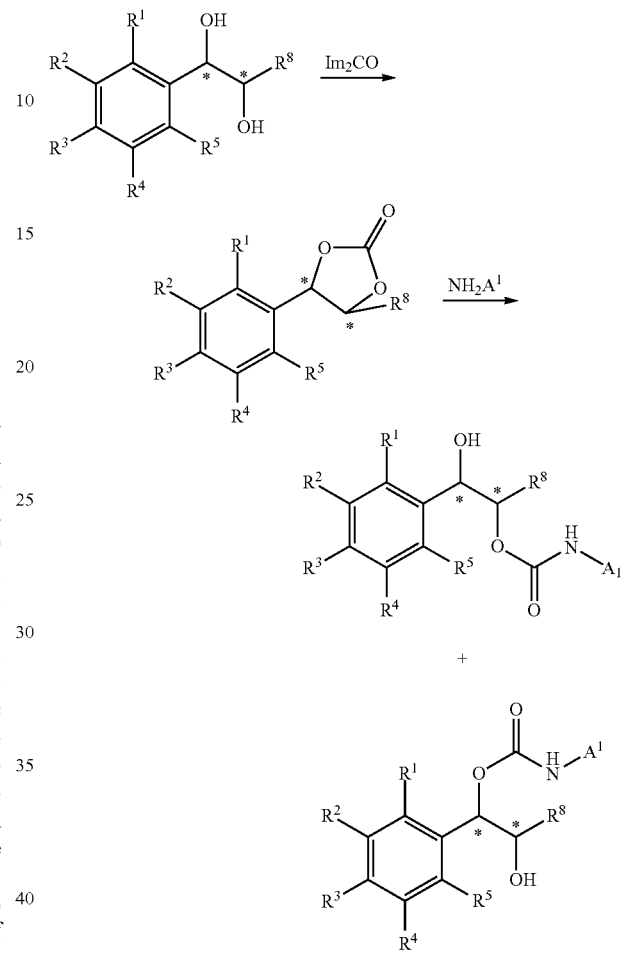

Two substances in the form of regioisomers of a single carbamate of diol having halogen substituent at phenyl ring may be separated by flash column chromatography to obtain two kinds of single carbamate compounds. (Example 15~35 and 68~15 are synthesized by reaction formula IV)

[Reaction Formula V Protection Reaction]

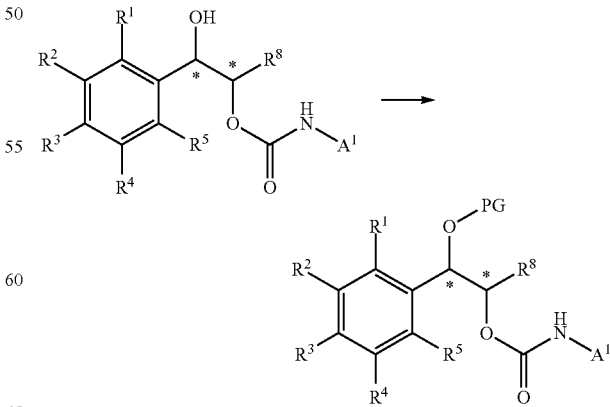

In the Reaction Formula V, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluorenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic $C_1$-$C_4$ alkyl groups, and each aryl group may be independently selected from the group consisting of $C_5$-$C_8$ aryl groups, preferably a phenyl group.

In the Reaction Formula IV and V, $A^1$ is selected from the group consisting of hydrogen, $C_1$-$C_5$ alkyl, $C_3$-$C_7$ cycloalkyl, $C_6$-$C_{10}$ aryl $C_1$-$C_3$ alkyl and bridged $C_6$-$C_8$ bicycloalkane. Two substances in the form of regioisomers of a single carbamate of diol having halogen substituent at phenyl ring may be separated by flash column chromatography to obtain two kinds of single carbamate compounds.

Preparation Example 1

Synthesis of 1-(2-chlorophenyl)-trans-1-propene

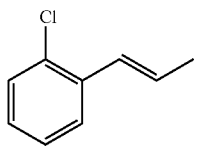

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%).

$^1$H NMR (400MHz, $CDCl_3$) δ1.94 (d, J=4.8Hz, 3H), 6.24 (m, 1H), 6.78 (d, J=14Hz, 1H), 7.11~7.51 (m, 4H)

Preparation Example 2

Synthesis of 1-(2-chlorophenyl)-trans-1-butene

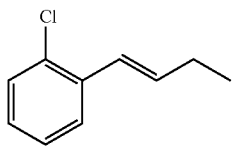

The substantially same method as described in Preparation Example 1 was conducted, except that 3-heptanone was used instead of 3-pentanone, to obtain the title compound (2.9 g, yield 83%).

$^1$H NMR (400MHz, $CDCl_3$) δ1.14 (d, J=7.6Hz, 3H), 2.29~2.33 (m, 2H), 6.28 (dt, J=16Hz, 6.4Hz, 1H), 6.78 (d, J=15.6Hz, 1H), 7.13~7.54 (m, 4H)

Preparation Example 3

Synthesis of 1-(2-chlorophenyl)-3-methyl-trans-1-butene

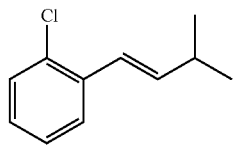

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400MHz, $CDCl_3$) δ1.14 (d, J=6.8Hz, 6H), 2.25~2.57 (m, 1H), 6.20 (dd, J=16Hz, 7.2Hz, 1H), 7.64 (d, J=16Hz, 1H), 7.12~7.54 (m, 4H)

Preparation Example 4

Synthesis of 1-(2-chlorophenyl)-trans-1-hexene

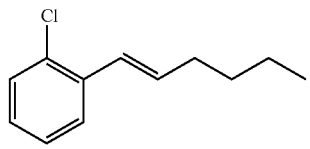

The substantially same method as described in Preparation Example 1 was conducted, except that 6-undecanone was used instead of 3-pentanone, to obtain the title compound (10 g, yield 85%).

$^1$H NMR (400MHz, $CDCl_3$) δ0.96 (t, J=7.2Hz, 3H), 1.33~1.56 (m, 4H), 2.26~2.32 (m, 4H), 6.24 (dt, J=15.6Hz, 7Hz, 1H), 6.78 (d, J=16Hz, 1H), 7.13~7.54 (m, 4H)

Preparation Example 5

Synthesis of 1-(2,4-dichlorophenyl)-trans-1-propene

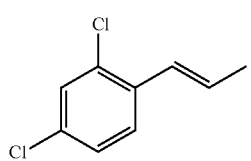

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400MHz, $CDCl_3$) δ1.95 (dd, J=6.8Hz, 1.6Hz, 3H), 6.24 (m, 1H), 6.72 (d, J=15.6Hz, 1H), 7.18~7.44 (m, 3H)

Preparation Example 6

Synthesis of 1-(2,4-dichlorophenyl)-trans-1-butene

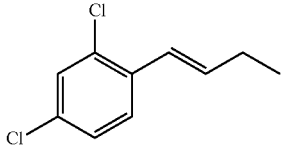

The substantially same method as described in Preparation Example 5 was conducted, except that 3-heptanone was used instead of 3-pentanone, to obtain the title compound (2.1 g, yield 90%).

$^1$H NMR (400MHz, CDCl$_3$) δ1.14 (d, J=7.6Hz, 3H), 2.20~2.33 (m, 2H), 6.26 (dt, J=16Hz, 6.8Hz, 1H), 6.70 (d, J=15.6Hz, 1H), 7.18~7.46 (m, 3H)

Preparation Example 7

Synthesis of 1-(2,6-dichlorophenyl)-3-methyl-trans-1-butene

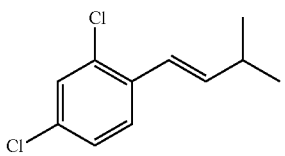

The substantially same method as described in Preparation Example 5 was conducted, except that 2,6-dimethylheptan-4-one was used instead of 3-pentanone, to obtain the title compound (0.23 g, yield 10~40%).

$^1$H NMR (400MHz, CDCl$_3$) δ1.15 (d, J=6.8Hz, 6H), 2.53~2.58 (m, 1H), 6.19 (dd, J=16.4Hz, 6.8Hz, 1H), 6.31 (d, J=16.4Hz, 1H), 7.18~7.46 (m, 3H)

Preparation Example 8

Synthesis of 1-(2,4-dichlorophenyl)-trans-1-hexene

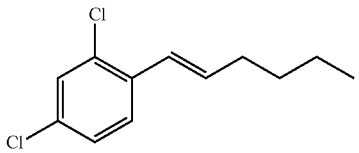

The substantially same method as described in Preparation Example 5 was conducted, except that 6-undecanone was used instead of 3-pentanone, to obtain the title compound (3.2 g, yield 40~80%).

$^1$H NMR (400MHz, CDCl$_3$) δ0.96 (t, J=7.2Hz, 3H), 1.38~1.52 (m, 4H), 2.25~2.31 (m, 2H), 6.22 (dt, J=15.6Hz, 6.8Hz, 1H), 6.70 (d, J=15.6Hz, 1H), 7.18~7.46 (m, 3H)

Preparation Example 9

Synthesis of 1-(2,6-dichlorophenyl)-trans-1-propene

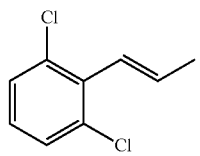

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR (400MHz, CDCl$_3$) δ1.98 (d, J=8Hz, 3H), 6.23~6.31 (m, 1H), 6.40 (d, J=16Hz, 1H), 7.05~7.32 (m, 3H)

Preparation Example 10

Synthesis of 1-(2,6-dichlorophenyl)-trans-1-butene

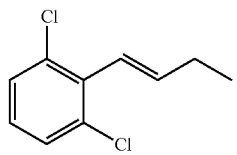

The substantially same method as described in Preparation Example 9 was conducted, except that 3-heptanone was used instead of 3-pentanone, to obtain the title compound (1.2 g, yield 10~40%).

$^1$H NMR (400MHz, CDCl$_3$) δ1.17 (t, J=7.6Hz, 3H), 2.30~2.37 (m, 2H), 6.29 (dt, J=16.4Hz, 6Hz, 1H), 6.37(d, J=16.4Hz, 1H), 7.05~7.32 (m, 3H)

Preparation Example 11

Synthesis of 1-(2,6-dichlorophenyl)-3-methyl-trans-1-butene

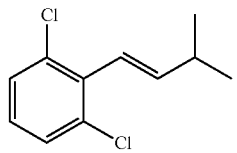

The substantially same method as described in Preparation Example 9 was conducted, except that 2,6-dimethylheptan-4-one was used instead of 3-pentanone, to obtain the title compound (0.23 g, yield 10~40%).

$^1$H NMR (400MHz, CDCl$_3$) δ1.15(d, J=6.8Hz, 6H), 2.53~2.58(m, 1H), 6.19(dd, J=16.4Hz, 6.8Hz, 1H), 6.31(d, J=16.4Hz, 1H), 7.05~7.32(m, 3H)

Preparation Example 12

Synthesis of 1-(2,6-dichlorophenyl)-trans-1-hexene

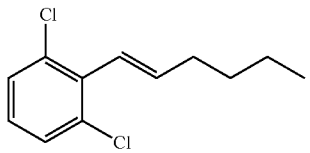

The substantially same method as described in Preparation Example 9 was conducted, except that 6-undecanone was used instead of 3-pentanone, to obtain the title compound (0.2 g, yield 10~40%).

$^1$H NMR (400MHz, CDCl$_3$) δ0.99 (t, J=7.2Hz, 3H), 1.14~1.59 (m, 4H), 2.30~2.36 (m, 2H), 6.24 (dt, J=16Hz, 6.6Hz, 1H), 6.38 (d, J=16.4Hz, 1H), 7.05~7.33 (m, 3H)

Preparation Example 13

Synthesis of 1-(2,3-dichlorophenyl)-trans-1-propene

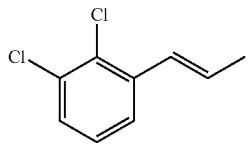

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR (400MHz, CDCl$_3$) δ1.94 (d, J=4.8Hz, 3H), 6.24 (m, 1H), 6.78 (d, J=14Hz, 1H), 7.11~7.51 (m, 3H)

Preparation Example 14

Synthesis of 1-(2-chlorophenyl)-(S,S)-1,2-propanediol

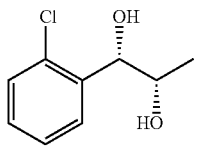

1-(2-chlorophenyl)-trans-1-propene (1.5 g, Preparation Example 1) was dissolved in 30 mL of the mixture of t-BuOH/H$_2$O (1:1(V/V)). At 0° C., AD-mix-a (Aldrich, U.S.A.) (13.7 g) and methane sulfone amide (CH$_3$SO$_2$NH$_2$, 0.76 g, 0.0080 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (1.65 g, yield 90%).

$^1$H NMR (400MHz, CDCl$_3$) δ1.20 (d, J=6.4Hz, 3H), 2.48 (d, J=4.0Hz 1H), 2.92 (d, J=4.4Hz, 1H), 3.93~3.97 (m, 1H), 4.97 (t, J=4.8Hz, 1H), 7.22~7.51 (m, 4H)

$^{13}$C NMR (100MHz, CDCl$_3$) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

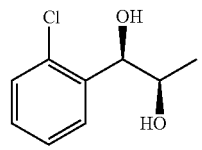

1-(2-chlorophenyl)-trans-1-propene (2.5 g, Preparation Example 1) was dissolved in 50 mL of the mixture of t-BuOH/H$_2$O (1:1(V/V)). At 0° C., AD-mix-a (Aldrich, U.S.A.) (23.5 g) and methane sulfone amide (CH$_3$SO$_2$NH$_2$, 1.27 g, 0.013 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (2.96 g, yield 90%).

$^1$H NMR (400MHz, CDCl$_3$) δ1.20(d, J=6.4Hz, 3H), 2.48 (d, J=4.0Hz, 1H, 2.92 (d, J=4.4Hz, 1H), 3.93~3.97(m, 1H), 4.97(t, J=4.8Hz, 1H), 7.22~7.51(m, 4H)

Preparation Example 16

Synthesis of the mixture of 1-(2-chlorophenyl)-(S,S)-1,2-propanediol and 1-(2-chlorophenyl)-(R,R)-1,2-propanediol

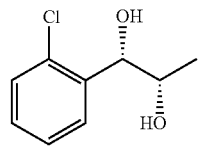 & 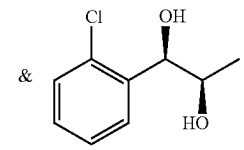

1-(2-chlorophenyl)-trans-1-propene (6.53 g, Preparation Example 1) was dissolved in 45 mL of the mixture of acetone/t-BuOH/H$_2$O(5:1:1 V/V). At the room temperature, N-methylmorpholine-N-oxide (7.51 g) and OsO$_4$ (0.54 g) were added thereto and stirred for 2-3 hours. When the reaction was completed, the obtained product was washed with water and methylenechloride (MC). Then, the organic layer was dehydrated with anhydrous magnesium sulfate (MgSO$_4$), filtrated, and concentrated under reduced pressure. The concentrated residue was purified by a silica gel column chromatography to produce the title compound (6.42 g, yield 80%).

$^1$H NMR (400MHz, CDCl$_3$) δ1.20 (d, J=6.4Hz, 3H), 2.48 (d, J=4.0Hz, 1H), 2.92 (d, J=4.4Hz, 1H), 3.93~3.97 (m, 1H), 4.97 (t, J=4.8Hz, 1H), 7.22~7.51 (m, 4H)

Preparation Example 17

Synthesis of 1-(2-chlorophenyl)-(S,S)-1,2-butanediol

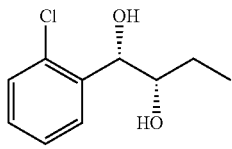

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

$^1$H NMR (400MHz, CDCl$_3$) δ1.01 (t, J=7.4Hz, 3H), 1.52~1.65 (m, 2H), 2.01 (d, J=4.4Hz, 1H), 2.74 (d, J=5.2Hz, 1H), 3.69~3.75 (m, 1H), 5.05 (t, J=5.0Hz, 1H), 7.23~7.54 (m, 4H)

Preparation Example 18

Synthesis of 1-(2-chlorophenyl)-(R,R)-1,2-butanediol

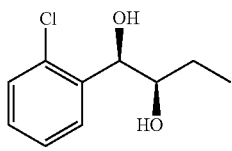

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR (400MHz, CDCl$_3$) δ1.01 (t, J=7.4Hz, 3H), 1.52~1.65(m, 2H), 2.01(d, J=4.4Hz, 1H), 2.74(d, J=5.2Hz, 1H), 3.69~3.75(m, 1H), 5.05(t, J=5.0Hz, 1H), 7.23~7.54(m, 4H)

Preparation Example 19

Synthesis of the mixture of 1-(2-chlorophenyl)-(S,S)-1,2-butanediol and 1-(2-chlorophenyl)-(R,R)-1,2-butanediol

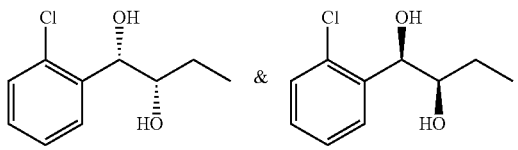

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR (400MHz, CDCl$_3$) δ1.01(t, J=7.4Hz, 3H), 1.52~1.65 (m, 2H), 2.01 (d, J=4.4Hz, 1H), 2.74 (d, J=5.2Hz, 1H), 3.69~3.75 (m, 1H), 5.05 (t, J=5.0Hz, 1H), 7.23~7.54 (m, 4H)

Preparation Example 20

Synthesis of 1-(2-chlorophenyl)-3-methyl-(S,S)-1,2-butanediol

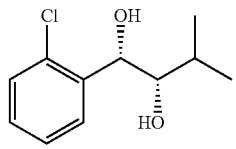

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR (400MHz, CDCl$_3$) δ1.07(t, J=7.2Hz, 6H), 1.83~1.89 (m, 1H), 1.92 (d, J=5.6Hz, 1H), 2.69 (d, J=6.4Hz, 1H), 3.53~3.56 (m, 1H), 5.22~5.25 (m, 1H), 7.23~7.55 (m, 4H)

Preparation Example 21

Synthesis of 1-(2-chlorophenyl)-3-methyl-(R,R)-1,2-butanediol

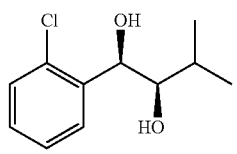

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR (400MHz, CDCl$_3$) δ1.07 (t, J=7.2Hz, 6H), 1.82~1.90 (m, 1H), 1.93 (d, J=5.6Hz, 1H), 2.79 (d, J=6Hz, 1H), 3.53~3.57 (m, 1H), 5.23~5.25 (m, 1H), 7.23~7.54 (m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

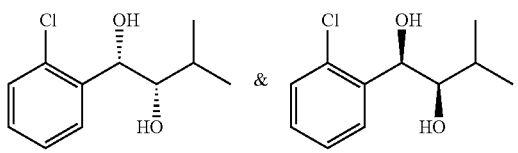

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

$^1$H NMR (400MHz, CDCl$_3$) δ1.07 (t, J=7.2Hz, 6H), 1.83~1.90 (m, 1H), 1.92 (d, J=5.6Hz, 1H), 2.69 (d, J=6.4Hz, 1H), 3.53~3.56 (m, 1H), 5.22~5.25 (m, 1H), 7.23~7.55 (m, 4H)

Preparation Example 23

Synthesis of 1-(2-chlorophenyl)-(S,S)-1,2-hexanediol

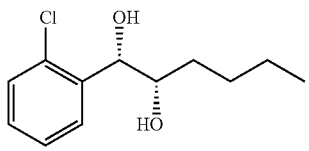

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

$^1$H NMR (400MHz, CDCl$_3$) δ0.90 (t, J=7.2Hz, 3H), 1.35~1.65 (m, 6H), 2.08 (d, J=4.4Hz, 1H), 2.71 (d, J=5.2Hz, 1H), 3.78~3.83 (m, 1H), 5.04 (t, J=5.0Hz, 1H), 7.23~7.53 (m, 4H)

Preparation Example 24

Synthesis of 1-(2-chlorophenyl)-(R,R)-1,2-hexanediol

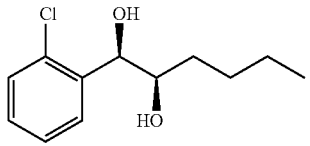

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).

$^1$H NMR (400MHz, CDCl$_3$) δ0.91 (t, J=6.6Hz, 3H), 1.35~1.65 (m, 6H), 2.08 (d, J=4.8Hz, 1H), 2.70 (d, J=5.2Hz, 1H), 3.80~3.83 (m, 1H), 5.05 (t, J=5.0Hz, 1H), 7.24~7.56 (m, 4H)

Preparation Example 25

Synthesis of the mixture of 1-(2-chlorophenyl)-(S,S)-1,2-hexanediol and 1-(2-chlorophenyl)-(R,R)-1,2-hexanediol

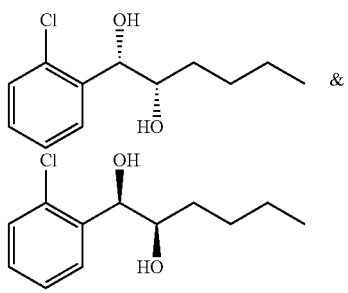

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

$^1$H NMR (400MHz, CDCl$_3$) δ0.90 (t, J=7.2Hz, 3H), 1.26~1.55 (m, 6H), 2.08 (d, J=4.4Hz, 1H), 2.71 (d, J=5.6Hz, 1H), 3.78~3.84 (m, 1H), 5.04 (t, J=3.2Hz, 1H), 7.24~7.55 (m, 4H)

Preparation Example 26

Synthesis of 1-(2,4-dichlorophenyl)-(S,S)-1,2-propanediol

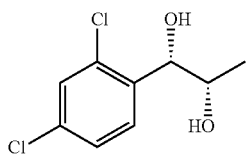

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

$^1$H NMR (400MHz, CDCl$_3$) δ1.22 (d, J=6.4Hz, 3H), 2.10 (d, J=4.4Hz, 1H), 2.71 (d, J=4.8Hz, 1H), 3.90~3.95 (m, 1H), 4.94 (t, J=5.0Hz, 1H), 7.31 (dd, J=2.0Hz, J=8.0Hz, 1H), 7.40 (d, J=2.0Hz, 1H), 7.49 (d, J=8.4Hz, 1H)

Preparation Example 27

Synthesis of
1-(2,4-dichlorophenyl)-(R,R)-1,2-propanediol

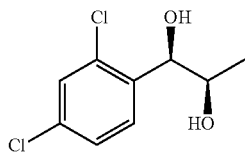

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).
$^1$H NMR (400MHz, CDCl$_3$) δ1.22 (d, J=6.4Hz, 3H), 2.10 (d, J=4.4Hz, 1H), 2.71 (d, J=4.8Hz, 1H), 3.90~3.95 (m, 1H), 4.94 (t, J=5.0Hz, 1H), 7.31~7.49 (m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

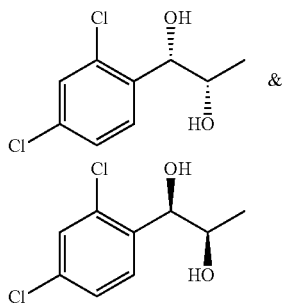

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).
$^1$H NMR (400MHz, CDCl$_3$) δ1.22 (d, J=6.4Hz, 3H), 2.10 (d, J=4.4Hz, 1H), 2.71 (d, J=4.8Hz, 1H), 3.90~3.95 (m, 1H), 4.94 (t, J=5.0Hz, 1H), 7.31~7.49 (m, 3H)

Preparation Example 29

Synthesis of
1-(2,4-dichlorophenyl)-(S,S)-1,2-butanediol

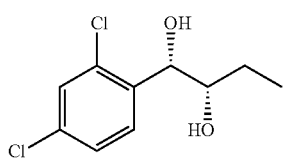

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).
$^1$H NMR (400MHz, CDCl$_3$) δ1.02 (t, J=7.4Hz, 3H), 1.54~1.61 (m, 2H), 2.07 (d, J=4.8Hz, 1H), 2.74 (d, J=4.8Hz, 1H), 3.65~3.68 (m, 1H), 5.01 (t, J=5.0Hz, 1H), 7.31~7.49 (m, 3H)

Preparation Example 30

Synthesis of
1-(2,4-dichlorophenyl)-(R,R)-1,2-butanediol

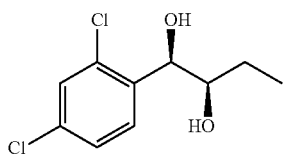

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).
$^1$H NMR (400MHz, CDCl$_3$) δ1.02 (t, J=7.4Hz, 3H), 1.54~1.61 (m, 2H), 2.07 (d, J=4.8Hz, 1H), 2.74 (d, J=4.8Hz, 1H), 3.65~3.68 (m, 1H), 5.01 (t, J=5.0Hz, 1H), 7.31~7.49 (m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

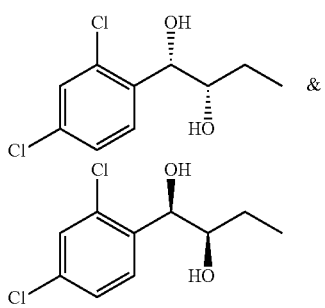

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).
$^1$H NMR (400MHz, CDCl$_3$) δ1.02 (t, J=7.4Hz, 3H), 1.54~1.61 (m, 2H), 2.07 (d, J=4.8Hz, 1H), 2.74 (d, J=4.8Hz, 1H), 3.65~3.68 (m, 1H), 5.01 (t, J=5.0Hz, 1H), 77.31~7.49 (m, 3H)

Preparation Example 32

Synthesis of 1-(2,4-dichlorophenyl)-3-methyl-(S,S)-1,2-butanediol

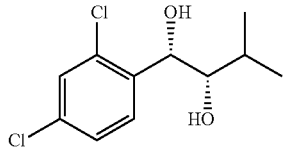

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 33

Synthesis of 1-(2,4-dichlorophenyl)-3-methyl-(R,R)-1,2-butanediol

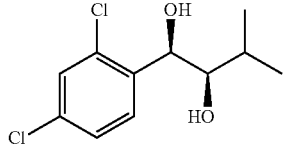

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

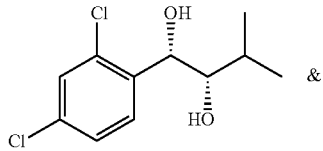

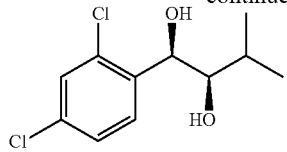

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 35

Synthesis of 1-(2,4-dichlorophenyl)-(S,S)-1,2-hexanediol

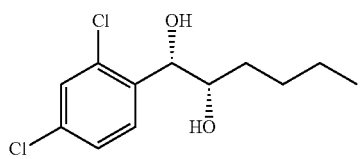 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

$^1$H NMR (400MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2Hz, 1H), 2.74 (d, J=5.2Hz, 1H), 3.72~3.77 (m, 1H), 4.98 (t, J=4.8Hz, 1H), 7.28~7.50 (m, 3H)

Preparation Example 36

Synthesis of 1-(2,4-dichlorophenyl)-(R,R)-1,2-hexanediol

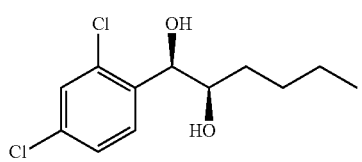 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

¹H NMR (400MHz, CDCl₃) δ0.89~0.93 (m, 3H), 1.30~1.39 (m, 2H), 1.49~1.52 (m, 2H), 1.56~1.62 (m, 2H), 2.05 (d, J=5.2Hz, 1H), 2.74 (d, J=5.2Hz, 1H), 3.72~3.77 (m, 1H), 4.98 (t, J=4.8Hz, 1H), 7.28~7.50 (m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

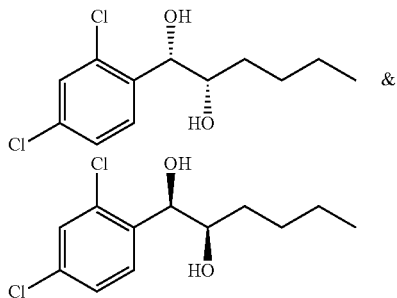

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).

¹H NMR (400MHz, CDCl₃) δ0.89~0.93 (m, 3H), 1.30~1.39 (m, 2H), 1.49~1.52 (m, 2H), 1.56~1.62 (m, 2H), 2.05 (d, J=5.2Hz, 1H), 2.74 (d, J=5.2Hz, 1H), 3.72~3.77 (m, 1H), 4.98 (t, J=4.8Hz, 1H), 7.28~7.50 (m, 3H)

Preparation Example 38

Synthesis of 1-(2,6-dichlorophenyl)-(S,S)-1,2-propanediol

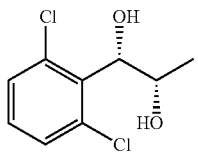

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

¹H NMR (400MHz, CDCl₃) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~7.36 (m, 3H)

Preparation Example 39

Synthesis of 1-(2,6-dichlorophenyl)-(R,R)-1,2-propanediol

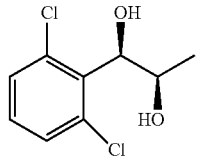

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

¹H NMR (400MHz, CDCl₃) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~7.36 (m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

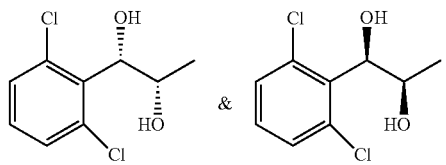

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

¹H NMR (400MHz, CDCl₃) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~7.36 (m, 3H)

Preparation Example 41

Synthesis of 1-(2,6-dichlorophenyl)-(S,S)-1,2-butanediol

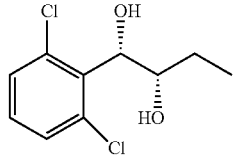

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR (400MHz, CDCl$_3$) δ0.97 (t, J=7.6Hz, 3H), 1.26~1.53 (m, 2H), 2.64 (dd, J=0.8Hz, J=4.0Hz, 1H), 3.14 (d, J=8.4Hz, 1H), 4.22~4.26 (m, 1H), 5.26 (t, J=8.4Hz, 1H), 7.17~7.35 (m, 3H)

Preparation Example 42

Synthesis of 1-(2,6-dichlorophenyl)-(R,R)-1,2-butanediol

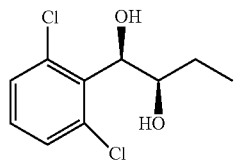

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR (400MHz, CDCl$_3$) δ0.97 (t, J=7.6Hz, 3H), 1.26~1.53 (m, 2H), 2.64 (dd, J=0.8Hz, J=4.0Hz, 1H), 3.14 (d, J=8.4Hz, 1H), 4.22~4.26 (m, 1H), 5.26 (t, J=8.4Hz, 1H), 7.17~7.35 (m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

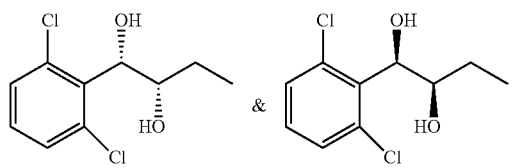

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR (400MHz, CDCl$_3$) δ0.97 (t, J=7.6Hz, 3H), 1.26~1.53 (m, 2H), 2.64 (dd, J=0.8Hz, J=4.0Hz, 1H), 3.14 (d, J=8.4Hz, 1H), 4.22~4.26 (m, 1H), 5.26 (t, J=8.4Hz, 1H), 7.17~7.35 (m, 3H)

Preparation Example 44

Synthesis of 1-(2,6-dichlorophenyl)-3-methyl-(S,S)-1,2-butanediol

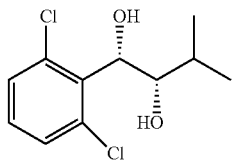

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 45

Synthesis of 1-(2,6-dichlorophenyl)-3-methyl-(R,R)-1,2-butanediol

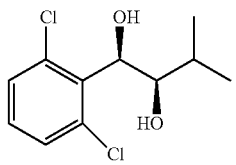

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

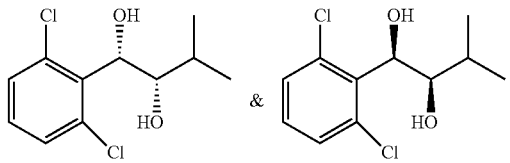

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR (400MHz, CDCl$_3$) δ1.00 (d, J=6.8Hz, 6H), 1.60~1.65 (m, 1H), 2.35 (d, J=4.0Hz, 1H), 3.12 (d, J=8.4Hz, 1H), 4.13~4.18 (m, 1H), 5.36 (t, J=7.6Hz, 1H), 7.17~7.35 (m, 3H)

Preparation Example 47

Synthesis of 1-(2,6-dichlorophenyl)-(S,S)-1,2-hexanediol

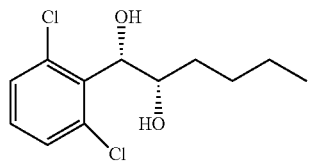 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR (400MHz, CDCl$_3$) δ0.85 (t, J=6.8Hz, 3H), 1.20~1.31 (m, 4H), 1.45~1.53 (m, 2H), 2.61~2.62 (m, 1H), 3.12 (d, J=8.4Hz, 1H), 4.28~4.33 (m, 1H), 5.25 (t, J=8.4Hz, 1H), 7.18~7.35 (m, 3H)

Preparation Example 48

Synthesis of 1-(2,6-dichlorophenyl)-(R,R)-1,2-hexanediol

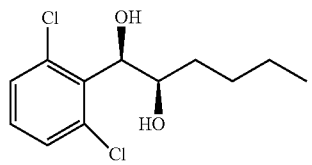 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR (400MHz, CDCl$_3$) δ0.85 (t, J=6.8Hz, 3H), 1.20~1.31 (m, 4H), 1.45~1.53 (m, 2H), 2.61~2.62 (m, 1H), 3.12 (d, j=8.4Hz, 1H), 4.28~4.33 (m, 1H), 5.25 (t, J=8.4Hz, 1H), 7.18~7.35 (m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

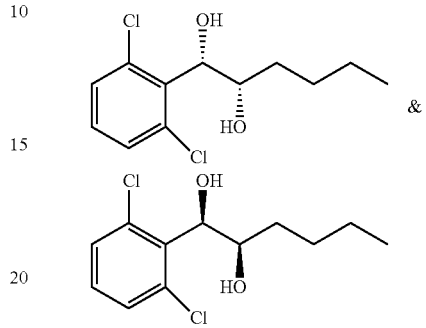

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR (400MHz, CDCl$_3$) δ0.85 (t, J=6.8Hz, 3H), 1.20~1.31 (m, 4H), 1.45~1.53 (m, 2H), 2.61~2.62 (m, 1H), 3.12 (d, J=8.4Hz, 1H), 4.28~4.33 (m, 1H), 5.25 (t, J=8.4Hz, 1H), 7.18~7.35 (m, 3H)

Preparation Example 50

Synthesis of methyl 2-(2-chlorophenyl)-(R)-2-hydroxyacetate

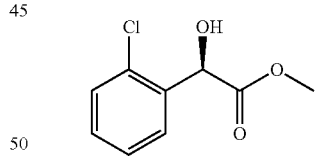

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR (400MHz, CDCl$_3$) δ 3.59 (d, J=5.2, 1H), 3.79 (t, J=6.0, 3H), 5.59 (d, J=5.2, 1H), 7.28~7.43 (m, 4H)

Preparation Example 51

Synthesis of 2-(2-chlorophenyl)-(R)-2-hydroxy-N-methoxy-N-methylacetamide

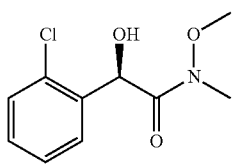

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate ($MgSO_4$), filtrated, and concentrated under reduced pressure. The concentrated residue was purified by a silica gel column chromatography to produce the title compound (14.68 g, yield 82%).

$^1$H NMR (400MHz, $CDCl_3$) δ3.23 (s, 3H), 3.28 (s, 3H), 4.33 (d, J=6.0Hz, 1H), 5.81 (d, J=5.6Hz, 1H), 7.23~7.42 (m, 4H)

Preparation Example 52

Synthesis of 2-(2-chlorophenyl)-N-methoxy-(R)-2-(t-butyl dimethlysiloxy)-N-methylacetamide

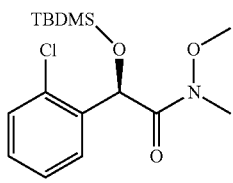

2-(2-chlorophenyl)-(R)-2-hydroxy-N-methoxy-N-methylacetamide (0.81 g, 3.52 mmol) obtained in Preparation Example 51 was dissolved in dichloromethane (DCM, and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with $H_2O$. The organic layer was separated and collected. The aqueous layer was extracted with $CH_2Cl_2$ (300 mL), dried over $MgSO_4$. Concentration under vacuum provided a title compound (0.97 g, 80~95%).

$^1$H NMR (400MHz, $CDCl_3$) δ−0.03(s, 3H), 0.14(s, 3H), 0.94(s, 9H), 2.97(s, 3H), 3.02(s, 3H), 5.83(s, 1H), 7.25~7.60 (m, 4H)

Preparation Example 53

Synthesis of 1-(2-chlorophenyl)-(R)-1-(t-butyldimethyl-siloxy) propane-2-on

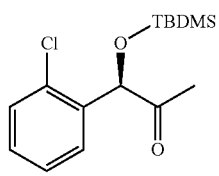

2-(2-chlorophenyl)-N-methoxy-(R)-2-(t-butyldimethylsiloxy)-N-methylacetamide (0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate ($KHSO_4$, 100 ml) and then, washed again with brine. The obtained organic layer was dehydrated with anhydrous magnesium sulfate ($MgSO_4$), filtrated, and concentrated under reduced pressure. The concentrated residue was purified by a silica gel column chromatography to produce the title compound (0.69 g, yield 85~95%).

$^1$H NMR (400MHz, $CDCl_3$) δ−0.3 (s, 3H), 0.14 (s, 3H), 0.94 (s, 9H), 2.18 (s, 3H), 5.50 (s, 1H), 7.27~7.56 (m, 4H)

Preparation Example 54

Synthesis of 1-(2-chlorophenyl)-(R)-1-(t-butyldimethyl-siloxy)-(S)-2-propanol

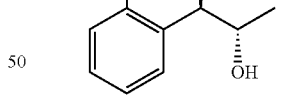

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride ($Zn(BH_4)_2$) was slowly added thereto and the obtained product was stirred. When the reaction was completed, the obtained product was washed by $H_2O$. The obtained organic layer was washed with $H_2O$, dehydrated with anhydrous magnesium sulfate ($MgSO_4$), filtrated, and concentrated under reduced pressure. The concentrated residue was purified by a silica gel column-chromatography to produce the title compound (0.04 g, yield 25~33%, cis:trans=2:1).

$^1$H NMR (400MHz, $CDCl_3$) δ−0.11 (s, 3H), 0.11 (s, 3H), 0.93 (S, 9H), 1.07 (d, J=6.4 3H), 2.05 (d, J=6.4 1H), 4.01~4.05 (m, 1H), 5.18 (d, J=4.0, 1H), 7.20~7.56 (m, 4H)

Preparation Example 55

Synthesis of
1-(2-chlorophenyl)-(R,S)-1,2-propanediol

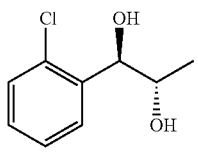

1-(2-chlorophenyl)-(R)-1-(t-butyldimethyl-siloxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concentrated under reduced pressure. The concentrated residue was purified by a silica gel column chromatography to produce the title compound (7.05 g, yield 60~90%).

$^1$H NMR (400MHz, CDCl$_3$) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56

Synthesis of
1-(2-chlorophenyl)-(S,R)-1,2-propanediol

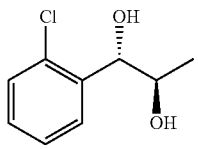

The substantially same method as described in Preparation Example 50~55 was conducted, except that (S)-2-chloromandelic acid was used instead of (R)-2-chloromandelic acid, to obtain the title compound (5.04 g, yield 84%).

$^1$H NMR (400MHz, CDCl$_3$) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57

Synthesis of
1-(2,3-dichlorophenyl)-(S,S)-1,2-propanediol

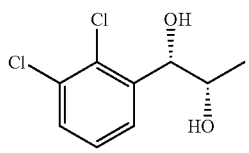

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

$^1$H NMR (400MHz, CDCl$_3$) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~ (m, 3H)

Preparation Example 58

Synthesis of
1-(2,3-dichlorophenyl)-(R,R)-1,2-propanediol

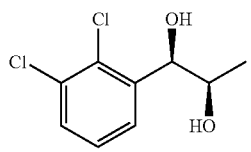

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

$^1$H NMR (400MHz, CDCl$_3$) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~ (m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

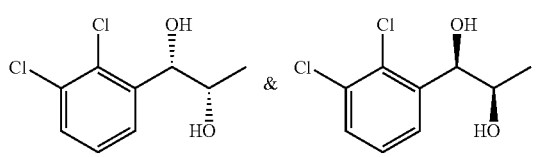

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

$^1$H NMR (400MHz, CDCl$_3$) δ1.10 (d, J=6.4Hz, 3H), 2.72 (d, J=2.4Hz, 1H), 3.10 (d, J=8.4Hz, 1H), 4.47~4.54 (m, 1H), 5.24 (t, J=8.8Hz, 1H), 7.18~(m, 3H)

Preparation Example 60

Synthesis of 1-(2-fluorophenyl)-trans-1-propene

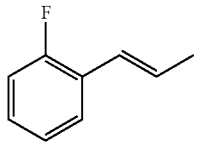

The substantially same method as described in Preparation Example 1 was conducted, except that 2-fluorobenzenaldehyde was used instead of 2-chlorobenzenealdehyde, to obtain the title compound (6.67 g, yield 61%).

$^1$H NMR (400MHz, CDCl$_3$) δ1.94 (d, J=6.8Hz, 3H), 6.30~6.38 (m, 1H), 6.57 (d, J=16Hz, 1H), 7.00~7.41 (m, 4H).

Preparation Example 61

Synthesis of 1-(2-fluorophenyl)-(S,S)-1,2-propanediol

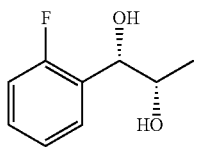

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

$^1$H NMR (400MHz, CDCl$_3$) δ1.15 (d, J=6.4Hz, 3H), 2.43 (d, J=3.6Hz, 1H), 2.69 (d, J=4.8Hz, 1H), 3.90~3.98 (m, 1H), 4.78 (dd, J=4.4, 7.2Hz, 1H), 7.04~7.50 (m, 4H)

Preparation Example 62

Synthesis of 1-(2-fluorophenyl)-(R,R)-1,2-propanediol

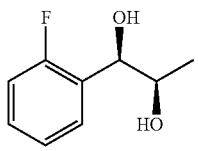

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

$^1$H NMR (400MHz, CDCl$_3$) δ1.15 (d, J=6.4Hz, 3H), 2.43 (d, J=3.6Hz, 1H), 2.69 (d, J=4.8Hz, 1H), 3.90~3.98 (m, 1H), 4.78 (dd, J=4.4, 7.2Hz, 1H), 7.04~7.50 (m, 4H)

Preparation Example 63

Synthesis of 2-iodobenzenealdehyde

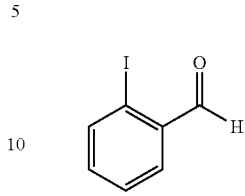

In a flask, 2-iodobenzyl alcohol (4 g, 17.09 mmol) was dissolved in dichloromethane (MC, 85 ml), and then, manganese oxide (MnO$_2$, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR (400MHz, CDCl$_3$) δ7.30~7.99 (m, 4H), 10.10 (s, 1H)

Preparation Example 64

Synthesis of 1-(2-iodophenyl)-trans-1-propene

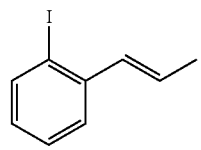

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR (400MHz, CDCl$_3$) δ1.95 (dd, J=6.8Hz, 1.6Hz, 3H), 6.09~6.18 (m, 1H), 6.60 (dd, J=15.66Hz, 1.8Hz, 1H), 6.89~7.84 (m, 4H)

Preparation Example 65

Synthesis of 1-(2-iodophenyl)-trans-1-butene

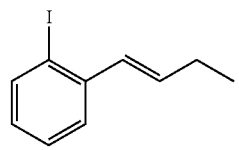

The substantially same method as described in Preparation Example 64 was conducted, except that 3-heptanone was used instead of 3-pentanone, to obtain the title compound (8.5 g, yield 75%).

$^1$H NMR (400MHz, CDCl$_3$) δ1.46 (t, J=7.6Hz, 3H), 2.26~2.34 (m, 2H), 6.17 (dt, J=15.6Hz, 6.6Hz 1H), 6.57 (d, J=15.6Hz, 1H), 6.89~7.85 (m, 4H)

Preparation Example 66

Synthesis of 1-(2-iodophenyl)-(S,S)-1,2-propanediol

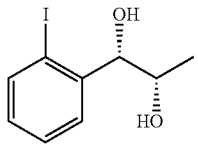

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400MHz, CDCl$_3$) δ1.27 (d, J=6.4Hz, 3H), 2.26 (br s, 1H), 2.74 (br s, 1H), 3.99 (t, J=6.0Hz, 1H), 4.81 (d, J=4.0Hz, 1H), 7.01~7.87 (m, 4H)

Preparation Example 67

Synthesis of 1-(2-iodorophenyl)-(R,R)-1,2-propanediol

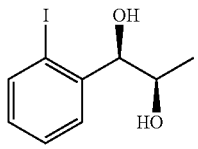

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR (400MHz, CDCl$_3$) δ1.26 (d, J=6.4Hz, 3H), 2.35 (br s, 1H), 2.85 (br d, J=4.0Hz, 1H), 3.98 (t, J=6.2Hz, 1H), 4.80 (dd, J=5.0, 4.4Hz, 1H), 7.00~7.87 (m, 4H)

Preparation Example 68

Synthesis of 1-(2-iodophenyl)-(S,S)-1,2-butanediol

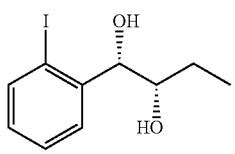

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR (400MHz, CDCl$_3$) δ1.04 (t, J=7.6Hz, 3H), 1.60~1.71 (m, 2H), 2.07 (br s, 1H), 2.74 (br s, 1H), 3.71~3.76 (m, 1H), 4.87 (d, J=4.8Hz, 1H), 7.01~7.87 (m, 4H)

Preparation Example 69

Preparation of 1-(2-chlorophenyl)-(S,S)-1,2-(Bis-trimethylsilanyloxy) propane

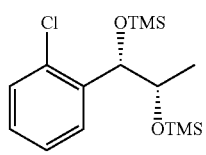

To a stirred solution of 1-(2-chlorophenyl)-(S,S)-1,2-propanediol (Preparation example 14, 67 g, 0.35 mol) in CH$_2$Cl$_2$ (670 ml) was added Et$_3$N (200 mL, 1.43 mol) and TMSCl (113.9 mL, 0.89 mol) at 0° C. under N$_2$. The reaction mixture was allowed to stir at 0° C. for 3 hr. The reaction mixture was quenched with H$_2$O (650 mL) at 0° C. The organic layer was separated and collected. The aqueous layer was extracted with CH$_2$Cl$_2$ (300 mL), dried over MgSO$_4$. Concentration under vacuum provided a crude product (104.18 g, 117.44%).

$^1$H NMR (400MHz, CDCl$_3$) δ−0.053 (s, 9H), 0.044 (s, 9H), 1.15(d, J=5.6Hz, 3H), 3.977~3.918 (m, 1H), 4.973 (d, J=6.4Hz, 1H), 7.207~7.165 (m, 1H), 7.321~7.245 (m, 2H), 7.566~7.543 (m, 1H)

Preparation Example 70

Preparation of 1-(2-chlorophenyl)-(R,R)-1,2-(Bis-trimethylsilanyloxy) propane

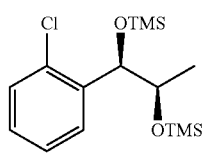

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

$^1$H NMR (400MHz, CDCl$_3$) δ−0.053 (s, 9H), 0.044 (s, 9H), 1.15 (d, J=5.6Hz, 3H), 3.977~3.918 (m, 1H), 4.973 (d, J=6.4Hz, 1H), 7.21~7.54 (m, 4H)

Preparation Example 71

Preparation of 1-(2-chlorophenyl)-1,2-(Bis-trimethylsilanyloxy) propane

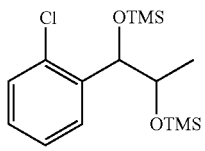

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).

$^1$H NMR (400MHz, CDCl$_3$) δ−0.053 (s, 9H), 0.044 (s, 9H), 1.15 (d, J=5.6Hz, 3H), 3.977~3.918 (m, 1H), 4.973 (d, J=6.4Hz, 1H), 7.21~7.54 (m, 4H)

Preparation Example 72

Preparation of 1-(2-chlorophenyl)-(S,R)-1,2-(Bis-trimethylsilanyloxy)propane

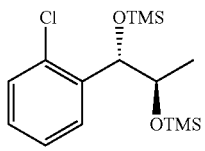

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).

$^1$H NMR (400MHz, CDCl$_3$) δ−0.053 (s, 9H), 0.044 (s, 9H), 1.15 (d, J=5.6Hz, 3H), 3.977~3.918 (m, 1H), 4.973 (d, J=6.4Hz, 1H), 7.21~7.54 (m, 4H)

Preparation Example 73

Preparation of 1-(2-chlorophenyl)-(R,S)-1,2-(Bis-trimethylsilanyloxy) propane

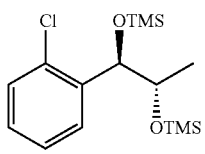

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).

$^1$H NMR (400MHz, CDCl$_3$) δ−0.053 (s, 9H), 0.044 (s, 9H), 1.15 (d, J=5.6Hz, 3H), 3.977~3.918 (m, 1H), 4.973 (d, J=6.4Hz, 1H), 7.21~7.54 (m, 4H)

Preparation Example 74

Preparation of 1-(2-chlorophenyl)-(S,S)-1,2-(Bis-trimethylsilanyloxy) butane

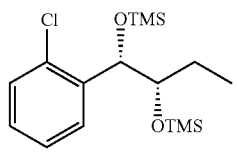

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).

$^1$H NMR (400MHz, CDCl$_3$) δ−0.053 (s, 9H), 0.044 (s, 9H), 1.01 (t, J=7.4Hz, 3H), 1.52~1.65 (m, 2H), 3.69~3.75 (m, 1H), 5.05 (t, J=5.0Hz, 1H), 7.23~7.54 (m, 4H)

Preparation Example 75

Preparation of 1-(2-chlorophenyl)-(R,R)-1,2-(Bis-trimethylsilanyloxy) butane

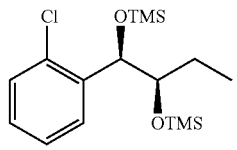

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).

$^1$H NMR (400MHz, CDCl$_3$) δ−0.053 (s, 9H), 0.044 (s, 9H), 1.01 (t, J=7.4Hz, 3H), 1.52~1.65 (m, 2H), 3.69~3.75 (m, 1H), 5.05 (t, J=5.0Hz, 1H), 7.23~7.54 (m, 4H)

Preparation Example 76

Preparation of 1-(2-chlorophenyl)-1,2-(Bis-trimethylsilanyloxy) butane

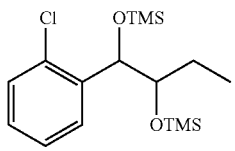

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).

$^1$H NMR (400MHz, CDCl$_3$) δ−0.053 (s, 9H), 0.044 (s, 9H), 1.01 (t, J=7.4Hz, 3H), 1.52~1.65 (m, 2H), 3.69~3.75 (m, 1H), 5.05 (t, J=5.0Hz, 1H), 7.23~7.54 (m, 4H)

Preparation Example 77

Preparation of 1-(2-chlorophenyl)-3-methyl-(S,S)-1,2-(Bis-trimethylsilanyloxy)-butane

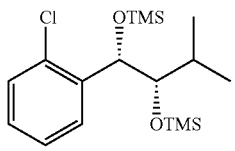

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%).

$^1$H NMR (400MHz, CDCl$_3$) δ−0.053 (s, 9H), 0.044 (s, 9H), 1.07 (t, J=7.2Hz, 6H), 1.83~1.89 (m, 1H), 3.53~3.56 (m, 1H), 5.22~5.25 (m, 1H), 7.23~7.55 (m, 4H)

Preparation Example 78

Preparation of 1-(2-chlorophenyl)-3-methyl-(R,R)-1,2-(Bis-trimethylsilanyloxy)-butane

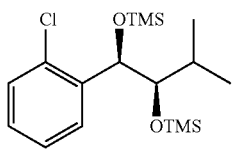

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

$^1$H NMR (400MHz, CDCl$_3$) δ−0.053 (s, 9H), 0.044 (s, 9H), 1.07 (t, J=7.2Hz, 6H), 1.83~1.89 (m, 1H), 3.53~3.56 (m, 1H), 5.22~5.25 (m, 1H), 7.23~7.55 (m, 4H)

Preparation Example 79

Preparation of 1-(2-chlorophenyl)-3-methyl-1,2-(Bis-trimethylsilanyloxy)-butane

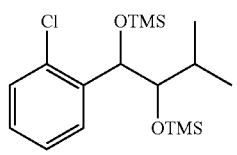

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).

$^1$H NMR (400MHz, CDCl$_3$) δ−0.053 (s, 9H), 0.044 (s, 9H), 1.07 (t, J=7.2Hz, 6H), 1.83~1.89 (m, 1H), 3.53~3.56 (m, 1H), 5.22~5.25 (m, 1H), 7.23~7.55 (m, 4H)

Preparation Example 80

Preparation of 1-(2-chlorophenyl)-(S,S)-1,2-(Bis-trimethylsilanyloxy)-hexane

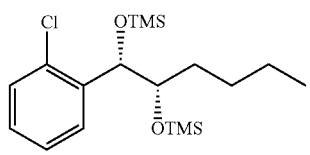

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).

$^1$H NMR (400MHz, CDCl$_3$) δ−0.053 (s, 9H), 0.044 (s, 9H), 0.90 (t, J=7.2Hz, 3H), 1.35~1.65 (m, 6H), 3.78~3.83 (m, 1H), 5.04 (t, J=5.0Hz, 1H), 7.23~7.53 (m, 4H)

Preparation Example 81

Preparation of 1-(2-chlorophenyl)-(S,S)-1,2-(Bis-trimethylsilanyloxy)-hexane

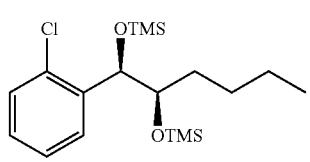

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).

$^1$H NMR (400MHz, CDCl$_3$) δ−0.053 (s, 9H), 0.044 (s, 9H), 0.90 (t, J=7.2Hz, 3H), 1.35~1.65 (m, 6H), 3.78~3.83 (m, 1H), 5.04 (t, J=5.0Hz, 1H), 7.23~7.53 (m, 4H)

Preparation Example 82

Preparation of 1-(2-chlorophenyl)-(S,S)-1,2-(Bis-trimethylsilanyloxy)-hexane

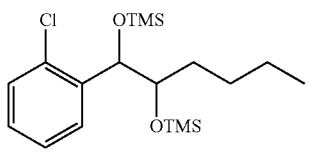

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).

$^1$H NMR (400MHz, CDCl$_3$) δ−0.053 (s, 9H), 0.044 (s, 9H), 0.90 (t, J=7.2Hz, 3H), 1.35~1.65 (m, 6H), 3.78~3.83 (m, 1H), 5.04 (t, J=5.0Hz, 1H), 7.23~7.53 (m, 4H)

Preparation Example 83

Preparation of 1-(2,4-dichlorophenyl)-(S,S)-1,2-(Bis-trimethylsilanyloxy)-propane

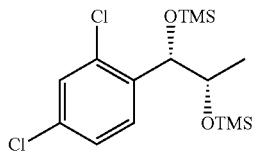

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).

$^1$H NMR (400MHz, CDCl$_3$) δ−0.053 (s, 9H), 0.044 (s, 9H), 1.22 (d, J=6.4Hz, 3H), 3.90~3.95 (m, 1H), 4.94 (t, J=5.0Hz, 1H), 7.31 (dd, J=2.0Hz, J=8.0Hz, 1H), 7.40 (d, J=2.0Hz, 1H), 7.49 (d, J=8.4Hz, 1H)

Preparation Example 84

Preparation of 1-(2,6-dichlorophenyl)-(S,S)-1,2-(Bis-trimethylsilanyloxy)-propane

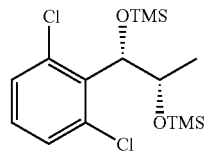

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

$^1$H NMR (400MHz, CDCl$_3$) δ−0.053 (s, 9H), 0.044 (s, 9H), 1.10 (d, J=6.4Hz, 3H), 4.47~4.54 (m, 1H), 5.24 (t, J=8.8Hz, 1H), 7.13~7.36 (m, 3H)

Preparation Example 85

Preparation of 1-(2,3-dichlorophenyl)-(S,S)-1,2-(Bis-trimethylsilanyloxy)-propane

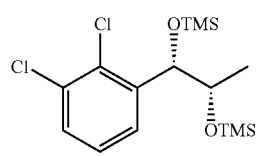

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

$^1$H NMR (400MHz, CDCl$_3$) δ−0.053 (s, 9H), 0.044 (s, 9H), 1.10 (d, J=6.4Hz, 3H), 4.47~4.54 (m, 1H), 5.24 (t, J=8.8Hz, 1H), 7.18~7.22 (m, 3H)

Preparation Example 86

Preparation of 1-(2,4-dichlorophenyl)-(S,S)-1,2-(Bis-trimethylsilanyloxy)-butane

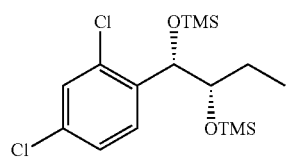

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

¹H NMR (400MHz, CDCl₃) δ−0.053 (s, 9H), 0.044 (s, 9H), 1.02 (t, J=7.4Hz, 3H), 1.54~1.61 (m, 2H), 3.65~3.68 (m, 1H), 5.01 (t, J=5.0Hz, 1H), 7.31~7.49 (m, 3H)

Preparation Example 87

Preparation of 1-(2,6-dichlorophenyl)-(S,S)-1,2-(Bis-trimethylsilanyloxy)-butane

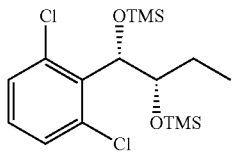

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

¹H NMR (400MHz, CDCl₃) δ−0.053 (s, 9H), 0.044(s, 9H), 0.97(t, J=7.6Hz, 3H), 1.26~1.53(m, 2H), 4.22~4.26(m, 1H), 5.26(t, J=8.4Hz, 1H), 7.17~7.35(m, 3H)

Preparation Example 88

Preparation of 1-(2,4-dichlorophenyl)-3-methyl-(S,S)-1,2-(Bis-trimethylsilanyloxy)-butane

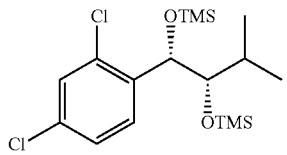

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

¹H NMR (400MHz, CDCl₃) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.30~7.53 (m, 3H)

Preparation Example 89

Preparation of 1-(2,6-dichlorophenyl)-3-methyl-(S,S)-1,2-(Bis-trimethylsilanyloxy)-butane

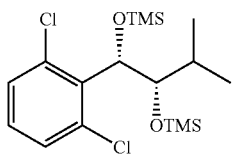

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

¹H NMR (400MHz, CDCl₃) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.17~7.35 (m, 3H)

Preparation Example 90

Preparation of 1-(2,4-dichlorophenyl)-(S,S)-1,2-(Bis-trimethylsilanyloxy)-hexane

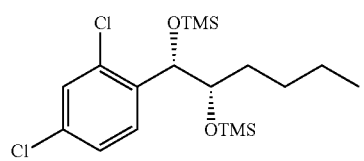

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

¹H NMR (400MHz, CDCl₃) δ−0.053 (s, 9H), 0.044 (s, 9H), 0.89~0.93 (m, 3H), 1.30~1.39 (m, 2H), 1.49~1.52 (m, 2H), 1.56~1.6 (m, 2H), 3.72~3.77 (m, 1H), 4.98 (t, J=4.8Hz, 1H), 7.28~7.50 (m, 3H)

Preparation Example 91

Preparation of 1-(2,6-dichlorophenyl)-(S,S)-1,2-(Bis-trimethylsilanyloxy)-hexane

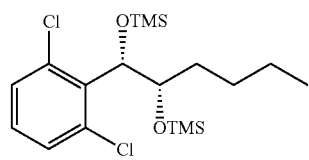

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

¹H NMR (400MHz, CDCl₃) δ−0.053 (s, 9H), 0.044 (s, 9H), 0.85 (t, J=6.7Hz, 3H), 1.20~1.31 (m, 4H), 1.45~1.53 (m, 2H), 4.28~4.33 (m, 1H), 5.25 (t, J=8.4Hz, 1H), 7.18~7.35 (m, 3H)

Preparation Example 92

Preparation of 1-(2,4-dichlorophenyl)-(R,R)-1,2-(Bis-trimethylsilanyloxy)-propane

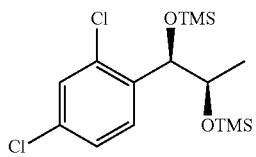

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR (400MHz, CDCl$_3$) δ −0.053 (s, 9H), 0.044 (s, 9H), 1.22 (d, J=6.4Hz, 3H), 3.90~3.95 (m, 1H), 4.94 (t, J=5.0Hz, 1H), 7.31~7.49 (m, 3H)

Preparation Example 93

Preparation of 1-(2,6-dichlorophenyl)-(R,R)-1,2-(Bis-trimethylsilanyloxy)-propane

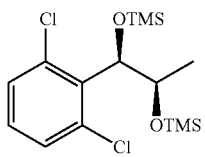

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR (400MHz, CDCl$_3$) δ −0.053 (s, 9H), 0.044 (s, 9H), 1.10 (d, J=6.4Hz, 3H), 4.47~4.54 (m, 1H), 5.24 (t, J=8.8Hz, 1H), 7.18~7.36 (m, 3H)

Preparation Example 94

Preparation of 1-(2,3-dichlorophenyl)-(R,R)-1,2-(Bis-trimethylsilanyloxy)-propane

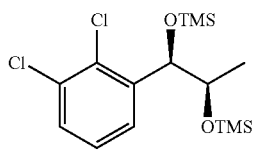

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR (400MHz, CDCl$_3$) δ −0.053 (s, 9H), 0.044 (s, 9H), 1.10 (d, J=6.4Hz, 3H), 4.47~4.54 (m, 1H), 5.24 (t, J=8.8Hz, 1H), 7.18~7.22 (m, 3H)

Preparation Example 95

Preparation of 1-(2,4-dichlorophenyl)-(R,R)-1,2-(Bis-trimethylsilanyloxy)-butane

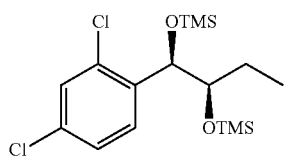

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

$^1$H NMR (400MHz, CDCl$_3$) δ −0.053 (s, 9H), 0.044 (s, 9H), 1.02 (t, J=7.4Hz, 3H), 1.54~1.61 (m, 2H), 3.65~3.68 (m, 1H), 5.01 (t, J=5.0Hz, 1H), 7.31~7.49 (m, 3H)

Preparation Example 96

Preparation of 1-(2,6-dichlorophenyl)-(R,R)-1,2-(Bis-trimethylsilanyloxy)-butane

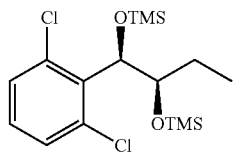

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

$^1$H NMR (400MHz, CDCl$_3$) δ −0.053(s, 9H), 0.044 (s, 9H), 0.97 (t, J=7.6Hz, 3H), 1.26~1.53 (m, 2H), 4.22~4.26 (m, 1H), 5.26 (t, J=8.4Hz, 1H), 7.17~7.35 (m, 3H)

Preparation Example 97

Preparation of 1-(2,4-dichlorophenyl)-3-methyl-(R,R)-1,2-(Bis-trimethylsilanyloxy)-butane

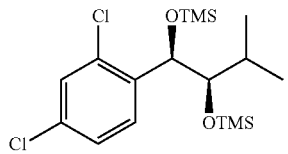

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

¹H NMR (400MHz, CDCl₃) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.30~7.53 (m, 3H)

Preparation Example 98

Preparation of 1-(2,6-dichlorophenyl)-3-methyl-(R,R)-1,2-(Bis-trimethylsilanyloxy)-butane

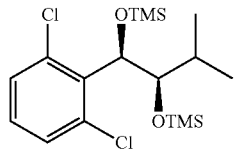

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).

¹H NMR (400MHz, CDCl₃) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.17~7.35 (m, 3H)

Preparation Example 99

Preparation of 1-(2,4-dichlorophenyl)-(R,R)-1,2-(Bis-trimethylsilanyloxy)-hexane

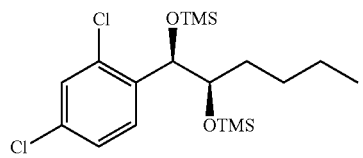

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

¹H NMR (400MHz, CDCl₃) δ−0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8Hz, 1H), 7.28~7.50 (m, 3H)

Preparation Example 100

Preparation of 1-(2,6-dichlorophenyl)-(R,R)-1,2-(Bis-trimethylsilanyloxy)-hexane

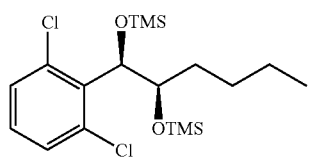

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

¹H NMR (400MHz, CDCl₃) δ−0.053 (s, 9H), 0.044 (s, 9H), 0.85 (t, J=6.7Hz, 3H), 1.20~1.31 (m, 4H), 1.45~1.53 (m, 2H), 4.28~4.33 (m, 1H), 5.25 (t, J=8.4Hz, 1H), 7.18~7.35 (m, 3H)

Preparation Example 101

Preparation of 1-(2,4-dichlorophenyl)-1,2-(Bis-trimethylsilanyloxy)-propane

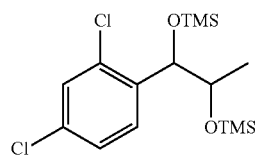

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

¹H NMR (400MHz, CDCl₃) δ−0.053 (s, 9H), 0.044 (s, 9H), 1.22 (d, J=6.4Hz, 3H), 3.90~3.95 (m, 1H), 4.94 (t, J=5.0Hz, 1H), 7.31~7.49 (m, 3H)

Preparation Example 102

Preparation of 1-(2,6-dichlorophenyl)-1,2-(Bis-trimethylsilanyloxy)-propane

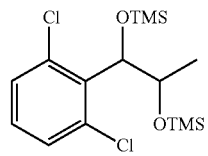

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

¹H NMR (400MHz, CDCl₃) δ−0.053 (s, 9H), 0.044 (s, 9H), 1.10 (d, J=6.4Hz, 3H), 4.47~4.54 (m, 1H), 5.24 (t, J=8.8Hz, 1H), 7.18~7.36 (m, 3H)

Preparation Example 103

Preparation of 1-(2,3-dichlorophenyl)-1,2-(Bis-trimethylsilanyloxy)-propane

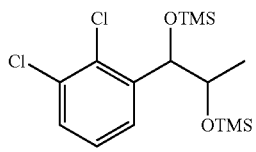

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).
$^1$H NMR (400MHz, CDCl$_3$) δ−0.053 (s, 9H), 0.044 (s, 9H), 1.10 (d, J=6.4Hz, 3H), 4.47~4.54 (m, 1H), 5.24 (t, J=8.8Hz, 1H), 7.18~7.22 (m, 3H)

Preparation Example 104

Preparation of 1-(2,4-dichlorophenyl)-1,2-(Bis-trimethylsilanyloxy)-butane

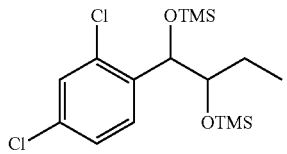

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).
$^1$H NMR (400MHz, CDCl$_3$) δ−0.053 (s, 9H), 0.044 (s, 9H), 1.02 (t, J=7.4Hz, 3H), 1.54~1.61 (m, 2H), 3.65~3.68 (m, 1H), 5.01 (t, J=5.0Hz, 1H), 7.31~7.49 (m, 3H)

Preparation Example 105

Preparation of 1-(2,6-dichlorophenyl)-1,2-(Bis-trimethylsilanyloxy)-butane

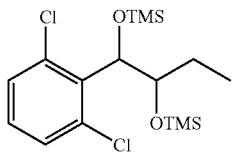

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).
$^1$H NMR (400MHz, CDCl$_3$) δ−0.053 (s, 9H), 0.044 (s, 9H), 0.97 (t, J=7.6Hz, 3H), 1.26~1.53 (m, 2H), 4.22~4.26 (m, 1H), 5.26 (t, J=8.4Hz, 1H), 7.17~7.35 (m, 3H)

Preparation Example 106

Preparation of 1-(2,4-dichlorophenyl)-3-methyl-1,2-(Bis-trimethylsilanyloxy)-butane

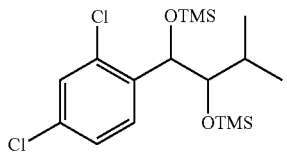

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).
$^1$H NMR (400MHz, CDCl$_3$) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.30~7.53 (m, 3H)

Preparation Example 107

Preparation of 1-(2,6-dichlorophenyl)-3-methyl-1,2-(Bis-trimethylsilanyloxy)-butane

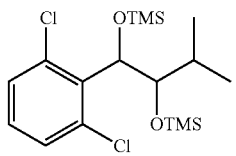

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).
$^1$H NMR (400MHz, CDCl$_3$) δ−0.053 (s, 9H), 0.044 (s, 9H), 1.00 (d, J=6.8Hz, 6H), 1.60~1.65 (m, 1H), 4.13~4.18 (m, 1H), 5.36 (t, J=7.6Hz, 1H), 7.17~7.35 (m, 3H)

Preparation Example 108

Preparation of 1-(2,4-dichlorophenyl)-1,2-(Bis-trimethylsilanyloxy)-hexane

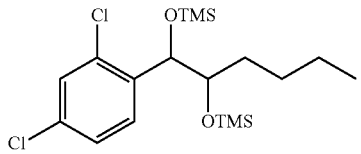

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

$^1$H NMR (400MHz, CDCl$_3$) δ−0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8Hz, 1H), 7.28~7.50 (m, 3H)

Preparation Example 109

Preparation of 1-(2,6-dichlorophenyl)-1,2-(Bis-trimethylsilanyloxy)-hexane

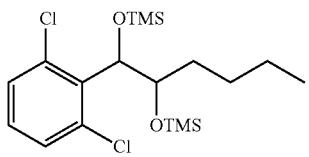

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

$^1$H NMR (400MHz, CDCl$_3$) δ−0.053 (s, 9H), 0.044 (s, 9H), 0.85 (t, J=6.7Hz, 3H), 1.20~1.31 (m, 4H), 1.45~1.53 (m, 2H), 4.28~4.33 (m, 1H), 5.25 (t, J=8.4Hz, 1H), 7.18~7.35 (m, 3H)

Preparation Example 110

Preparation of 1-(2-fluoroophenyl)-(S,S)-1,2-(Bis-trimethylsilanyloxy)-propane

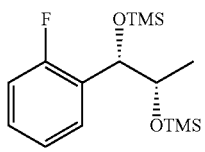

The substantially same method as described in Preparation Example 69 was conducted, except that 1-(2-fluoroophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

$^1$H NMR (400MHz, CDCl$_3$) δ−0.053 (s, 9H), 0.044(s, 9H), 1.15 (d, J=6.4Hz, 3H), 3.90~3.98 (m, 1H), 4.78 (dd, J=4.4, 7.2Hz, 1H), 7.04~7.50 (m, 4H)

Preparation Example 111

Preparation of 1-(2-fluorophenyl)-(R,R)-1,2-(Bis-trimethylsilanyloxy)-propane

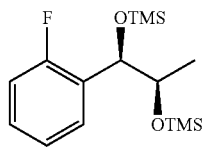

The substantially same method as described in Preparation Example 69 was conducted, except that 1-(2-fluoroophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

$^1$H NMR (400MHz, CDCl$_3$) δ−0.053 (s, 9H), 0.044 (s, 9H), 1.15 (d, J=6.4Hz, 3H), 3.90~3.98 (m, 1H), 4.78 (dd, J=4.4, 7.2Hz, 1H), 7.04~7.50 (m, 4H)

Preparation Example 112

Preparation of 1-(2-iodophenyl)-(S,S)-1,2-(Bis-trimethylsilanyloxy)-propane

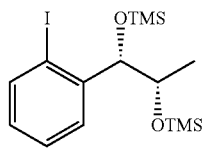

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

$^1$H NMR (400MHz, CDCl$_3$) δ−0.053 (s, 9H), 0.044 (s, 9H), 1.27 (d, J=6.4Hz, 3H), 3.99 (t, J=6.0Hz, 1H), 4.81 (d, J=4.0Hz, 1H), 7.01~7.87 (m, 4H)

Preparation Example 113

Preparation of 1-(2-iodophenyl)-(R,R)-1,2-(Bis-trimethylsilanyloxy)-propane

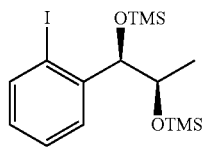

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

¹H NMR (400MHz, CDCl₃) δ−0.053 (s, 9H), 0.044 (s, 9H), 1.26 (d, J=6.4Hz, 3H), 3.98 (t, J=6.2Hz, 1H), 4.88 (d, J=4.4Hz, 1H), 7.00~7.87 (m, 4H)

Preparation Example 114

Preparation of 1-(2-iodophenyl)-(S,S)-1,2-(Bis-trimethylsilanyloxy)-butane

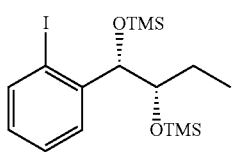

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).
¹H NMR (400MHz, CDCl₃) δ−0.053 (s, 9H), 0.044 (s, 9H), 1.04 (t, J=7.6Hz, 3H), 1.60~1.71 (m, 2H), 3.71~3.76 (m, 1H), 4.87 (d, J=4.8Hz, 1H), 7.01~7.87 (m, 4H)
Table 1: Example of Sulfamate Compound
*: Sodium salt Example 1

Preparation of 1-(2-chlorophenyl)-(S)-1-hydroxypropyl-(S)-2-carbamate (1)

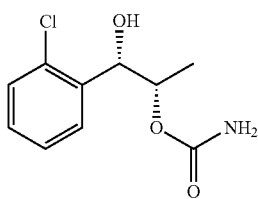

To a stirred solution of crude 1-(2-chlorophenyl)-(S,S)-1,2-(Bis-trimethylsilanyloxy) propane (preparation example 69, 104 g, 0.31 mol) in toluene (670 mL) was added by Chlorosulfonyl isocynate (62.5 mL, 0.71 mol) at 0° C. The reaction mixture was stirred for 2 hr. The reaction mixture was quenched with ice water and then was stirred by additional cold H₂O (500 mL) for 2 hr. After separation of organic layer, the aqueous was adjusted pH2~3 with sat. NaHCO₃ (400 mL) and extracted with EtOAc (300 mL×3). The EtOAc layer was washed with sat. NaHCO₃ (500 mL) and H₂O (500 mL). The organic phase was treated with Charcoal for 1.5 hr. The organic phase was filtered with Cellite, dried over MgSO₄. Filterion and concentration under vacuum provided the title compound of white solid (yield 85%(71.1 g), ee=99.9% MP=83~84, [α]D=+57.8 (c=0.25, MeOH))
¹H NMR(400MHz, CDCl₃) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)
¹³C NMR(100MHz, CDCl₃) δ16.4, 73.1, 75.0, 127.0, 128.4, 129.1, 129.5, 132.7, 138.0, 156.6

Example 2

Preparation of 1-(2-chlorophenyl)-(R)-1-hydroxypropyl-(R)-2-carbamate (2)

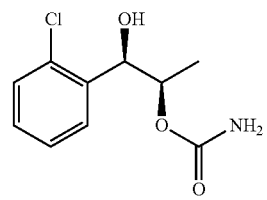

The substantially same method as described in Example 1 was conducted, except that 1-(2-chlorophenyl)-(R,R)-1,2-(Bis-trimethylsilanyloxy) propane (Preparation example 70) was used instead of 1-(2-chlorophenyl)-(S,S)-1,2-(Bis-trimethylsilanyloxy) propane (Preparation example 69) to obtain the title compound (5.7 g, yield 60~90%).
¹H NMR (400MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 3

Preparation of 1-(2-chlorophenyl)-1-hydroxypropyl-2-carbamate (3)

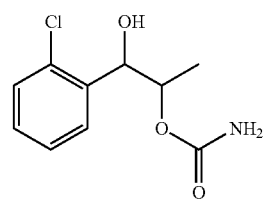

The substantially same method as described in Example 1 was conducted, except that 1-(2-chlorophenyl)-1,2-(Bis-trimethylsilanyloxy)propane (Preparation example 71) was used instead of 1-(2-chlorophenyl)-(S,S)-1,2-(Bis-trimethylsilanyloxy) propane (Preparation example 69) to obtain the title compound (3.8 g, yield 60~90%).
¹H NMR (400MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 4

Preparation of 1-(2-chlorophenyl)-(S)-1-hydroxypropyl-(R)-2-carbamate (4)

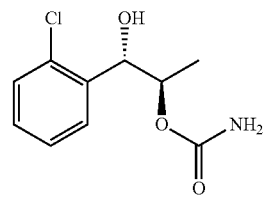

The substantially same method as described in Example 1 was conducted, except that 1-(2-chlorophenyl)-(S,R)-1,2-(Bis-trimethylsilanyloxy) propane (Preparation example 72) was used instead of 1-(2-chlorophenyl)-(S,S)-1,2-(Bis-trimethyl silanyloxy) propane (Preparation example 69) to obtain the title compound (2.4 g, yield 60~90%).

$^1$H NMR (400MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 5

Preparation of 1-(2-chlorophenyl)-(R)-1-hydroxy-propyl-(S)-2-carbamate (5)

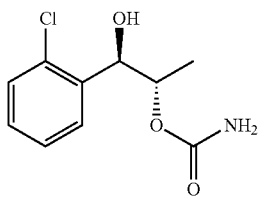

The substantially same method as described in Example 1 was conducted, except that 1-(2-chlorophenyl)-(R,S)-1,2-(Bis-trimethylsilanyloxy) propane (Preparation example 73) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR (400MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 6

Preparation of 1-(2-chlorophenyl)-(S)-1-hydroxybutyl-(S)-2-carbamate (6)

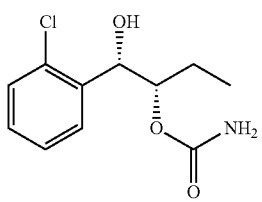

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR (400MHz, CDCl$_3$) δ0.96 (t, J=7.4Hz, 3H), 1.57~1.73 (m, 2H), 3.01 (d, J=5.6Hz, 1H), 4.74 (br s, 2H), 4.95 (dt, J=7.2, 8.8Hz, 1H), 5.23 (t, J=5.6Hz, 1H), 7.22~7.54 (m, 4H)

Example 7

Synthesis of 1-(2-chlorophenyl)-(R)-1-hydroxybutyl-(R)-2-carbamate (7)

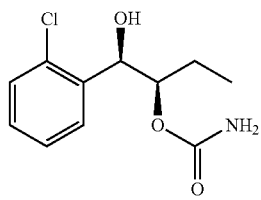 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR (400MHz, CDCl$_3$) δ 0.94 (t, J=7.4Hz, 3H), 1.53~1.73 (m, 2H), 2.92 (s, 1H), 4.78 (br s, 2H), 4.91~4.96 (m, 1H), 5.22 (d, J=5.5Hz, 1H), 7.20~7.54 (m, 4H)

Example 8

Synthesis of 1-(2-chlorophenyl)-1-hydroxybutyl-2-carbamate (8)

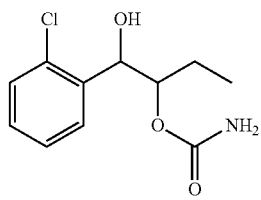 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR (400MHz, CDCl$_3$) δ 0.97 (t, J=7Hz, 3H), 1.58~1.74 (m, 2H), 2.94 (d, J=6Hz, 1H), 4.69 (br s, 2H), 4.94~4.99 (m, 1H), 5.24 (t, J=6Hz, 1H), 7.23~7.56 (m, 4H)

Example 9

Synthesis of 1-(2-chlorophenyl)-(S)-1-hydroxy-3-methyl-butyl-(S)-2-carbamate (9)

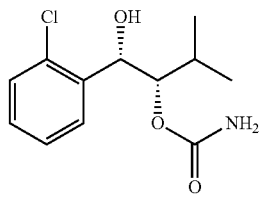 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy) propane (Preparation example 69) to obtain the title compound (1.7 g, yield 60~90%).

¹H NMR(400MHz, CDCl₃) δ1.01(d, J=6.4Hz, 3H), 1.09 (d, J=6.8Hz, 3H), 2.06(m, 1H), 2.75(d, J=6.8Hz, 1H), 4.58 (br s, 2H), 4.85~4.88(m, 1H), 5.34~5.37(m, 1H), 7.22~7.33 (m, 2H), 7.35~7.37(m, 1H), 7.51~7.53(m, 1H)

Example 10

Synthesis of 1-(2-chlorophenyl)-(R)-1-hydroxy-3-methyl-butyl-(R)-2-carbamate (10)

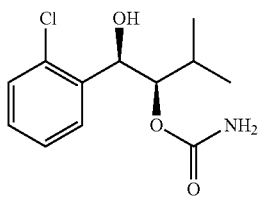 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy) propane (Preparation example 69) to obtain the title compound (1.6 g, yield 60~90%).

¹H NMR(400MHz, CDCl₃) δ1.01(d, J=6.8Hz, 3H), 1.09 (d, J=6.8Hz, 3H), 2.06(m, 1H), 2.73(d, J=6.8Hz, 1H), 4.57 (br s, 2H), 4.85~4.88(m, 1H), 5.34~5.37(m, 1H), 7.24~7.30 (m, 2H), 7.35~7.37(m, 1H), 7.51~7.53(m, 1H)

Example 11

Synthesis of 1-(2-chlorophenyl)-1-hydroxy-3-methyl-butyl-2-carbamate (11)

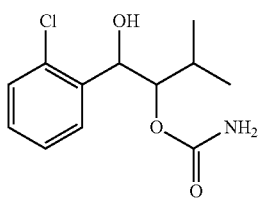 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy) propane (Preparation example 69) to obtain the title compound (1.7 g, yield 60~90%).

¹H NMR(400MHz, CDCl₃) δ1.00(d, J=6.4Hz, 3H), 1.09 (d, J=6.4Hz, 3H), 2.08(m, 1H), 2.76(d, J=6.0Hz, 1H), 4.59 (br s, 2H), 4.87(dd, J=7.2Hz, 4.4Hz, 1H), 5.36(t, J=4.6, 1H), 7.23~7.54(m, 4H)

Example 12

Synthesis of 1-(2-chlorophenyl)-(S)-1-hydroxy-hexyl-(S)-2-carbamate (12)

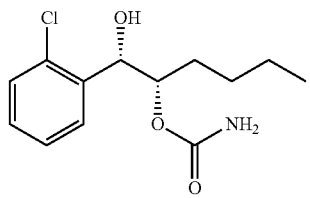 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy) propane (Preparation example 69) to obtain the title compound (2.3 g, yield 60~90%).

¹H NMR(400MHz, CDCl₃) δ0.88(t, J=7Hz, 3H), 1.33~1.42(m, 4H), 1.53~1.71(m, 2H), 2.89 (d, J=5.6Hz, 1H) 4.64 (br s, 2H), 5.04 (dt, J=5.0, 9.0Hz, 1H), 5.20 (t, J=5.6Hz, 1H), 7.23~7.55(m, 4H)

Example 13

Synthesis of 1-(2-chlorophenyl)-(R)-1-hydroxy-hexyl-(R)-2-carbamate (13)

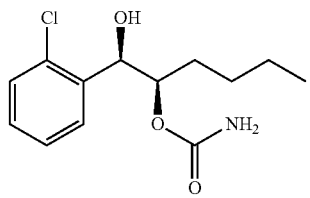 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy) propane (Preparation example 69) to obtain the title compound (2.2 g, yield 60~90%).

¹H NMR(400MHz, CDCl₃) δ 0.89(dd, J=5Hz, 3H), 1.28~1.43(m, 4H), 1.52~1.58(m, 1H), 1.65~1.72(m, 1H), 2.90(d, J=6Hz, 1H), 4.64(br s, 2H), 5.01~5.06(m, 1H), 5.22(t, J=6Hz, 1H), 7.22~7.56(m, 4H)

Example 14

Synthesis of 1-(2-chlorophenyl)-1-hydroxyhexyl-2-carbamate (14)

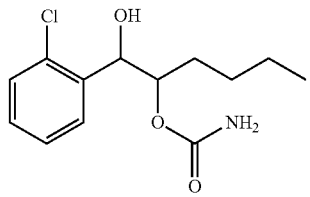 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR (400MHz, CDCl$_3$) δ 0.88 (dd, J=5Hz, 3H), 1.31~1.43 (m, 4H), 1.63~1.70 (m, 1H), 1.52~1.60 (m, 1H), 3.06 (d, J=6Hz, 1H), 4.75 (br s, 2H), 5.00~5.05 (m, 1H), 5.21 (t, J=6Hz, 1H), 7.22~7.55 (m, 4H)

Example 15

Synthesis of 1-(2-chlorophenyl)-(S)-1-hydroxypropyl-(S)-2-N-methylcarbamate (15)

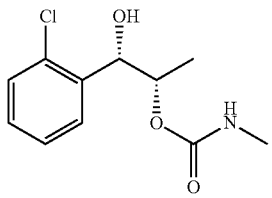 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH$_3$NH$_2$, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO$_4$), filtrated, and concentrated under reduced pressure. The concentrated residue was purified by a silica gel column chromatography, to obtain the title compound (1.6 g, yield 51%).

$^1$H NMR(400MHz, CDCl$_3$) δ1.03~1.25(m, 3H), 2.76(s, 3H), 3.34(s, 1H), 4.80(br s 1H), 5.04(t, J=12.5Hz, 1H), 5.14(s, 1H), 7.20~7.53(m, 4H)

Example 16

Synthesis of 1-(2-chlorophenyl)-(S)-1-hydroxypropyl-(S)-2-N-propylcarbamate (16)

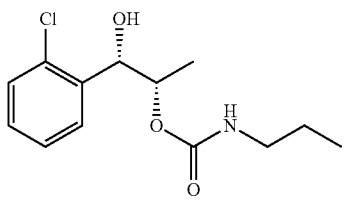 [SMILES: CCCNC(=O)O[C@@H](C)[C@@H](O)c1ccccc1Cl]

The substantially same method as described in Example 15 was conducted, except that propylamine was used instead of methylamine solution (CH$_3$NH$_2$ in EtOH), to obtain the title compound (0.79 g, yield 25%).

$^1$H NMR (400MHz, CDCl$_3$) δ0.90 (t, J=6.8Hz, 3H), 1.20 (d, J=5.96Hz, 3H), 1.49 (dd, J=14.2Hz, 2H), 3.11 (d, J=6.28Hz, 2H), 3.34 (s, 1H), 4.84 (br s, 1H), 5.05 (t, J=5.88Hz, 1H), 5.14 (s, 1H), 7.22~7.53 (m, 4H)

Example 17

Synthesis of 1-(2-chlorophenyl)-(S)-1-hydroxypropyl-(R)-2-N-isopropylcarbamate (17)

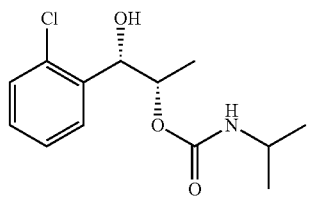 [SMILES: CC(C)NC(=O)O[C@@H](C)[C@@H](O)c1ccccc1Cl]

The substantially same method as described in Example 15 was conducted, except that isopropylamine was used instead of methylamine solution (CH$_3$NH$_2$ in EtOH), to obtain the title compound (1.5 g, yield 41%).

$^1$H NMR (400MHz, CDCl$_3$) δ1.14(dd, J=6.5Hz, 6H), 1.19(d, J=6.4Hz, 3H), 3.21(s, 1H), 3.73~3.82(m, 1H), 4.59 (br s, 1H), 5.01~5.07(m, 1H), 5.14(t, J=5.8Hz, 1H), 7.20~7.53(m, 4H)

Example 18

Synthesis of 1-(2-chlorophenyl)-(S)-1-hydroxypropyl-(R)-2-N-cyclopropylcarbamate (18)

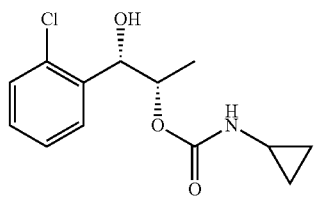 [SMILES: C[C@H](OC(=O)NC1CC1)[C@@H](O)c1ccccc1Cl]

The substantially same method as described in Example 15 was conducted, except that cyclopropylamine was used instead of methylamine solution (CH$_3$NH$_2$ in EtOH), to obtain the title compound (2.2 g, yield 43%).

$^1$H NMR (400MHz, CDCl$_3$) δ0.50~0.56 (m, 2H), 0.74 (d, J=7.21Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H)

Example 19

Synthesis of 1-(2-chlorophenyl)-(S)-1-hydroxypropyl-(R)-2-N-cyclohexyl carbamate (19)

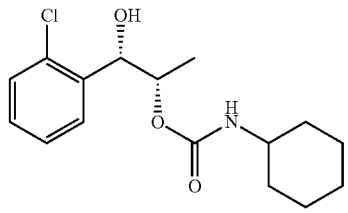 [SMILES: C[C@H](OC(=O)NC1CCCCC1)[C@@H](O)c1ccccc1Cl]

The substantially same method as described in Example 15 was conducted, except that cyclohexylamine was used instead of methylamine solution (CH$_3$NH$_2$ in EtOH), to obtain the title compound (1.1 g, yield 26%).

¹H NMR (400MHz, CDCl₃) δ1.06~1.40 (m, 7H), 1.56~1.61 (m, 2H), 1.69~1.71 (m, 2H), 1.87~1.94 (m, 2H), 3.19 (d, J=4.32Hz, 1H), 3.45 (s, 1H), 4.64 (br s 1H), 5.02~5.07 (m, 1H), 5.14 (t, J=6.08Hz, 1H) 7.20~7.53 (m, 4H)

Example 20

Synthesis of 1-(2-chlorophenyl)-(S)-1-hydroxypropyl-(S)-2-N-benzyl carbamate (20)

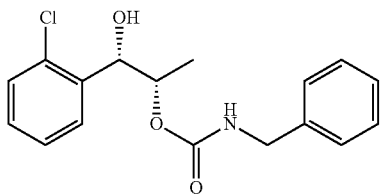 [SMILES: C[C@H](OC(=O)NCc1ccccc1)[C@@H](O)c1ccccc1Cl]

The substantially same method as described in Example 15 was conducted, except that benzylamine was used instead of methylamine solution (CH₃NH₂ in EtOH), to obtain the title compound (1.2 g, yield 18%).

¹H NMR(400MHz, CDCl₃) δ 1.27(d, J=10Hz, 3H), 3.12 (d, J=5Hz, 1H), 4.37(d, J=6Hz, 2H), 5.12~5.19(m, 3H), 7.15~7.56(m, 9H)

Example 21

Synthesis of 1-(2-chlorophenyl)-(S)-1-hydroxypropyl-(S)-2-N-bicyclo[2,2,1]heptanescarbamate (21)

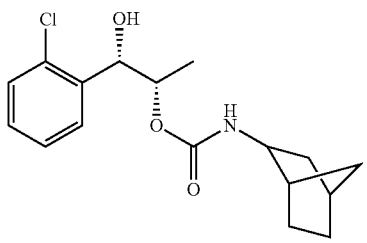

The substantially same method as described in Example 15 was conducted, except that 2-aminonorbornane was used instead of methylamine solution (CH₃NH₂ in EtOH), to obtain the title compound (1.7 g, yield 32%).

¹H NMR(400MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 22

Synthesis of 1-(2-chlorophenyl)-(R)-1-hydroxypropyl-(R)-2-N-methylcarbamate (22)

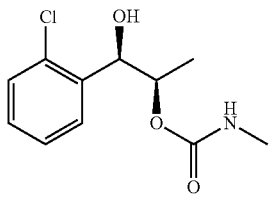 [SMILES: CNC(=O)O[C@H](C)[C@H](O)c1ccccc1Cl]

The substantially same method as described in Example 15 was conducted, except that 1-(2-chlorophenyl)-(R,R)-1,2-propanediol (Preparation example 15) was used instead of 1-(2-chlorophenyl)-(S,S)-1,2-propanediol (Preparation example 14), to obtain the title compound (3.36 g, yield 60%).

¹H NMR (400MHz, CDCl₃) δ 1.20 (d, J=6.8Hz, 3H), 2.80 (d, J=4.8Hz, 3H), 3.20 (d, J=4.4Hz, 1H), 4.75 (br s, 1H), 5.03~5.09 (m, 1H), 5.14~5.17 (m, 1H), 7.22~7.55 (m, 4H)

Example 23

Synthesis of 1-(2-chlorophenyl)-(R)-1-hydroxypropyl-(R)-2-N-propylcarbamate (23)

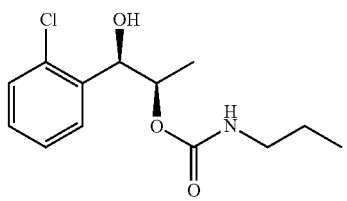 [SMILES: CCCNC(=O)O[C@H](C)[C@H](O)c1ccccc1Cl]

The substantially same method as described in Example 22 was conducted, except that propylamine was used instead of methylamine solution (CH₃NH₂ in EtOH), to obtain the title compound (3.1 g, yield 53%).

¹H NMR (400MHz, CDCl₃) δ0.92 (t, J=7.6Hz, 3H), 1.21 (d, J=6.4Hz, 3H), 1.51 (m, 2H), 3.09~3.14 (m, 2H), 3.28 (d, J=4.4Hz, 1H), 4.82 (br s, 1H), 5.03~5.09 (m, 1H), 5.14~5.17 (m, 1H), 7.22~7.55 (m. 4H)

Example 24

Synthesis of 1-(2-chlorophenyl)-(R)-1-hydroxypropyl-(R)-2-N-isopropylcarbamate (24)

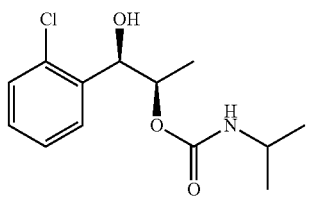 [SMILES: CC(C)NC(=O)O[C@H](C)[C@H](O)c1ccccc1Cl]

The substantially same method as described in Example 22 was conducted, except that isopropylamine was used instead of methylamine solution (CH₃NH₂ in EtOH), to obtain the title compound (0.16 g, yield 27%).

¹H NMR (400MHz, CDCl₃) δ0.88~1.16 (m, 6H), 1.19~1.26 (m, 3H), 3.34 (s, 1H), 3.71~3.78 (m, 1H), 4.62 (br s, 1H), 5.03 (t, J=5.8Hz, 1H), 5.13 (d, J=4.9Hz, 1H), 7.20~7.53 (m, 4H)

Example 25

Synthesis of 1-(2-chlorophenyl)-(R)-1-hydroxypropyl-(R)-2-N-cyclopropylcarbamate (25)

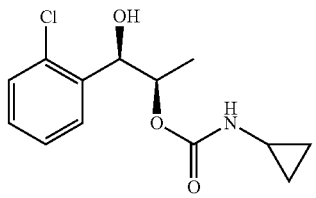 [SMILES: C[C@@H](OC(=O)NC1CC1)[C@H](O)c1ccccc1Cl]

The substantially same method as described in Example 22 was conducted, except that cyclopropylamine was used instead of methylamine solution (CH₃NH₂ in EtOH), to obtain the title compound (3.7 g, yield 60%).

¹H NMR(400MHz, CDCl₃) δ0.49~0.54(m, 2H), 0.74(d, J=7.2Hz, 2H), 1.22(s, 3H), 2.55~2.60(m, 1H), 3.16(s, 1H), 5.00(s, 1H), 5.04~5.11(m, 1H), 5.16(s, 1H), 7.23~7.54(m, 4H)

Example 26

Synthesis of 1-(2-chlorophenyl)-(R)-1-hydroxypropyl-(R)-2-N-cyclohexyl carbamate (26)

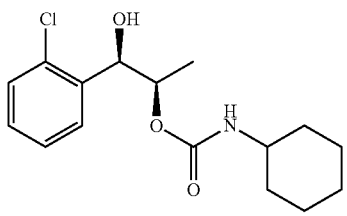 [SMILES: C[C@@H](OC(=O)NC1CCCCC1)[C@H](O)c1ccccc1Cl]

The substantially same method as described in Example 22 was conducted, except that cyclohexylamine was used instead of methylamine solution (CH₃NH₂ in EtOH), to obtain the title compound (1.9 g, yield 28%).

¹H NMR (400MHz, CDCl₃) δ1.05~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2Hz, 1H), 7.20~7.54 (m, 4H)

Example 27

Synthesis of 1-(2-chlorophenyl)-(R)-1-hydroxypropyl-(R)-2-N-benzylcarbamate (27)

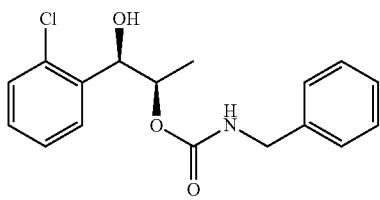 [SMILES: C[C@@H](OC(=O)NCc1ccccc1)[C@H](O)c1ccccc1Cl]

The substantially same method as described in Example 22 was conducted, except that benzylamine was used instead of methylamine solution (CH₃NH₂ in EtOH), to obtain the title compound (0.52 g, yield 19%).

¹H NMR (400MHz, CDCl₃) δ1.25 (d, J=6Hz, 3H), 1.64 (s, 1H), 3.13 (d, J=4.4Hz, 1H), 4.37 (d, J=5.6Hz, 2H), 5.12~5.19 (m, 2H), 7.23~7.55 (m, 9H)

Example 28

Synthesis of 1-(2-chlorophenyl)-(R)-1-hydroxypropyl-(R)-2-N-bicyclo[2,2,1]heptanecarbamate (28)

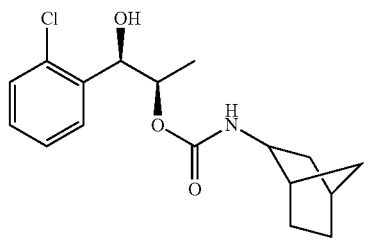 [SMILES: C[C@@H](OC(=O)NC1CC2CCC1C2)[C@H](O)c1ccccc1Cl]

The substantially same method as described in Example 22 was conducted, except that 2-aminonorbornane was used instead of methylamine solution (CH₃NH₂ in EtOH), to obtain the title compound (1.7 g, yield 20~50%).

¹H NMR (400MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 29

Synthesis of 1-(2-chlorophenyl)-1-hydroxypropyl-2-N-methylcarbamate (29)

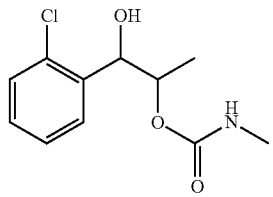 [SMILES: CNC(=O)OC(C)C(O)c1ccccc1Cl]

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

¹H NMR (400MHz, CDCl₃) δ 1.21 (d, J=6Hz, 3H), 2.81 (d, J=5Hz, 3H), 3.14 (d, J=4Hz, 1H), 4.72 (br s, 1H), 5.07 (dd, J=6Hz, 1H), 5.16 (t, J=6Hz, 1H), 7.22~7.56 (m, 4H)

Example 30

Synthesis of 1-(2-chlorophenyl)-1-hydroxypropyl-2-N-propylcarbamate (30)

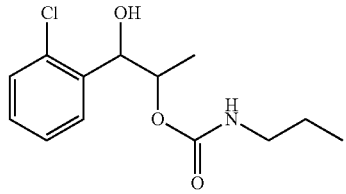 [SMILES: CCCNC(=O)OC(C)C(O)c1ccccc1Cl]

The substantially same method as described in Example 29 was conducted, except that propylamine was used instead of methylamine solution (CH₃NH₂ in EtOH), to obtain the title compound (1.0 g, yield 17%).

¹H NMR(400MHz, CDCl₃) δ 0.92(t, J=7Hz, 3H), 1.21(d, J=6Hz, 3H), 1.53(dd, J=7Hz, 2H), 3.13(dd, J=7Hz, 2H), 3.28(d, 1H), 4.82(S, 1H), 5.06(dd, J=7Hz, 1H), 5.16(t, J=5Hz, 1H), 7.21~7.56(m, 4H)

Example 31

Synthesis of 1-(2-chlorophenyl)-1-hydroxypropyl-2-N-isopropylcarbamate (31)

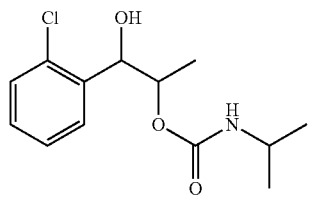 [SMILES: CC(C)NC(=O)OC(C)C(O)c1ccccc1Cl]

The substantially same method as described in Example 29 was conducted, except that isopropylamine was used instead of methylamine solution (CH₃NH₂ in EtOH), to obtain the title compound (0.54 g, yield 16%).

¹H NMR(400MHz, CDCl₃) δ 1.16(dd, J=6Hz, 6H), 1.21 (d, J=6Hz, 3H), 3.23(d, J=6Hz, 1H), 3.75~3.84(m, 1H), 4.61(br s, 1H), 5.06(t, J=6Hz, 1H), 5.16(t, J=6Hz, 1H), 7.22~7.56(m, 4H)

Example 32

Synthesis of 1-(2-chlorophenyl)-1-hydroxypropyl-2-N-cyclopropylcarbamate (32)

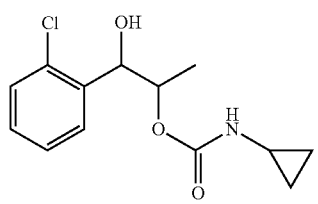 [SMILES: CC(OC(=O)NC1CC1)C(O)c1ccccc1Cl]

The substantially same method as described in Example 29 was conducted, except that cyclopropylamine was used instead of methylamine solution (CH₃NH₂ in EtOH), to obtain the title compound (1.0 g, yield 17%).

¹H NMR(400MHz, CDCl₃) δ 0.50(t, J=6Hz, 2H), 0.77(t, J=3Hz, 2H), 1.12(d, J=7Hz, 3H), 2.53~2.59(m, 1H), 3.22(d, J=4Hz, 1H), 5.08(dd, J=6Hz, 1H), 5.15(S, 1H), 7.22~7.55 (m, 4H)

Example 33

Synthesis of 1-(2-chlorophenyl)-1-hydroxypropyl-2-N-cyclohexylcarbamate (33)

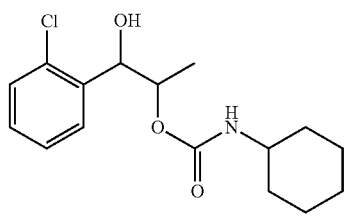 [SMILES: CC(OC(=O)NC1CCCCC1)C(O)c1ccccc1Cl]

The substantially same method as described in Example 29 was conducted, except that cyclohexylamine was used instead of methylamine solution (CH₃NH₂ in EtOH), to obtain the title compound (2.2 g, yield 33%).

¹H NMR(400MHz, CDCl₃) δ 1.07~1.17(m, 3H), 1.21(d, J=6Hz, 3H), 1.29~1.42(m, 3H), 1.72(dd, J=6Hz, 2H), 1.92 (dd, J=6Hz, 2H), 3.26(d, J=4Hz, 1H), 3.46(t, J=4Hz, 1H), 4.68(d, J=6Hz, 1H), 5.07(dd, J=6Hz, 1H), 5.16(t, J=6Hz, 1H), 7.22~7.55(m, 4H)

Example 34

Synthesis of 1-(2-chlorophenyl)-1-hydroxypropyl-2-N-benzylcarbamate (34)

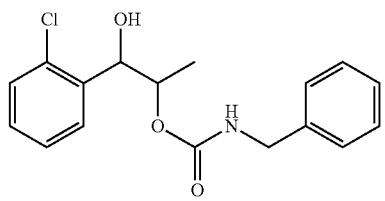 [SMILES: CC(OC(=O)NCc1ccccc1)C(O)c1ccccc1Cl]

The substantially same method as described in Example 29 was conducted, except that benzylamine was used instead of methylamine solution (CH₃NH₂ in EtOH), to obtain the title compound (1.3 g, yield 19%).

¹H NMR(400MHz, CDCl₃) δ 1.25(d, J=6Hz, 3H), 3.16(d, J=4Hz, 1H), 4.36(d, J=6Hz, 2H), 5.14(dd, J=6Hz, 3H), 7.23~7.56(m, 9H), yield: 19% (1.3 g)

Example 35

Synthesis of 1-(2-chlorophenyl)-1-hydroxypropyl-2-N-bicyclo[2,2,1]heptanecarbamate (35)

The substantially same method as described in Example 29 was conducted, except that 2-aminonorbornane was used instead of methylamine solution (CH₃NH₂ in EtOH), to obtain the title compound (1.7 g, yield 20~50%).

¹H NMR (400MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 36

Synthesis of 1-(2,4-dichlorophenyl)-(S)-1-hydroxypropyl-(S)-2-carbamate (36)

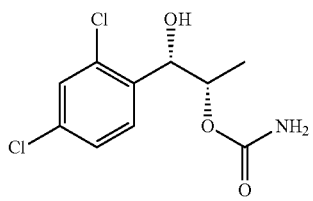 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1, 2-(Bis-trimethylsilanyloxy)propane (Preparation Example 83) was used instead of 1-(2-chlorophenyl)-(S,S)-1,2-(Bis-trimethyl silanyloxy) propane (Preparation example 69) to obtain the title compound (1.8 g, yield 60~90%).

¹H NMR (400MHz, CDCl₃) δ1.22 (d, J=6.4Hz, 3H), 4.16 (br t, 1H) 4.96 (br t, 3H), 5.07 (t, J=4.8Hz, 1H), 7.23~7.52 (m, 3H)

Example 37

Synthesis of 1-(2,6-dichlorophenyl)-(S)-1-hydroxypropyl-(S)-2-carbamate (37)

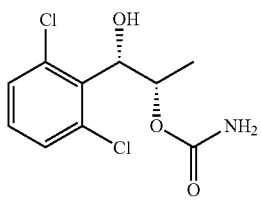 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1, 2-(Bis-trimethylsilanyloxy)propane (Preparation Example 84) was used instead of 1-(2-chlorophenyl)-(S,S)-1,2-(Bis-trimethylsilanyloxy) propane (Preparation example 69) to obtain the title compound (2.6 g, yield 60~90%)

Example 38

Synthesis of 1-(2,3-dichlorophenyl)-(S)-1-hydroxypropyl-(S)-2-carbamate (38)

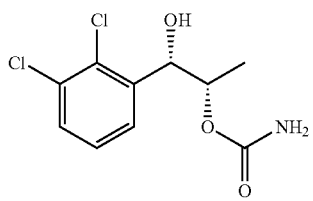 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1, 2-(Bis-trimethylsilanyloxy)propane (Preparation Example 85) was used instead of 1-(2-chlorophenyl)-(S,S)-1,2-(Bis-trimethylsilanyloxy) propane (Preparation example 69) to obtain the title compound (1.4 g, yield 60~90%)

¹H NMR (400MHz, CDCl₃) δ1.15 (d, J=6.4Hz, 3H), 3.66 (d, J=9.2Hz, 1H), 4.73 (br s, 2H), 5.43 (t, J=9.0Hz, 1H), 5.62~5.69 (m, 1H), 7.18~7.22 (m, 3H),

Example 39

Synthesis of 1-(2,4-dichlorophenyl)-(S)-1-hydroxybutyl-(S)-2-carbamate (39)

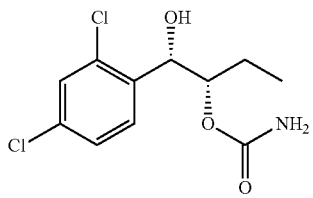 [SMILES: CC[C@H](OC(N)=O)[C@@H](O)c1ccc(Cl)cc1Cl]

The substantially same method as described in Example 1 was conducted, except that 1-(2,4-dichlorophenyl)-(S,S)-1, 2-(Bis-trimethylsilanyloxy)butane (Preparation Example 86) was used instead of 1-(2-chlorophenyl)-(S,S)-1,2-(Bis-trimethylsilanyloxy) propane (Preparation example 69) to obtain the title compound (2.3 g, yield 60~90%).

¹H NMR(400MHz, CDCl₃) δ0.96(t, J=7.4Hz, 3H), 1.58~1.74(m, 2H), 2.98(d, J=5.6Hz, 1H) 4.68(br s, 2H), 5.59(dt, J=5.2, 8.8Hz, 1H), 5.19(t, J=5.4Hz, 1H), 7.30~7.50 (m, 3H)

Example 40

Synthesis of 1-(2,6-dichlorophenyl)-(S)-1-hydroxybutyl-(S)-2-carbamate (40)

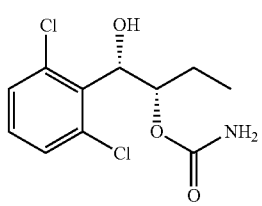 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1, 2-(Bis-trimethylsilanyloxy)butane (Preparation Example 87) was used instead of 1-(2-chlorophenyl)-(S,S)-1,2-(Bis-trimethylsilanyloxy) propane (Preparation example 69) to obtain the title compound (1.7 g, yield 60~90%).

¹H NMR(400MHz, CDCl₃) δ0.92(t, J=7.4Hz, 3H), 1.30~1.38(m, 1H), 1.57~1.64(m, 1H), 3.74(d, J=9.2Hz, 1H), 4.80(br s, 2H), 5.40~5.50(m, 2H), 7.17~7.34(m, 3H)

Example 41

Synthesis of 1-(2,4-dichlorophenyl)-(S)-1-hydroxy-3-methyl-butyl-(S)-2-carbamate (41)

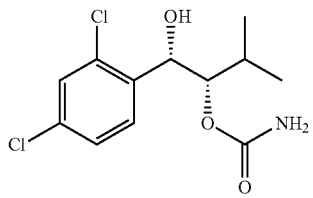 [SMILES: CC(C)[C@H](OC(N)=O)[C@@H](O)c1ccc(Cl)cc1Cl]

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR (400MHz, CDCl$_3$) δ1.00 (t, J=7.2Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 42

Synthesis of 1-(2,6-dichlorophenyl)-(S)-1-hydroxy-3-methyl-butyl-(S)-2-carbamate (42)

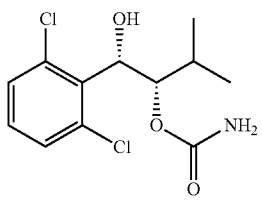 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR (400MHz, CDCl$_3$) δ1.00 (t, J=7.2Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 43

Synthesis of 1-(2,4-dichlorophenyl)-(S)-1-hydroxy-hexyl-(S)-2-carbamate (43)

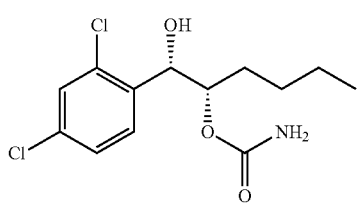 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR (400MHz, CDCl$_3$) δ0.89 (t, J=3.6Hz, 3H), 1.28~1.42 (m, 4H), 1.52~1.59 (m, 1H), 1.64~1.71 (m, 1H), 2.98 (d, J=5.6Hz, 1H), 4.67 (br s, 2H), 4.96~5.00 (m, 1H), 5.17 (t, J=5.6Hz, 1H), 7.30~7.49 (m 3H)

Example 44

Synthesis of 1-(2,6-dichlorophenyl)-(S)-1-hydroxy-hexyl-(S)-2-carbamate (44)

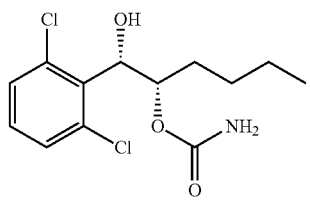

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy) propane (Preparation example 69) to obtain the title compound (2.1 g, yield 60~90%)

$^1$H NMR(400MHz, CDCl$_3$) δ0.84(t, J=7.0Hz, 3H), 1.20~1.35(m, 4H), 1.36~1.41(m, 1H), 1.59~1.63(m, 1H), 3.71(d, J=10.0Hz, 1H), 4.74(br s, 2H), 5.40~5.44(m, 1H), 5.52~5.57(m, 1H), 7.17~7.35(m, 3H)

Example 45

Synthesis of 1-(2,4-dichlorophenyl)-(R)-1-hydroxy-propyl-(R)-2-carbamate (45)

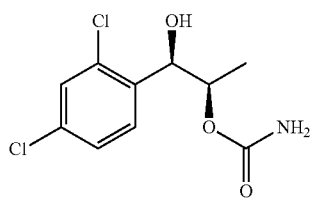 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy) propane (Preparation example 69) to obtain the title compound (1.2 g, yield 60~90%), $^1$H NMR (400MHz, CDCl$_3$) δ1.22 (d, J=6.4Hz, 3H), 4.16 (br t, 1H), 4.96 (br t, 3H), 5.07 (t, J=4.8Hz, 1H), 7.23~7.52 (m, 3H)

Example 46

Synthesis of 1-(2,6-dichlorophenyl)-(R)-1-hydroxy-propyl-(R)-2-carbamate (46)

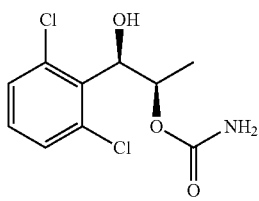 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy) propane (Preparation example 69) to obtain the title compound (1.7 g, yield 60~90%), $^1$H NMR (400MHz, CDCl$_3$) δ1.15 (d, J=6.4Hz, 3H), 3.66 (d, J=9.2Hz, 1H), 4.73 (br s, 2H), 5.43 (t, J=9.0Hz, 1H), 5.62~5.69 (m, 1H), 7.18~7.22 (m, 3H),

Example 47

Synthesis of 1-(2,3-dichlorophenyl)-(R)-1-hydroxy-propyl-(R)-2-carbamate (47)

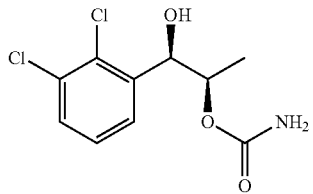 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy) propane (Preparation example 69) to obtain the title compound (2.0 g, yield 60~90%)

$^1$H NMR (400MHz, CDCl$_3$) δ1.15(d, J=6.4Hz, 3H), 3.66 (d, J=9.2Hz, 1H), 4.73(br s, 2H), 5.43(t, J=9.0Hz, 1H), 5.62~5.69(m, 1H), 7.18~7.22(m, 3H),

Example 48

Synthesis of 1-(2,4-dichlorophenyl)-(R)-1-hydroxy-butyl-(R)-2-carbamate (48)

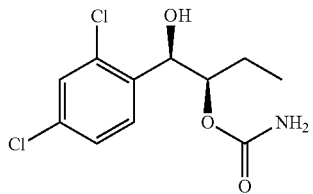 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR (400MHz, CDCl$_3$) δ0.96 (t, J=7.4Hz, 3H), 1.58~1.74 (m, 2H), 2.98 (d, J=5.6Hz, 1H), 4.68 (br s, 2H), 5.59 (dt, J=5.2, 8.8Hz, 1H), 5.19 (t, J=5.4Hz, 1H), 7.30~7.50 (m, 3H)

Example 49

Synthesis of 1-(2,6-dichlorophenyl)-(R)-1-hydroxy-butyl-(R)-2-carbamate (49)

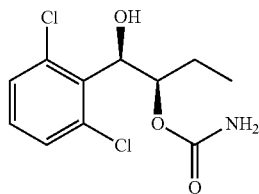 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR (400MHz, CDCl$_3$) δ0.92 (t, J=7.4Hz, 3H), 1.30~1.38 (m, 1H), 1.57~1.64 (m, 1H), 3.74 (d, J=9.2Hz, 1H), 4.80 (br s, 2H), 5.40~5.50 (m, 2H), 7.17~7.34 (m, 3H)

Example 50

Synthesis of 1-(2,4-dichlorophenyl)-(R)-1-hydroxy-3-methyl-butyl-(R)-2-carbamate (50)

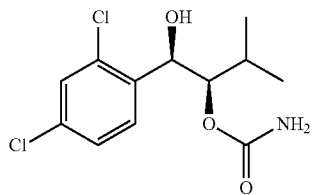 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy) propane (Preparation example 69) to obtain the title compound (2.8 g, yield 60~90%).

$^1$H NMR (400MHz, CDCl$_3$) δ1.00 (t, J=7.2Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 51

Synthesis of 1-(2,6-dichlorophenyl)-(R)-1-hydroxy-3-methyl-butyl-(R)-2-carbamate (51)

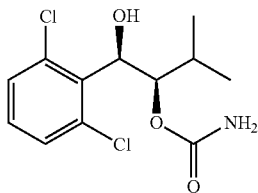 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400MHz, CDCl$_3$) δ1.00(t, J=7.2Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 52

Synthesis of 1-(2,4-dichlorophenyl)-(R)-1-hydroxy-hexyl-(R)-2-carbamate (52)

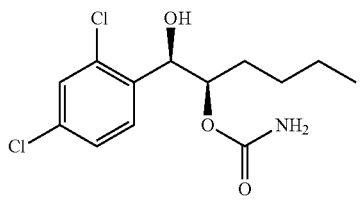 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR (400MHz, CDCl$_3$) δ0.89 (t, J=3.6Hz, 3H), 1.28~1.42 (m, 4H), 1.52~1.59 (m, 1H), 1.64~1.71 (m, 1H), 2.98 (d, J=5.6Hz, 1H), 4.67 (br s, 2H), 4.96~5.00 (m, 1H), 5.17 (t, J=5.6Hz, 1H), 7.3~7.49 (m, 3H)

Example 53

Synthesis of 1-(2,6-dichlorophenyl)-(R)-1-hydroxy-hexyl-(R)-2-carbamate (53)

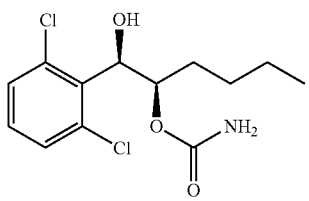 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR (400MHz, CDCl$_3$) δ0.84 (t, J=7.0Hz, 3H), 1.20~1.35 (m, 4H), 1.36~1.41 (m, 1H), 1.59~1.63 (m, 1H), 3.71 (d, J=10.0Hz, 1H), 4.74 (br s, 2H), 5.40~5.44 (m, 1H), 5.52~5.57 (m, 1H), 7.17~7.35 (m, 3H)

Example 54

Synthesis of 1-(2,4-dichlorophenyl)-1-hydroxypropyl-2-carbamate (54)

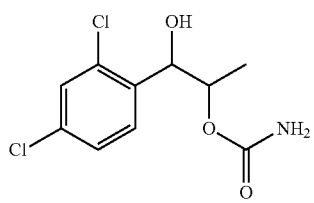 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 55

Synthesis of 1-(2,6-dichlorophenyl)-1-hydroxypropyl-2-carbamate (55)

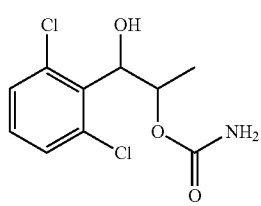 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 56

Synthesis of 1-(2,3-dichlorophenyl)-1-hydroxypropyl-2-carbamate (56)

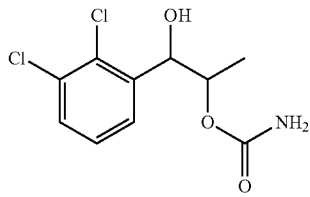 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 57

Synthesis of 1-(2,4-dichlorophenyl)-1-hydroxybutyl-2-carbamate (57)

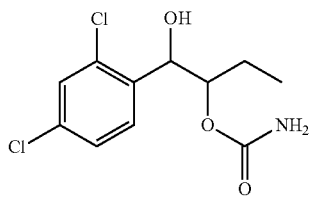 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ0.96(t, J=7.4Hz, 3H), 1.58~1.74(m, 2H), 2.98(d, J=5.6Hz, 1H) 4.68(br s, 2H), 5.59(dt, J=5.2, 8.8Hz, 1H), 5.19(t, J=5.4Hz, 1H), 7.30~7.50 (m, 3H)

Example 58

Synthesis of 1-(2,6-dichlorophenyl)-1-hydroxybutyl-2-carbamate (58)

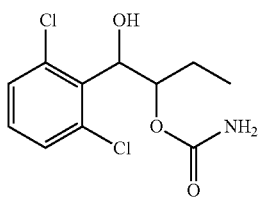 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400MHz, CDCl$_3$) δ0.92(t, J=7.4Hz, 3H), 1.30~1.38(m, 1H), 1.57~1.64(m, 1H), 3.74(d, J=9.2Hz, 1H), 4.80(br s, 2H), 5.40~5.50(m, 2H), 7.17~7.34(m, 3H)

Example 59

Synthesis of 1-(2,4-dichlorophenyl)-1-hydroxy-3-methyl-butyl-2-carbamate (59)

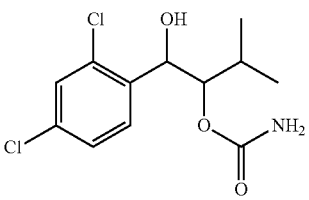 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR (400MHz, CDCl$_3$) δ1.00 (t, J=7.2Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 60

Synthesis of 1-(2,6-dichlorophenyl)-1-hydroxy-3-methyl-butyl-2-carbamate (60)

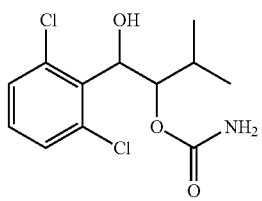 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400MHz, CDCl$_3$) δ1.00 (t, J=7.2Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 61

Synthesis of 1-(2,4-dichlorophenyl)-1-hydroxyhexyl-2-carbamate (61)

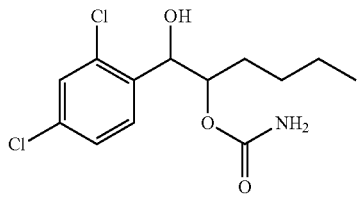 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR (400MHz, CDCl$_3$) δ0.89 (t, J=3.6Hz, 3H), 1.28~1.42 (m, 4H), 1.52~1.59 (m, 1H), 1.64~1.71 (m, 1H), 2.98 (d, J=0.5.6Hz, 1H), 4.67 (br s, 2H), 4.96~5.00 (m, 1H), 5.17 (t, J=5.6Hz, 1H), 7.30~7.49 (m, 3H)

Example 62

Synthesis of 1-(2,6-dichlorophenyl)-1-hydroxyhexyl-2-carbamate (62)

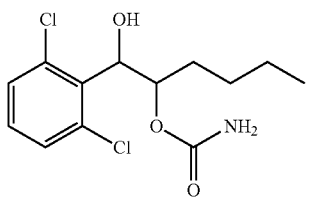 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR (400MHz, CDCl$_3$) δ0.84 (t, J=7.0Hz, 3H), 1.20~1.35 (m, 4H), 1.36~1.41 (m, 1H), 1.59~1.63 (m, 1H), 3.71 (d, J=10.0Hz, 1H), 4.74 (br s, 2H), 5.40~5.44 (m, 1H), 5.52~5.57 (m, 1H), 7.17~7.35 (m, 3H)

Example 63

Synthesis of 1-(2-fluorophenyl)-(S)-1-hydroxypropyl-(S)-2-carbamate (63)

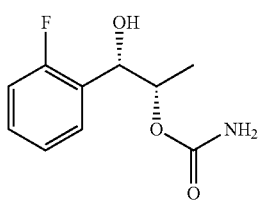

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy) propane (Preparation example 69) to obtain the title compound (1.8 g, yield 60~90%).

$^1$H NMR (400MHz, CDCl$_3$) δ1.19 (d, J=5.2Hz, 3H), 2.93 (d, J=4.4Hz, 1H), 4.71 (br s, 2H), 4.99~5.06 (m, H), 7.04~7.48 (m, 4H)

Example 64

Synthesis of 1-(2-fluorophenyl)-(R)-1-hydroxypropyl-(R)-2-carbamate (64)

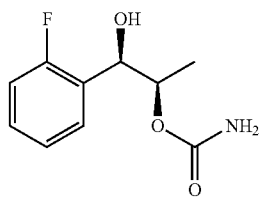

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR (400MHz, CDCl$_3$) δ1.19 (d, J=5.2Hz, 3H), 2.93 (d, J=4.4Hz, 1H), 4.71 (br s, 2H), 4.99~5.06 (m, H), 7.04~7.48 (m, 4H)

Example 65

Synthesis of 1-(2-iodophenyl)-(S)-1-hydroxypropyl-(S)-2-carbamate (65)

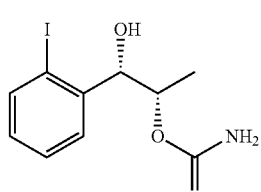

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR (400MHz, CDCl$_3$) δ1.27 (d, J=6.4Hz, 3H), 3.09 (br s, 1H), 4.83 (br s, 2H), 5.00~5.10 (m, 2H), 7.00~7.76 (m, 4H)

Example 66

Synthesis of 1-(2-iodophenyl)-(R)-1-hydroxypropyl-(R)-2-carbamate (66)

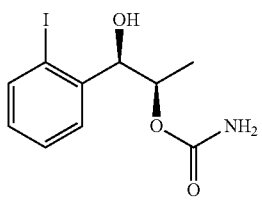

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400MHz, CDCl$_3$) δ1.27 (d, J=6.4Hz, 3H), 2.95 (d, J=3.6Hz, 1H), 4.73 (br s, 2H), 5.01~5.11 (m, 2H), 7.01~7.86 (m, 4H)

Example 67

Synthesis of 1-(2-iodophenyl)-(S)-1-hydroxybutyl-(S)-2-carbamate (67)

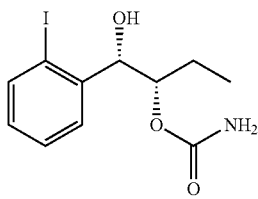 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR (400MHz, CDCl$_3$) δ1.27 (d, J=6.4Hz, 3H), 3.09 (br s, 1H), 4.83 (br s, 2H), 5.00~5.10 (m, 2H), 7.00~7.76 (m, 4H)

Example 68

Synthesis of 1-(2-chlorophenyl)-(S)-2-hydroxypropyl-(S)-1-carbamate (68)

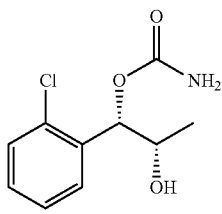

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH$_4$OH, 4 ml) was added thereto. When the reaction was completed, the obtained product was washed with 1M HCl solution and ethylacetate (EA). The separated organic layer was dehydrated with anhydrous magnesium sulfate (MgSO$_4$), filtrated, and concentrated under reduced pressure. The concentrated residue was purified by a silica gel column chromatography, to obtain the title compound (0.28 g, yield 10~30%).

$^1$H NMR (400MHz, CDCl$_3$) δ1.24 (d, J=6.8Hz, 3H), 2.13 (d, J=4.4Hz, 1H), 4.12~4.16 (m, 1H), 4.85 (br s, 2H), 5.98 (d, J=5.6Hz, 1H), 7.24~7.43 (m, 4H)

Example 69

Synthesis of 1-(2-chlorophenyl)-(R)-2-hydroxypropyl-(R)-1-carbamate (69)

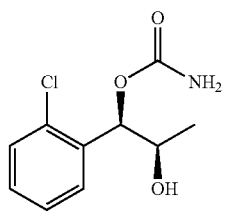

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

$^1$H NMR (400MHz, CDCl$_3$) δ1.24 (d, J=6.4Hz, 3H), 2.04 (d, J=4.8Hz, 1H), 4.11~4.18 (m, 1H), 4.74 (br s, 2H), 6.00 (d, J=5.6Hz, 1H), 7.24~7.43 (m, 4H)

Example 70

Synthesis of 1-(2-chlorophenyl)-2-hydroxypropyl-1-carbamate (70)

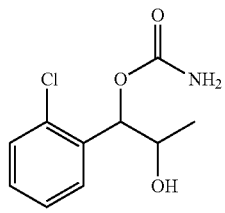

The substantially same method as described in Example 68 was conducted, except that 1-(2-chlorophenyl)-(R,R)-1,2-propanediol (Preparation Example 16) was used instead of 1-(2-chlorophenyl)-(S,S)-1,2-propanediol (Preparation example 14) to obtain the title compound (0.16 g, yield 10~30%).

¹H NMR (400MHz, CDCl₃) δ1.24 (d, J=6.4Hz, 3H), 2.04 (d, J=4.8Hz, 1H), 4.11~4.18 (m, 1H), 4.74 (br s, 2H), 6.00 (d, J=5.6Hz, 1H), 7.24~7.43 (m, 4H)

Example 71

Synthesis of 1-(2-chlorophenyl)-(S)-2-hydroxypropyl-(S)-1-N-methylcarbamate (71)

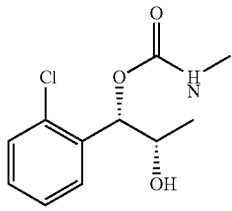 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

¹H NMR (400MHz, CDCl₃) δ1.21 (d, 0.7~6.4Hz, 3H), 2.80 (d, J=4.8Hz, 3H), 3.12 (s, 1H), 4.09~4.16 (m, 1H), 4.86 (br s, 1H), 5.99 (d, J=6.0Hz, 1H), 7.23~7.40 (m, 4H)

Example 72

Synthesis of 1-(2-chlorophenyl)-(R)-2-hydroxypropyl-(R)-1-N-methylcarbamate (72)

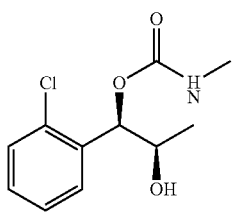 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).

¹H NMR (400MHz, CDCl₃) δ1.21 (d, J=6.4Hz, 3H), 2.80 (d, J=4.8Hz, 3H), 3.12 (s, 1H), 4.09~4.16 (m, 1H), 4.86 (br s, 1H), 5.99 (d, J=6.0Hz, 1H), 7.23~7.40 (m, 4H)

Example 73

Synthesis of 1-(2-chlorophenyl)-2-hydroxypropyl-1-N-methylcarbamate (73)

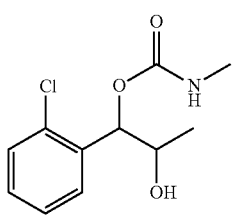 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

¹H NMR (400MHz, CDCl₃) δ 1.22 (d, J=6Hz, 3H), 2.15 (d, 0.7=4Hz, 1H), 2.81 (d, J=5Hz, 3H), 4.12 (dd, J=6Hz, 1H), 4.83 (br s, 1H), 6.00 (d, J=6Hz, 1H), 7.23~7.41 (m, 4H)

Example 74

Synthesis of 1-(2-chlorophenyl)-(S)-2-hydroxypropyl-(S)-1-N-propylcarbamate (74)

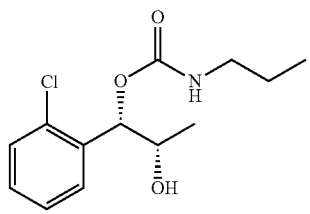 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).

¹H NMR (400MHz, CDCl₃) δ 0.91 (t, J=7Hz, 3H), 1.22 (d, J=6Hz, 3H), 1.52 (dd, J=7Hz, 2H), 2.23 (d, J=4Hz, 1H), 3.09~3.21 (m, 2H), 4.09~4.17 (m, 1H), 4.93 (s, 1H), 5.99 (d, J=6Hz, 1H), 7.23~7.47 (m, 4H)

Example 75

Synthesis of 1-(2-chlorophenyl)-(R)-2-hydroxypropyl-(R)-1-N-propylcarbamate (75)

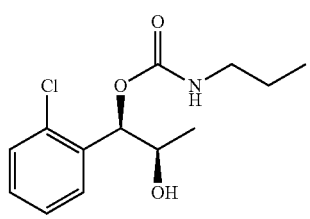 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

¹H NMR (400MHz, CDCl₃) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 76

Synthesis of 1-(2-chlorophenyl)-2-hydroxypropyl-1-N-propylcarbamate (76)

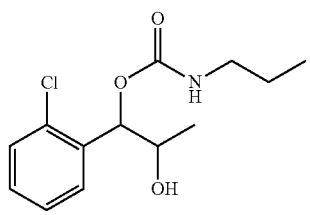 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

¹H NMR (400MHz, CDCl₃) δ 0.91 (t, J=7Hz, 3H), 1.22 (d, J=6Hz, 3H), 1.52 (dd, J=7Hz, 2H), 2.23 (d, J=4Hz, 1H), 3.09~3.21 (m, 2H), 4.09~4.17 (m, 1H), 4.93 (s, 1H), 5.99 (d, J=6Hz, 1H), 7.23~7.47 (m, 4H)

Example 77

Synthesis of 1-(2-chlorophenyl)-(S)-2-hydroxypropyl-(S)-1-N-isopropylcarbamate (77)

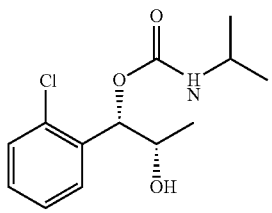 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).

¹H NMR (400MHz, CDCl₃) δ 1.10 (d, J=6.0Hz, 3H), 1.15~1.19 (m, 6H), 2.41 (s, 1H), 3.76~4.08 (m, 1H), 4.34 (s, 1H), 4.83 (br s 1H), 5.95 (d, J=5.3Hz, 1H), 7.19~7.39 (m, 4H)

Example 78

Synthesis of 1-(2-chlorophenyl)-(R)-2-hydroxypropyl-(R)-1-N-isopropylcarbamate (78)

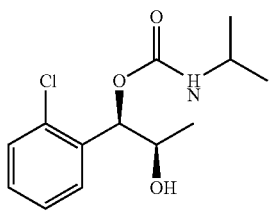 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).

¹H NMR (400MHz, CDCl₃) δ 1.13 (d, J=6Hz, 3H), 1.20 (dd, J=9.2Hz, 6H), 2.23 (s, 1H), 3.77~3.82 (m, 1H), 4.10 (s, 1H), 4.76 (br s, 1H), 5.98 (d, J=5.6Hz, 1H), 7.23~7.41 (m, 4H)

Example 79

Synthesis of 1-(2-chlorophenyl)-2-hydroxypropyl-1-N-isopropylcarbamate (79)

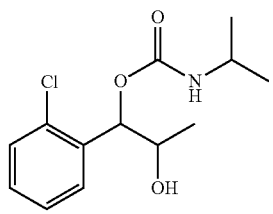 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 10~30%).

¹H NMR (400MHz, CDCl₃) δ 1.14 (d, J=6Hz, 3H), 1.21 (dd, J=6Hz, 6H), 2.16 (d, J=5Hz, 1H), 3.81 (t, J=6Hz, 1H), 4.11 (d, J=5Hz, 1H), 4.73 (br s, 1H), 5.98 (d, J=5Hz, 1H), 7.24~741 (m, 4H)

Example 80

Synthesis of 1-(2-chlorophenyl)-(S)-2-hydroxypropyl-(S)-1-N-cyclopropylcarbamate (80)

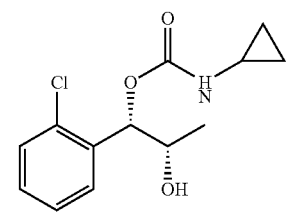 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

¹H NMR (400MHz, CDCl₃) δ0.53~0.60 (m, 2H), 0.74 (s, 2H), 1.21 (d, J=6.0Hz, 3H), 2.19 (s, 1H), 2.59 (s, 1H), 4.11~4.15 (m, 1H), 5.13 (br s, 1H), 5.99 (d, J=5.20Hz, 1H), 7.23~7.40 (m, 4H)

Example 81

Synthesis of 1-(2-chlorophenyl)-(R)-2-hydroxypropyl-(R)-1-N-cyclopropylcarbamate (81)

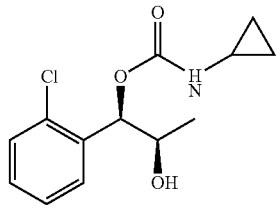 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

¹H NMR (400MHz, CDCl₃) δ0.53~0.60 (m, 2H), 0.74 (s, 2H), 1.21 (d, J=6.0Hz, 3H), 2.19 (s, 1H), 2.59 (s, 1H), 4.11~4.15 (m, 1H), 5.13 (br s, 1H), 5.99 (d, J=5.20Hz, 1H), 7.23~7.40 (m, 4H)

Example 82

Synthesis of 1-(2-chlorophenyl)-2-hydroxypropyl-1-N-cyclopropylcarbamate (82)

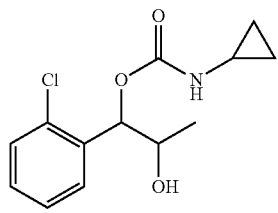 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

¹H NMR (400MHz, CDCl₃) δ 0.71 (s, 2H), 1.19 (d, J=6Hz, 3H), 2.45 (S, 1H), 2.57 (S, 1H), 4.08~4.12 (m, 1H), 5.26 (s, 1H), 5.97 (d, J=4Hz, 1H), 7.22~7.54 (m, 4H)

Example 83

Synthesis of 1-(2-chlorophenyl)-(S)-2-hydroxypropyl-(S)-1-N-cyclohexylcarbamate (83)

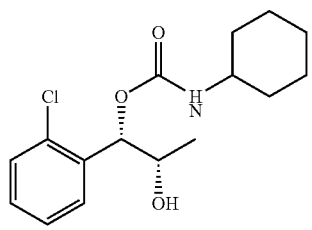 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

¹H NMR (400MHz, CDCl₃) δ1.10~1.39 (m, 7H), 1.61 (s, 3H), 1.71~1.74 (m, 2H), 1.87 (d, J=11.2Hz, 1H), 2.48 (d, J=10.8Hz, 1H), 3.46 (t, J=4Hz, 1H), 4.10~4.11 (m, 1H), 4.80 (br s 1H), 5.97 (d, J=5.6Hz, 1H), 7.23~7.41 (m, 4H)

Example 84

Synthesis of 1-(2-chlorophenyl)-(R)-2-hydroxypropyl-(R)-1-N-cyclohexylcarbamate (84)

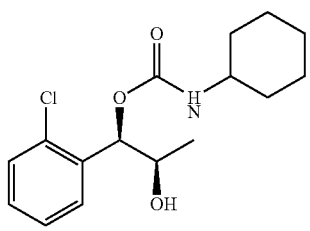 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

¹H NMR (400MHz, CDCl₃) δ1.10~1.39 (m, 7H), 1.61 (s, 3H), 1.71~1.74 (m, 2H), 1.87 (d, J=11.2Hz, 1H), 2.48 (d, J=10.8Hz, 1H), 3.46 (t, J=4Hz, 1H), 4.10~4.11 (m, 1H), 4.80 (br s 1H), 5.97 (d, J=5.6Hz, 1H), 7.23~7.41 (m, 4H)

Example 85

Synthesis of 1-(2-chlorophenyl)-2-hydroxypropyl-1-N-cyclohexylcarbamate (85)

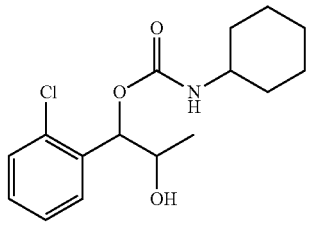 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).

¹H NMR (400MHz, CDCl₃) δ 1.12~1.19 (m, 3H), 1.22 (d, J=6Hz, 3H), 1.27~1.37 (m, 1H), 1.71 (t, J=6Hz, 2H), 1.86~1.88 (m, 1H), 1.97~2.00 (m, 1H), 2.18 (d, J=4Hz, 1H), 3.47 (S, 1H), 4.12 (t, J=6Hz, 1H), 4.78 (S, 1H), 5.97 (d, J=6Hz, 1H), 7.23~7.40 (m, 4H)

Example 86

Synthesis of 1-(2-chlorophenyl)-(S)-2-hydroxypropyl-(S)-1-N-benzylcarbamate (86)

A regioisomer of monocarbamate was separated and purified by conducting the silica gel column chromatography as described in Example 20, to obtain the title compound (0.19 g, yield 10~30%).

¹H NMR (400MHz, CDCl₃) δ 1.23 (d, J=6Hz, 3H), 2.16 (d, J=4Hz, 1H), 4.12 (t, J=6Hz, 1H), 4.31~4.44 (m, 2H), 5.22 (br S, 1H), 6.04 (d, J=6Hz, 1H), 7.27~7.42 (m, 9H)

Example 87

Synthesis of 1-(2-chlorophenyl)-(R)-2-hydroxypropyl-(R)-1-N-benzylcarbamate (87)

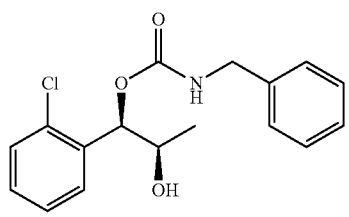 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

¹H NMR (400MHz, CDCl₃) δ 1.23 (d, 1~6Hz, 3H), 2.16 (d, J=4Hz, 1H), 4.12 (t, J=6Hz, 1H), 4.31~4.44 (m, 2H), 5.22 (br S, 1H), 6.04 (d, J=6Hz, 1H), 7.27~7.42 (m, 9H)

Example 88

Synthesis of 1-(2-chlorophenyl)-2-hydroxypropyl-1-N-benzylcarbamate (88)

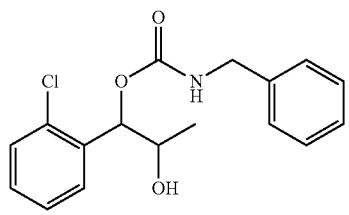 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

¹H NMR (400MHz, CDCl₃) δ 1.23 (d, J=6Hz, 3H), 2.16 (d, J=4Hz, 1H), 4.12 (t, J=6Hz, 1H), 4.31~4.44 (m, 2H), 5.22 (br S, 1H), 6.04 (d, J=6Hz, 1H), 7.27~7.42 (m, 9H)

Example 89

Synthesis of 1-(2,4-dichlorophenyl)-(S)-2-hydroxypropyl-(S)-1-carbamate (89)

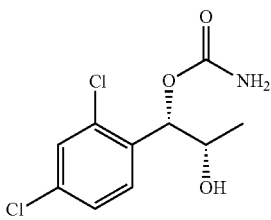 [SMILES: C[C@H](O)[C@@H](OC(N)=O)c1ccc(Cl)cc1Cl]

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).

¹H NMR (400MHz, CDCl₃) δ1.13 (d, J=6.8Hz, 3H), 2.49 (d, J=4.0Hz, 1H), 4.66~4.74 (m, 1H), 4.76 (br s, 2H), 6.20 (d, J=8.8Hz, 1H), 7.30 (d, J=8.4Hz, 1H), 7.39 (d, J=2.0Hz, 2H), 7.50 (dd, J=8.4 Hz, 2.0Hz, 1H)

Example 90

Synthesis of 1-(2,6-dichlorophenyl)-(S)-2-hydroxypropyl-(S)-1-carbamate (90)

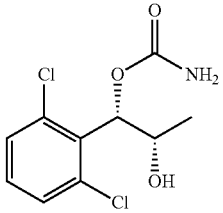 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).

¹H NMR (400MHz, CDCl₃) δ1.13 (d, J=6.8Hz, 3H), 2.49 (d, J=4.0 Hz, 1H), 4.66~4.74 (m, 1H), 4.76 (br s, 2H), 6.20 (d, J=8.8Hz, 1H), 7.25~7.40 (m, 3H)

Example 91

Synthesis of 1-(2,3-dichlorophenyl)-(S)-2-hydroxypropyl-(S)-1-carbamate (91)

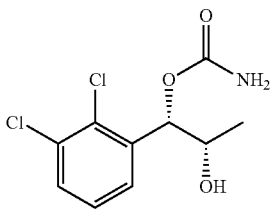 [SMILES: C[C@H](O)[C@@H](OC(N)=O)c1cccc(Cl)c1Cl]

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).

$^1$H NMR (400MHz, CDCl$_3$) δ1.15 (d, J=6.4Hz, 3H), 3.66 (d, J=9.2Hz, 1H), 4.73 (br s, 2H), 5.43 (t, J=9.0Hz, 1H), 5.62~5.69 (m, 1H), 7.18~7.22 (m, 3H),

Example 92

Synthesis of 1-(2,4-dichlorophenyl)-(S)-2-hydroxy-butyl-(S)-1-carbamate (92)

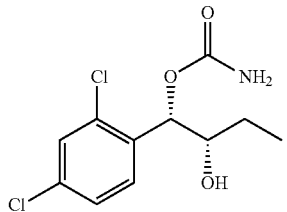

The substantially same method as described in Example 68 was conducted, except that 1-(2,4-dichlorophenyl)-(S,S)-1,2-butanediol (Preparation example 29) was used instead of 1-(2-chlorophenyl)(S,S)-1,2-propanediol (Preparation example 14), to obtain the title compound (0.07 g, yield 10~30%).

$^1$H NMR (400MHz, CDCl$_3$) δ0.77 (t, J=7.4Hz, 3H), 0.92~1.01 (m, 1H), 1.18~1.28 (m, 1H), 4.06~4.13 (m, 1H), 4.96 (d, J=6.0Hz, 1H), 5.91 (d, J=8.8Hz, 1H), 6.4 (br s, 2H), 7.30~7.50 (m, 3H)

Example 93

Synthesis of 1-(2,6-dichlorophenyl)-(S)-2-hydroxy-butyl-(S)-1-carbamate (93)

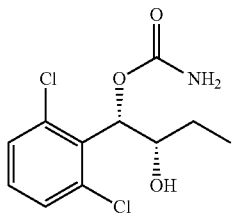 [SMILES: CC[C@H](O)[C@@H](OC(N)=O)c1c(Cl)cccc1Cl]

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

$^1$H NMR (400MHz, CDCl$_3$) δ0.77 (t, J=7.4Hz, 3H), 0.92~1.01 (m, 1H), 1.18~1.28 (m, 1H), 4.06~4.13 (m, 1H), 4.96 (d, J=6.0Hz, 1H), 5.91 (d, J=8.8Hz, 1H), 6.4 (br s, 2H), 7.25~7.40 (m, 3H)

Example 94

Synthesis of 1-(2,4-dichlorophenyl)-(S)-2-hydroxy-3-methyl-butyl-(S)-1-carbamate (94)

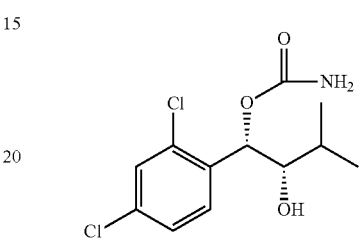

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

$^1$H NMR (400MHz, CDCl$_3$) δ1.00 (t, J=7.2Hz, 6H), 1.73~1.79 (m, 1H), 3.67~3.69 (m, 1H), 4.96 (d, J=6.0Hz, 1H), 5.91 (d, J=8.8Hz, 1H), 6.42 (br s, 2H), 7.30~7.50 (m, 3H)

Example 95

Synthesis of 1-(2,6-dichlorophenyl)-(S)-2-hydroxy-3-methyl-butyl-(S)-1-carbamate (95)

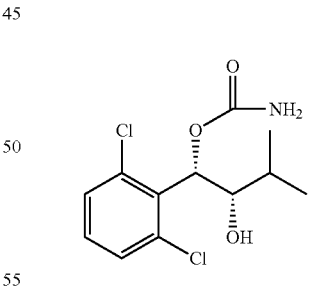

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

$^1$H NMR (400MHz, CDCl$_3$) δ1.00 (t, J=7.2Hz, 6H), 1.73~1.79 (m, 1H), 3.67~3.69 (m, 1H), 4.96 (d, J=6.0Hz, 1H), 5.91 (d, J=8.8Hz, 1H), 6.42 (br s, 2H), 7.25~7.40 (m, 3H)

Example 96

Synthesis of 1-(2,4-dichlorophenyl)-(S)-2-hydroxy-hexyl-(S)-1-carbamate (96)

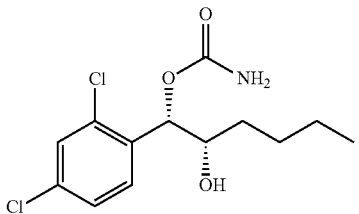 [SMILES: CCCC[C@H](O)[C@@H](OC(N)=O)c1ccc(Cl)cc1Cl]

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4Hz, 1H), 7.30~7.50 (m, 3H)

Example 97

Synthesis of 1-(2,6-dichlorophenyl)-(S)-2-hydroxy-hexyl-(S)-1-carbamate (97)

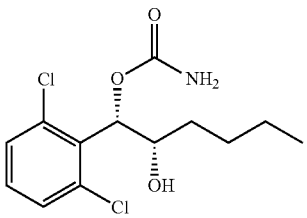 [SMILES: CCCC[C@H](O)[C@@H](OC(N)=O)c1c(Cl)cccc1Cl]

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4Hz, 1H), 7.16~7.34 (m, 3H)

Example 98

Synthesis of 1-(2,4-dichlorophenyl)-(R)-2-hydroxy-propyl-(R)-1-carbamate (98)

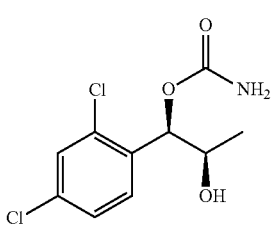 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR (400MHz, CDCl$_3$) δ1.13 (d, J=6.8Hz, 3H), 2.49 (d, J=4.0Hz, 1H), 4.66~4.74 (m, 1H), 4.76 (br s, 2H), 6.20 (d, J=8.8Hz, 1H), 7.30~7.50 (m, 3H)

Example 99

Synthesis of 1-(2,6-dichlorophenyl)-(R)-2-hydroxy-propyl-(R)-1-carbamate (99)

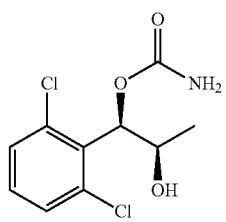 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR (400MHz, CDCl$_3$) δ1.13 (d, J=6.8Hz, 3H), 2.49 (d, J=4.0Hz, 1H), 4.66~4.74 (m, 1H), 4.76 (br s, 2H), 6.20 (d, J=8.8Hz, 1H), 7.25~7.40 (m, 3H)

Example 100

Synthesis of 1-(2,3-dichlorophenyl)-(R)-2-hydroxy-propyl-(R)-1-carbamate (100)

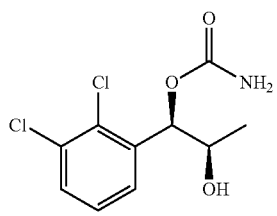 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR (400MHz, CDCl$_3$) δ1.15 (d, J=6.4Hz, 3H), 3.66 (d, J=9.2Hz, 1H), 4.73 (br s, 2H), 5.43 (t, J=9.0Hz, 1H), 5.62~5.69 (m, 1H), 7.18~7.22 (m, 3H),

Example 101

Synthesis of 1-(2,4-dichlorophenyl)-(R)-2-hydroxy-butyl-(R)-1-carbamate (101)

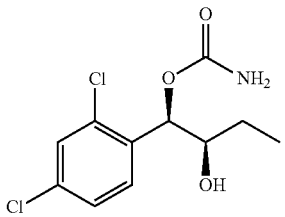 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR (400MHz, CDCl$_3$) δ0.77 (t, J=7.4Hz, 3H), 0.92~1.01 (m, 1H), 1.18~1.28 (m, 1H), 4.06~4.13 (m, 1H), 4.96 (d, J=6.0Hz, 1H), 5.91 (d, J=8.8Hz, 1H), 6.4 (br s, 2H), 7.30~7.50 (m, 3H)

Example 102

Synthesis of 1-(2,6-dichlorophenyl)-(R)-2-hydroxy-butyl-(R)-1-carbamate (102)

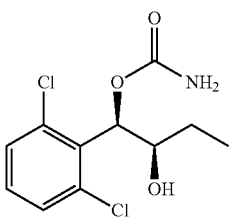 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%).

$^1$H NMR (400MHz, CDCl$_3$) δ0.77(t, J=7.4Hz, 3H), 0.92~1.01(m, 1H), 1.18~1.28(m, 1H), 4.06~4.13(m, 1H), 4.96(d, J=6.0Hz, 1H), 5.91(d, J=8.8Hz, 1H), 6.4(br s, 2H), 7.25~7.40(m, 3H)

Example 103

Synthesis of 1-(2,4-dichlorophenyl)-(R)-2-hydroxy-3-methyl-butyl-(R)-1-carbamate (103)

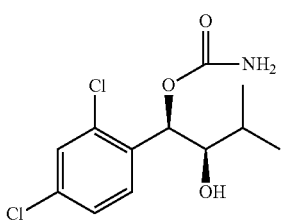 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR (400MHz, CDCl$_3$) δ1.00 (t, J=7.2Hz, 6H), 1.73~1.79 (m, 1H), 3.67~3.69 (m, 1H), 4.96 (d, J=6.0Hz, 1H), 5.91 (d, J=8.8Hz, 1H), 6.42 (br s, 2H), 7.30~7.50 (m, 3H)

Example 104

Synthesis of 1-(2,6-dichlorophenyl)-(R)-2-hydroxy-3-methyl-butyl-(R)-1-carbamate (104)

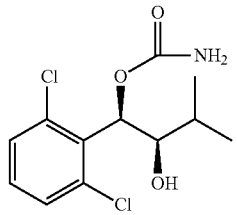 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR (400MHz, CDCl$_3$) δ1.00(t, J=7.2Hz, 6H), 1.73~1.79(m, 1H), 3.67~3.69(m, 1H), 4.96(d, J=6.0Hz, 1H), 5.91(d, J=8.8Hz, 1H), 6.42(br s, 2H), 7.25~7.40(m, 3H)

Example 105

Synthesis of 1-(2,4-dichlorophenyl)-(R)-2-hydroxy-hexyl-(R)-1-carbamate (105)

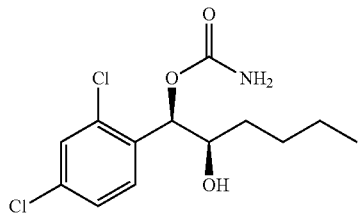 [SMILES: CCCC[C@@H](O)[C@H](OC(N)=O)c1ccc(Cl)cc1Cl]

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4Hz, 1H), 7.30~7.50 (m, 3H)

Example 106

Synthesis of 1-(2,6-dichlorophenyl)-(R)-2-hydroxy-hexyl-(R)-1-carbamate (106)

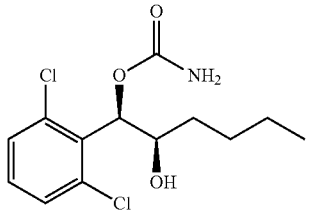 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4Hz, 1H), 7.16~7.34 (m, 3H)

Example 107

Synthesis of 1-(2,4-dichlorophenyl)-2-hydroxypropyl-1-carbamate (107)

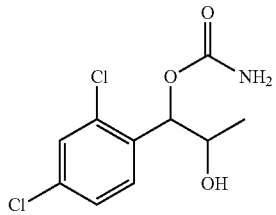 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).

$^1$H NMR (400MHz, CDCl$_3$) δ1.13 (d, J=6.8Hz, 3H), 2.49 (d, J=4.0Hz, 1H), 4.66~4.74 (m, 1H), 4.76 (br s, 2H), 6.20 (d, J=8.8Hz, 1H), 7.30~7.50 (m, 3H)

Example 108

Synthesis of 1-(2,6-dichlorophenyl)-2-hydroxypropyl-1-carbamate (108)

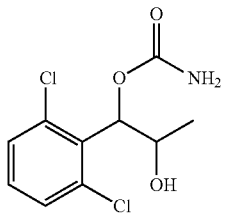 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

$^1$H NMR (400MHz, CDCl$_3$) δ1.13 (d, J=6.8Hz, 3H), 2.49 (d, J=4.0Hz, 1H), 4.66~4.74 (m, 1H), 4.76 (br s, 2H), 6.20 (d, J=8.8Hz, 1H), 7.25~7.40 (m, 3H)

Example 109

Synthesis of 1-(2,3-dichlorophenyl)-2-hydroxypropyl-1-carbamate (109)

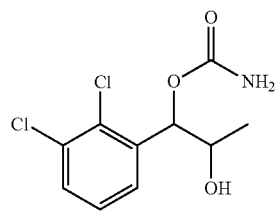 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).

$^1$H NMR (400MHz, CDCl$_3$) δ1.15 (d, J=6.4Hz, 3H), 3.66 (d, J=9.2Hz, 1H), 4.73 (br s, 2H), 5.43 (t, J=9.0Hz, 1H), 5.62~5.69 (m, 1H), 7.18~7.22 (m, 3H),

Example 110

Synthesis of 1-(2,4-dichlorophenyl)-2-hydroxybutyl-1-carbamate (110)

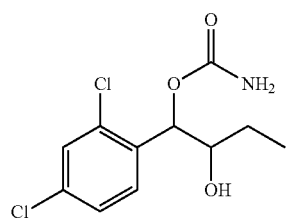 [SMILES: CCC(O)C(OC(N)=O)c1ccc(Cl)cc1Cl]

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

$^1$H NMR (400MHz, CDCl$_3$) δ0.77 (t, J=7.4Hz, 3H), 0.92~1.01 (m, 1H), 1.18~1.28 (m, 1H), 4.06~4.13 (m, 1H), 4.96 (d, J=6.0Hz, 1H), 5.91 (d, J=8.8Hz, 1H), 6.4 (br s, 2H), 7.30~7.50 (m, 3H)

Example 111

Synthesis of 1-(2,6-dichlorophenyl)-2-hydroxybutyl-1-carbamate (111)

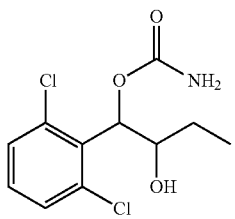 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

$^1$H NMR (400MHz, CDCl$_3$) δ0.77 (t, J=7.4Hz, 3H), 0.92~1.01 (m, 1H), 1.18~1.28 (m, 1H), 4.06~4.13 (m, 1H), 4.96 (d, J=6.0Hz, 1H), 5.91 (d, J=8.8Hz, 1H), 6.4 (br s, 2H), 7.25~7.40 (m, 3H)

Example 112

Synthesis of 1-(2,4-dichlorophenyl)-2-hydroxy-3-methyl-butyl-1-carbamate (112)

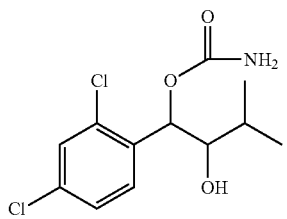 [SMILES: CC(C)C(O)C(OC(N)=O)c1ccc(Cl)cc1Cl]

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

$^1$H NMR (400MHz, CDCl$_3$) δ1.00 (t, J=7.2Hz, 6H), 1.73~1.79 (m, 1H), 3.67~3.69 (m, 1H), 4.96 (d, J=6.0Hz, 1H), 5.91 (d, J=8.8Hz, 1H), 6.42 (br s, 2H), 7.30~7.50 (m, 3H)

Example 113

Synthesis of 1-(2,6-dichlorophenyl)-2-hydroxy-3-methyl-butyl-1-carbamate (113)

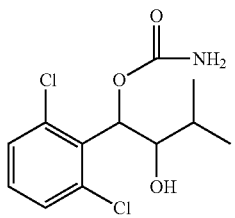 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

$^1$H NMR (400MHz, CDCl$_3$) δ1.00 (t, J=7.2Hz, 6H), 1.73~1.79 (m, 1H), 3.67~3.69 (m, 1H), 4.96 (d, J=6.0Hz, 1H), 5.91 (d, J=8.8Hz, 1H), 6.42 (br s, 2H), 7.25~7.40 (m, 3H)

Example 114

Synthesis of 1-(2,4-dichlorophenyl)-2-hydroxyhexyl-1-carbamate (114)

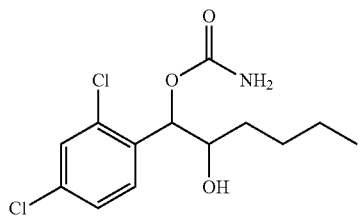 [SMILES: CCCCC(O)C(OC(N)=O)c1ccc(Cl)cc1Cl]

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4 Hz, 1H), 7.30~7.50 (m, 3H)

Example 115

Synthesis of 1-(2,6-dichlorophenyl)-2-hydroxyhexyl-1-carbamate (115)

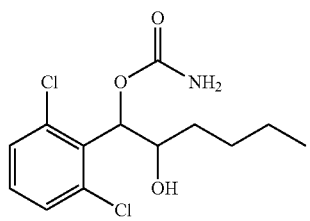 [SMILES: CCCCC(O)C(OC(N)=O)c1c(Cl)cccc1Cl]

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR (400MHz, CDCl$_3$) δ0.85 (t, J=7.2Hz, 3H), 1.18~1.33 (m, 4H), 1.48~1.55 (m, 2H), 2.35 (d, J=4.4Hz, 1H), 4.45~4.50 (m, 1H), 4.76 (br s, 2H), 6.21 (d, J=8.4Hz, 1H), 7.16~7.34 (m, 3H)

TABLE 1

Compounds 1 to 67 having the structure of Chemical Formula 1 where 'R⁷' is a carbamoyl derivative and 'R⁶' is H

| No. | $R^1$-$R^5$ | n (position) | $1^{st}$ Chiral | $2^{nd}$ Chiral | $R^8$ | $R^7$ = carbamoyl derivative, $A^1$= | $R^6$ = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac, | Rac. | Me | H | H |
| 57 | Cl | 2(2,4-) | Rac, | Rac. | Et | H | H |
| 58 | Cl | 2(2,6-) | Rac, | Rac. | Et | H | H |
| 59 | Cl | 2(2,4-) | Rac, | Rac. | Isopropyl | H | H |
| 60 | Cl | 2(2,6-) | Rac, | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'R$^7$' is H and 'R$^6$' is a carbamoyl derivative

| No. | R$^1$-R$^5$ | n (position) | 1$^{st}$ Chiral | 2$^{nd}$ Chiral | R$^8$ | R$^7$ = H | R$^6$ = carbamoyl derivative, A$^1$= |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Neuroprotection Activity Using the Lithium-Pilocarpine Model of Temporal Lobe Epilepsy Male Sprague-Dawley rats (purchased from Orient Bio Inc. Korea) of body weight 175-230 g were used for these studies and housed 4 rats per cage for 4-5 days. On the day prior to status epilepsy (SE), rats received 127 mg/kg lithium chloride (Sigma, St. Louis, Mo., U.S.A.) intraperitoneal (i.p.). Approximately 18-20 h following this treatment, rats were given an i.p. injection of 43 mg/kg pilocarpine (Sigma). An i.p. injection of 2 mg/kg methyl-scopolamine (Sigma) was administered 30 min prior to pilocarpine to block the effects of the muscarinic agonist on peripheral cholinergic receptors. The effects of various dose compound (or example) 1, 65 and 67, dissolved in 30% Poly Ethylene Glycol 400 (Acros Organics, Geel, Belgium) were studied at 30 min after SE onset. The drugs were administered i.p. in a volume of 2 ul/g body weight. Pharmacological effects of all the test materials were evaluated to compared test groups (n=8) with a control group (n=8). Control group was administrated vehicle, only. All animals were kept for 2 weeks to look at the mortality and quantification of cell densities was performed 14 days after SE in test groups and control rats not subjected to SE. The animals were deeply anesthetized by injection lumpun plus zoletile, 7:3 (v/v) and perfused transcardially with 150 ml of ice-cold 0.01 M phosphate buffer followed by 250 ml of freshly prepared ice-cold 4% paraformaldehyde (PFA) in 0.1 M phosphate buffer, pH 7.4. The brains were removed and postfixed in the same fixative for an additional 22~24 h at 4° C., and then transferred to 30% sucrose for cryoprotection until the samples were precipitated. Brains were frozen in methyl butane with dry ice and stored at −80° C. Serial coronal 25-mm slices were cut in a cryostat (Microtome HM 1850, Leica, Germany) and put the sections onto the slides, and air-dried before thionine staining. Every fifth section was selected for morphometric analysis.

Neuronal density quantification was performed automatically with the MCID Elite software (Interfocus Ltd, Linton, UK) by counting the number of neurons present in a defined area of the structure of interest (dorsal hippocampus—CA1, CA3, DZ) and carried out with a microscopic enlargement of 200- or 400-fold. Countings were performed twice on each side in each region by a single observer unaware of animal's treatment and averaged. In each structure, the mean and minimal surface area of the neurons were determined in order to count only neurons and exclude glial cells with smaller cell bodies. (Ref., Jennifer François, Katuschia Germe, Arielle Ferrandon, Estelle Koning, Astrid Nehlig (2011) Carisbamate has powerful disease-modifying effects in the lithium-pilocarpine model of temporal lobe epilepsy, Neuropharmacology 61: 313~328)

[Statistical Analysis]

Data were expressed as mean±sem. Statistical analysis of difference between groups was evaluated by ANOVA followed by Dunnett's test or Bonferroni test as a post hoc analysis using Statistica (Statsoft, Inc., USA). Difference was considered statistically significant when the p value was less than 0.05.

DPPH

The free radical scavenging capacity of the extracts was determined using DPPH (Sigma, U.S.A). DPPH solution (0.2 mM) was prepared in 99.8% methanol. Compounds were mixed with methanol to prepare the stock solution (30% w/w). Freshly prepared DPPH solution was 1 ml taken in test tubes and test compounds were 1 ml added followed to every test tube so that the final volume 2 ml and after 20 min, the absorbance was read at 517 nm using a spectrophotometer (OPTIZEN, Korea). Control sample was prepared containing the same volume without test compounds. 99.8% methanol was served as blank. % radical scavenging activity (RSA) of the DPPH free radical was measured by using the following equation (Rohmam, A., Riyanto, S., Yuniarti, N., Saputra, W. R., Utami, R. and Mulatsih, W. 2010. Antioxidant activity, total phenolic, and total flavaonoid of extracts and fractions of red fruit (*Pandanus conoideus* Lam). International Food Research Journal 17: 97-106.):

$$\text{Radical scavenging activity(RSA) \%} = [(Abs_{control} - Abs_{sample})/Abs_{control}] \times 100$$

TABLE 3

Measurement results of anti-oxidative stress of compounds

| Compound No. | % radical scavenging activity (Concentration; 30%) |
|---|---|
| 1 | 12.59 |
| 3 | 19.44 |
| 6 | 6.32 |
| 12 | 6.56 |
| 13 | 6.93 |
| 14 | 13.60 |
| 15 | 7.10 |
| 25 | 7.33 |
| 29 | 7.55 |
| 31 | 51.97 |
| 32 | 10.99 |
| 37 | 7.77 |
| 40 | 7.98 |
| 42 | 8.30 |
| 44 | 28.70 |
| 63 | 7.48 |
| 65 | 5.29 |
| 67 | 5.69 |

Anti-Excitation Activity Using MEs

In the MES test (Ref., G. Villetti et al. Neuropharmacology 40 (2001) 866-878), an electrical stimulus (mice; 50 mA, 60 Hz, 0.2 sec and rats; 150 mA 60 Hz, 0.2 sec in the test animal) supplied by 11A Shocker (IITC Life Science Company) was delivered through corneal electrodes. All mice assigned to any electroshock at peak time were treated with each test compound sample which was dissolved in 30% PEG400 prepared by saline solvent applied to oral before the test. If the test animal stretching their hind limb in a straight line weren't observed in the MES test, the results indicate that the test sample had an anti-excitation activity. Three doses of the test sample were administered orally to over 18 mice (6 mice per dose) for evaluating the respective doses at which 50% of the animals are protected from seizure (ED50). The value of ED50 (median effective dose) is calculated by Litchfield and Wicoxon log-probit method which is a dose-response relationship. Then, the test results are shown in following Table 4. Experimental animal, male ICR mice and male SD rats, were purchased from OrientBio or Nara biotech, Korea, and housed 4-5 mice per a cage for 4-5 days. The range of mice body weight was used between 19 and 26 grams. The obtained results are shown in following Table 4.

Neurotoxicity

The measurement of neurotoxicity of the test compounds was conducted by the method of Dunham and Miya [Dunham, N. W. and Miya, T. S. 1957. A note on a simple apparatus for detecting neurological deficit in rats and mice. J. Am. Pharm. Assoc. (Baltimore) 46: 208-209]. In the method, motor abilities of the test animals can be determined by observing whether the test animals can walk without falling from a rotator, thereby determining the value of neurotoxicity of each compound. Term "TD50" means the respective dose of the test compound at which 50% of the test animal exhibit neurotoxicity. They were pre-trained on the rotarod (Rotarod; Columbus instrument, rota-max, USA) at 6 rpm for 5 min 24 hr prior to the test. The peak time was determined by administration test material's random dose for 0.5, 1, 2, 4 hour. To evaluate the minimal neurotoxicity of the compound, the mice were placed on the Rotarod (rod circle; 3 Cm) at 6 rpm and the test animal fails to maintain walking once or more during 1 minute, it can be regarded that the test animal exhibits neurotoxicity. The ratio of TD50 to ED50 (TD50/ED50) is called as a protective index, and useful as a parameter for comparison of pharmaceutical efficacy and neurotoxicity. The obtained results are shown in following Table 4.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

TABLE 4

Measurement results of anti-excitation activity of compounds in the test animals (Mice)

| Compound No. | MES test(po) ED50(mg/kg) | Peak Time(h) | татD50 (mg/kg po) | PI(TD50/ED50) in MES |
|---|---|---|---|---|
| 1 | 13.0 | 2 | 218.1 | 16.8 |
| 2 | 51.0 | 0.25 | 372.0 | 7.3 |
| 3 | 31.4 | 2 | 378.3 | 12.0 |
| 4 | 82.4 | 0.5 | — | — |
| 5 | 84.1 | 0.5 | 275.2 | 3.3 |
| 6 | 22.2 | 1 | — | — |
| 8 | 100 $^a$(100%) | — | — | — |

TABLE 4-continued

Measurement results of anti-excitation activity of compounds in the test animals (Mice)

| Com-pound No. | MES test(po) ED50(mg/kg) | Peak Time(h) | TD50 (mg/kg po) | PI(TD50/ED50) in MES |
|---|---|---|---|---|
| 9 | 67.1 | 0.5 | — | — |
| 12 | 100 $^a$(75%) | — | — | — |
| 13 | 200 $^a$(75%) | — | — | — |
| 14 | 200 $^a$(100%) | — | — | — |
| 15 | 100 $^a$(75%) | — | — | — |
| 16 | 200 $^a$(25%) | — | — | — |
| 18 | 200 $^a$(100%) | — | — | — |
| 23 | 200 $^a$(25%) | — | — | — |
| 25 | 200 $^a$(25%) | — | — | — |
| 29 | 200 $^a$(75%) | — | — | — |
| 30 | 200 $^a$(25%) | — | — | — |
| 31 | 200 $^a$(25%) | — | — | — |
| 32 | 200 $^a$(100%) | — | — | — |
| 36 | 82.8 | — | — | — |
| 37 | 25.8 | 0.25 | 131.6 | 5.1 |
| 38 | 91.4 | 2 | — | — |
| 39 | 41.2 | 1 | — | — |
| 40 | 46.9 | — | — | — |
| 42 | 35.2 | 0.5 | — | — |
| 43 | 100 $^a$(25%) | — | — | — |
| 44 | 100 $^a$(75%) | — | — | — |
| 46 | 35.2 | 1 | — | — |
| 63 | 50 $^a$(100%) | — | — | — |
| 65 | 50 $^a$(100%) | — | — | — |
| 67 | 100 $^a$(100%) | — | — | — |

$^a$Injection amount(mg/kg), Protection % = the percentage of activity compared to the vehicle only, respectively.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating a neurological disease comprising administering a pharmaceutically effective amount of a composition comprising a compound represented by the following formula 1 or pharmaceutically acceptable salt thereof as an active ingredient:

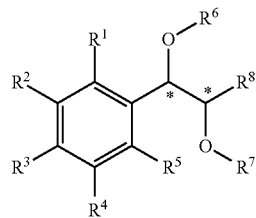

(1)

wherein the configuration at the carbon atoms bearing the asterisk (*) is (S); $R^1$, $R^2$, $R^3$, $R^4$ and $R^5$ are each independently selected from the group consisting of hydrogen and halogen;
$R^6$ is H and $R^7$ is

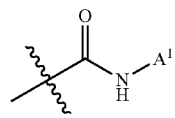

($A^1$ is selected from the group consisting of hydrogen, $C_1$-$C_5$ alkyl, $C_3$-$C_8$ cycloalkyl, $C_6$-$C_{10}$ aryl $C_1$-$C_3$ alkyl and bridged $C_6$-$C_8$ bicycloalkane); and $R^8$ is methyl, to a subject in need thereof, wherein the neurological disease is selected from the group consisting of neurodegenerative disease, autism spectrum disease and prion diseases, wherein the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia; wherein the autism spectrum disease is selected from the group consisting of autism, Asperger syndrome and pervasive developmental disorder not otherwise specified (PDD-NOS); and wherein the prion disease is selected from the group consisting of Creutzfeldt-Jakob disease, Gerstmann-Sträussler-Scheinker disease, Kuru disease and fatal familial insomnia.

2. The method according to claim 1, wherein $R^1$, $R^2$, $R^3$, $R^4$ and $R^5$ are each independently selected from the group consisting of hydrogen, chlorine, fluorine and iodine.

3. The method according to claim 1, wherein $A^1$ is selected from the group consisting of hydrogen, $C_1$-$C_4$ alkyl, cyclopropyl, cyclohexyl, phenyl $C_1$-$C_3$ alkyl and bicycloheptane.

4. The method according to claim 3, wherein $A^1$ is selected from the group consisting of hydrogen, $C_1$-$C_4$ alkyl, cyclopropyl, cyclohexyl, benzyl and bicycle[2.2.1]heptane.

5. A method for treating a neurological disease comprising administering a pharmaceutically effective amount of a composition comprising a compound or a pharmaceutically acceptable salt thereof as an active ingredient, wherein the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia; wherein the autism spectrum disease is selected from the group consisting of autism, Asperger syndrome and pervasive developmental disorder not otherwise specified (PDD-NOS); and wherein the prion disease is selected from the group consisting of Creutzfeldt-Jakob disease, Gerstmann-Sträussler-Scheinker disease, Kuru disease and fatal familial insomnia, wherein the compound is selected from the group consisting of:
1-(2-chlorophenyl)-(S)-1-hydroxypropyl-(S)-2-carbamate;
1-(2-chlorophenyl)-(S)-1-hydroxypropyl-(S)-2-N-methylcarbamate;

1-(2-chlorophenyl)-(S)-1-hydroxypropyl-(S)-2-N-propylcarbamate;
1-(2-chlorophenyl)-(S)-1-hydroxypropyl-(S)-2-N-isopropylcarbamate;
1-(2-chlorophenyl)-(S)-1-hydroxypropyl-(S)-2-N-cyclopropylcarbamate;
1-(2-chlorophenyl)-(S)-1-hydroxypropyl-(S)-2-N-cyclohexylcarbamate;
1-(2-chlorophenyl)-(S)-1-hydroxypropyl-(S)-2-N-benzylcarbamate;
1-(2-chlorophenyl)-(S)-1-hydroxypropyl-(S)-2-N-bicyclo[2,2,1]heptanecarbamate;
1-(2,4-dichlorophenyl)-(S)-1-hydroxypropyl-(S)-2-carbamate;
1-(2,6-dichlorophenyl)-(S)-1-hydroxypropyl-(S)-2-carbamate;
1-(2,3-dichlorophenyl)-(S)-1-hydroxypropyl-(S)-2-carbamate;
1-(2-fluorophenyl)-(S)-1-hydroxypropyl-(S)-2-carbamate; and
1-(2-iodophenyl)-(S)-1-hydroxypropyl-(S)-2-carbamate.

6. The method according to claim 5, wherein the compound is selected from the group consisting of:
1-(2-chlorophenyl)-(S)-1-hydroxypropyl-(S)-2-carbamate;
1-(2-chlorophenyl)-(S)-1-hydroxypropyl-(S)-2-N-methylcarbamate;
1-(2-chlorophenyl)-(S)-1-hydroxypropyl-(S)-2-N-cyclopropylcarbamate;
1-(2,4-dichlorophenyl)-(S)-1-hydroxypropyl-(S)-2-carbamate;
1-(2,6-dichlorophenyl)-(S)-1-hydroxypropyl-(S)-2-carbamate;
and
1-(2,3-dichlorophenyl)-(S)-1-hydroxypropyl-(S)-2-carbamate.

7. The method according to claim 1, wherein the pharmaceutically acceptable salt is produced by reacting the compound with an inorganic acid, an organic acid, an amino acid, sulfonic acid, an alkali metal or ammonium ion.

* * * * *